(12) United States Patent
Simpson et al.

(10) Patent No.: US 7,371,538 B2
(45) Date of Patent: May 13, 2008

(54) MICROLUMINOMETER CHIP AND METHOD TO MEASURE BIOLUMINESCENCE

(75) Inventors: Michael L. Simpson, Knoxville, TN (US); Michael J. Paulus, Knoxville, TN (US); Gary S. Sayler, Blaine, TN (US); Bruce M. Applegate, West Lafayette, IN (US); Steven A. Ripp, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 507 days.

(21) Appl. No.: 11/151,964

(22) Filed: Jun. 14, 2005

(65) Prior Publication Data

US 2006/0281067 A1   Dec. 14, 2006

Related U.S. Application Data

(60) Division of application No. 09/660,581, filed on Sep. 12, 2000, now Pat. No. 6,905,834, which is a continuation-in-part of application No. 08/978,439, filed on Nov. 25, 1997, now Pat. No. 6,117,643.

(51) Int. Cl.
  *G01N 33/554* (2006.01)
(52) U.S. Cl. .......... 435/7.32; 356/218; 356/226; 422/52; 422/55; 422/82.05; 422/82.08; 435/288.7; 436/164; 436/172; 436/805
(58) Field of Classification Search .......... 356/218, 356/226; 422/52, 55, 82.05, 82.08; 435/7.32, 435/288.7; 436/164, 172, 805
See application file for complete search history.

(56) References Cited

U.S. PATENT DOCUMENTS

| | | | |
|---|---|---|---|
| 4,157,560 A * | 6/1979 | Cade | 257/461 |
| 4,356,270 A | 10/1982 | Itakura | |
| 4,554,101 A | 11/1985 | Hopp | |
| 4,683,202 A | 7/1987 | Mullis | |
| 4,800,415 A * | 1/1989 | Simmons et al. | 257/26 |
| 5,441,884 A | 8/1995 | Baum | |
| 5,770,389 A | 6/1998 | Ching et al. | |
| 5,834,218 A | 11/1998 | Gremillet | |

FOREIGN PATENT DOCUMENTS

EP   0835940   4/1998

(Continued)

OTHER PUBLICATIONS

Simpson, et al., "Bioluminescent-bioreporter integrated circuits from novel whole-cell biosensors," TIBTECH 16:332-338, 1998.

(Continued)

*Primary Examiner*—Christopher L. Chin
(74) *Attorney, Agent, or Firm*—Akerman Senterfitt; Gregory A. Nelson; Amy A. Dobbelaere

(57) ABSTRACT

An integrated microluminometer includes an integrated circuit chip having at least one n-well/p-substrate junction photodetector for converting light received into a photocurrent, and a detector on the chip for processing the photocurrent. A distributed electrode configuration including a plurality of spaced apart electrodes disposed on an active region of the photodetector is preferably used to raise efficiency.

11 Claims, 54 Drawing Sheets

FOREIGN PATENT DOCUMENTS

| WO | WO89/06700 | 7/1989 |
|---|---|---|
| WO | WO93/22678 | 11/1993 |
| WO | WO97/06101 | 2/1997 |
| WO | WO97/12030 | 4/1997 |
| WO | WO98/26277 | 6/1998 |
| WO | WO99/27351 | 6/1999 |

OTHER PUBLICATIONS

Webb, et al., "Kinetics and Response of Pseudomonas fluorescens HK44 biosensor," Biotechnology & Bioengeineering, 54(5): 491-502, 1997.

Ahluwalia, et al., "A comparative study of protein immobilization techniques for optical immunosensors," Biosensors and Bioelectronics, 7:207-214, 1991.

Alvarez-Icaza, et al., "Mass production of biosensors," Anal. Chem., 65:525A-533A, 1993.

Anis, et al., "A fiber-optic immunosensor for detecting parathion," Anal. Lett., 25:627-635, 1992.

Arnold, "Fibre-optic biosensors," J. Biotechnol., 15:219-228, 1990.

Bluestein, et al., "Rapid response fiber optic evanescent wave immunosensors," Immunol. Ser., 53:145-170, 1990.

Blum, et al., "Design of luminescence photobiosensors," J. Biolumin. Chemilumin., 4:543-550, 1989.

Chee, et al., "Accessing genetic information with high-density DNA arrays," Science, 274:610-614, Oct. 1996.

Fodor, et al., "Multiplexed biochemical assays with biological chips," Nature, 364: 555-556, Aug. 1993.

Grate, et al., "Acoustic wave microsensors," Part 2, Anal. Chem., 65:987A-996A, 1993.

Griffiths, et al., "Biosensors—What real progress is being made?" Trends Biotechnol., 11:122-130, 1993.

Hacia, et al., "Detection of heterozygous mutations in BRCA1 using high denisty oligonucleotide arrays and two-colour fluorescence analysis," Nature Genetics, 14:441-447, Dec. 1996.

Hacia, et al., "Evolutionaory sequence comparisons using high-density oligonucleotide arrays," Nature Genetics, 18:155-158, Feb. 1998.

Herrero, et al., "Transposon vectors containing non-antibiotic resistance selection markers for cloning and stable chromosomal insertion of foreign genes in gram-negative bacteria," J. Bacteriol., 172:6557-6567, 1990.

Hill, et al., "A comparison of non-radioactive labeling and detection systems with synthetic oligonucleotide probes for the species identification of mosquitoes in the Anopheles gambiae complex," Am. J. Trop. Med. Hyg., 44(6):609-622, 1991.

Janata, "Principles of Chemical Sensors," Plenum Press, New York, 1989.

Kauffman, et al., "Enzyme electrode biosensors: theory and applications," Bioanal. Appl. Enzymes, 36:36-113, 1992.

Lee, et al., "Fibre optic biosensor assay of Newcastle Disease Virus," J. Immunol. Methods, 166(1):123-131, 1993.

Lipshutz, et al., "Using oligonucleotide probe arrays to access genetic diversity," Biotechniques, 19(3):442-447, 1995.

Mrksich, et al., "Patterning sellf-assembled mono-layers using microcontact printing: a new technology for biosensors," Trends Bio., 13:228-235, 1995.

Pease, et al., "Light-generated oligonucleotide arrays for rapid DNA sequence analysis," Proc. Natl. Acad. Sci. USA, 91:5022-5026, May 1994.

Ogert, et al., "Detection of Chostridium botulinum toxin A using a fibre optic based biosensor," Anal. Biochem., 205:306-312, 1992.

Swain, "Biosensors: a new realism", Ann. Biol. Clin. (Paris), 50:175-179, 1992.

Wingard, "Biosensors trends," Ann. NY Acad. Sci., 613:44-53, 1990.

Wood, et al., "Transduction in microbial biosensors using multiplexed bioluminescence," Biosensors & Bioelectronics, 11(3) 207-214, 1996.

Anderson, J. W., Rossi, S. S., Tukey, R. H. and Quattrochi, L. C. (1995) Environ. Toxicol. Chem. 14, 1159-1169.

Andrew, P. W. and Roberts, I. S. (1993) J. Clin. Microbiol. 31, 2251-2254.

Applegate, et al., "Pseudomonas putida B2: A tod-lux bioluminescent reporter for toluene and trichloroethylene co-metabolism," J. Ind. Microbiol., 18:4-9, 1997.

Armon, et al., "Sol-gel applications in environmental biotechnology," J. Biotech., 51:279-285, 1996.

ATP Luminescence Rapid Methods in Microbiology. (Ed. by P.E. Stanley, et al.), Society of Applied Bacteriol. Technical Series 26, Blackwell Scientific Publications, Oxford.

Bronstein, et al., "Chemiluminescent and bioluminescent reporter gene assays". Anal. Biochem. 219(1994): pp. 169-181.

Cassidy, et al., "Environmental applications of immobilized microbial cells: a review," J. Indust. Microbiol., 16:79-101, 1996.

Danilov, et al., "Bacterial luciferase as a biosensor of biologically active compounds," In: Wise DL (ed) Applied biosensors, Butterworth, Stonehan, Mass., pp. 39-78, 1989.

DiGrazia, "Microbial systems analysis of naphthalene degradation in a continuous flow soil slurry reactor," Ph.D. thesis, University of Tennessee, Knoxville, TN, USA, 1991.

Don, et al., "'Touchdown' PCR to circumvent spurious priming during gene amplification," Nuc. Acids Res., 19:4008, 1991.

Ensign, S.A., M. R. Hyman, and D. J. Arp. J. Bacteriol. 175:1971-1980 (1993).

Ensley, "Biochemical diversity of trichloroethylene metabolism," Ann. Rev. Microbiol., 45:283-299, 1991.

Figurski, et al. "Replication of origin-containing derivative of plasmid RK@ is dependent on a plasmid function provided in trans," Proc. Natl. Acad. Sci., 76:1648-1652, 1979.

Hall, Biosensors, Prentice-Hall, Englewood Press, New Jersey, 1991.

Haynes, et al., "A model for the application of gas chromatography to measurements of diffusion in bidispersed structural catalysts," AlChE J. 19:1043-1046, 1973.

Heietzer, et al.,"Optical biosensor for environmental online monitoring of naphthalene and salicylate bioavailability with a immobilized bioluminescent catabolic reporter bacterium," Appl. Environ. Microbiol., 60:1487-1494, 1994.

Heitzer, et al., "A versatile bioluminescent reporter system for organic pollutant bioavailability and biodegradation," In: Applications of Molecular Biology in Environmental Chemistry, Minear et al., eds., CRC Press, New York, pp. 191-208, 1995.

Heitzer, et al., "Specific and quantitative assessment of naphthalene and salicylate bioavailability by using a bioluminescent catabolic reporter bacterium," App. Environ. Microbiol., 58:1839-1846, 1992.

Heitzer, A. et al. (1992) Appl. Environ. Microbiol. 60, 1487-1494.

Kanasawud, et al "Studies on immbolization of thermophilic bacterium Thermus aquaticus YT-1 by entrapment in various matrices," Appl. Microbiol. & Biotech., 31:228-233, 1989.

Kataoka, et al., Liquid-phase mass transfer in ion exchange based on the hydraulic radius model, J. Chem. Eng. Jpn., 6:172-177, 1973.

King, et al., "Rapid, sensitive biolurninescent reporter technology for naphthalene exposure and biodegradation," Science, 249:778-781, 1990.

King, J. M. H. (1990) et al. Science 249, 778-781.

Kramer, et al., "Industrial CMOS Technology for the Integration of Optical Metrology Systems (photo-ASICs)". Sensors and Actuators A, vol. 34, 1992, pp. 21-30.

Kyte and Doolittle, J. Mol. Biol., 157:105-132, 1982.

Lackey, et al., "Biodegradation of chlorinated aliphatic hydrocarbon mixtures in a single-pass packed-bed reactor," Appl. Biochem. Biotech., 39/40:701-713, 1993.

Lloyd, et al., "A membrane-covered photobacterium probe for oxygen measurements in the nonomolar range," Analytical Biochemistry, 116:17-21, 1981.

Menn, et al., "NAH plasmid-mediated catabolism of anthracene and phenanthrene to naphthoic acids," Appl. Environ. Microbiol., 59(6):1938-1942, 1993.

Menn, et al., "Studies on 3-methylcatechol 2,3-dioxygenase and 2-hydroxy-6-oxohepta-2, 4-dienote hydrolase: key enzymes in the degradation of toluene by Pseudomonas putida F1," PhD Dissertation, University of Iowa, Iowa City, IA, 1991.

Menn, et al., "Location and sequence of the todF gene encoding 2-hydroxy-6-oxohepta-2, 4-dienote hydrolase in Pseudomonas putida F1," Gene, 104:91-94, 1991.

Oyass, et al., "The effective diffusion coefficient and distribution constant for small molecules in calcium alginate," Biotechnol. Bioeng., 47:492-500, 1995.

P. Z. Peebles, "Probability, Random Variables, and Random Signals", McGraw-Hill, New York, 1980, p. 225.

Rogowsky, et al., "Regulation of the vir genes of *Agrobacterium tumefaciens* plasmid pTiC58," J. Bacteriol., 169:5101-5112, 1987.

Ruthyen, In: Principles of adsorption and adsorption processes, John Wiley & Sons, New York, 1984.

Sadik, et al., "Pulsed amperometric detection of thaumatin using antibody-containing poly(pyrrole) electrodes," Analyst., 119:1997-2000, 1994.

Sambrook, et al., "In: Molecular cloning: a laboratory manual," 2nd ed. Cold Spring Harbor Laboratory Press, Plainview, NY, 1989.

Sayavedra-Soto, L. A., N. G. Hommes, and D. J. Arp. J. Bacteriol. 176:504-510 (1994).

Schell. "Regulation of naphthalene degradation genes of plasmid NAH7: example of a generalized positive control system in Pseudomonas and related bacteria," p. 165-176., 1990.

Selifonova, et al., "Use of an ipb-lux fusion to study regulation of the isopropylbenzene catabolism operon of Pseudomonas putida RE204 and to detect hydrophobic pollutants in the environment," Appl. Environ. Microbiol., 62:778-783, 1996.

Shaw, et al., "Transposon Tn4431 mutagenesis of *Xanthomonas campestris* pv. campestris: Characterization of a nonpathogenic mutant and cloning of a locus for pathogenicity," Mol. Plant-Microbe Int., 1:39-45, 1988.

Shreve, et al. "Comparison of substrate utilization and growth kinetics between immobilized and suspended Pseudomonas cells," Biotechnol. Bioeng., 41:370-379, 1993.

Simpson, et al., "Application Specific Spectral Response with CMOS Compatbile Photodiodes". IEEE Trans. Elect. Dev. 46, No. 5, May 1999, pp. 905-913.

Simpson, M. L., et al. Rev. of Sci. Instr. 69, No. 2, Feb. 1998, pp. 377-383.

Simpson, et al., "A Photo-Spectrometer Realized in a Standard CMOS IC Process", Rev. of Sci. Instr. 69, No. 2, Feb. 1998, pp. 377-383.

Simpson, et al., "Application Specific Spectral Response with CMOS Compatible Photodiodes", IEEE Trans. Elect. Dev. 46, No. 5, May 1999, pp. 905-913.

Smith, et al., "Analysis & environmental fate of Air Force distillate & high density fuels," Air Force Eng. and Serv. Ctr., Tyndall Air Force Based, FL, ESL-TR-81-54, 1981.

Stanier, Palleroni, Doudoroff, "The aerobic Pseudomonads: A taxonomic study," J. Gen. Microbiol., 41:159-271, 1966.

Steinberg, S. M. and Poziomek, E. J. (1995) Chemosphere 11, 2155-2197.

Tu, S. and Mager, H. I. X. (1995) Photochem. Photobiol. 62, 615-624.

Wackett, et al., "Degradation of trichloroethylene by toluene dioxygenase in whole-cell studies with Pseudomonas putida F1," Appl. Environ. Microbiol., 54:1703-1708, 1988.

Wang, et al., "Identification of a membrane protein and a truncated LysR-type regulator associated with the toluene degradation pathway in Pseudomonas putida F1," Mol. Gen. Genet., 246:570-579, 1995.

Wangemann, P. "Ca2+-dependent release of ATP from the organ of Corti measured with a luciferin-luciferase bioluminescence assay". Audit. Neurosci. 2(1996): pp. 187-192.

Webb, Analysis of Pseudomonas putida HK44 for PAH pollutant degradation and migration, Ph.D. dissertation, University of Tennessee, Knoxville, TN, USA, 1992.

Wood, "Luc Genes: introduction of colour into bioluminescence assays," Biolumin. & Chemilumin., 5:107-114, 1990.

* cited by examiner

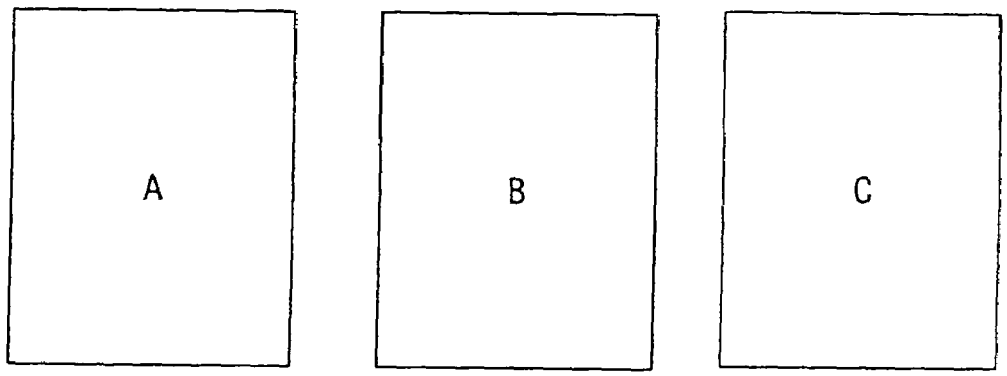
FIG. 9A
FIG. 9B
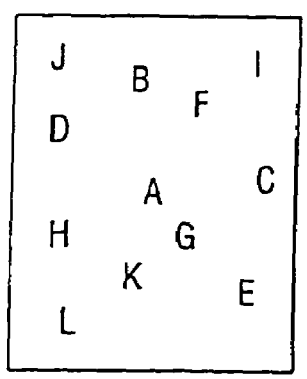
FIG. 9C
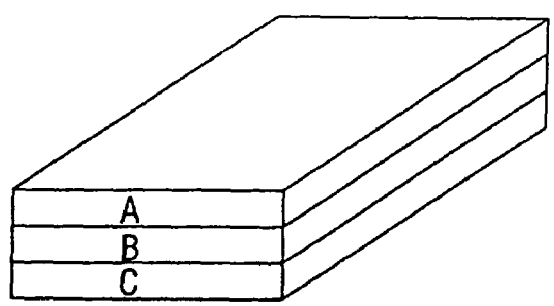
FIG. 9D

Primers for pLJS

SEQUENCE LISTING

```
<160> NUMBER OF SEQ ID NOS: 8

<210> SEQ ID NO 1
<211> LENGTH: 57
<212> TYPE: DNA
<213> ORGANISM: Artificial Sequence
<220> FEATURE:
<223> OTHER INFORMATION: Transposon Tn5
<220> FEATURE:
<221> NAME/KEY: prim_transcript
<222> LOCATION: (1)..(57)
<220> FEATURE:
<221> NAME/KEY: prim_transcript
<222> LOCATION: (1)..(57)
<223> OTHER INFORMATION: Transposon

<400> SEQUENCE: 1
gggcgctagc gaaatgttga ctgtctcttg atcagatttt caattcagaa gaactcg         57

<210> SEQ ID NO 2
<211> LENGTH: 56
<212> TYPE: DNA
<213> ORGANISM: Artificial Sequence
<220> FEATURE:
<221> NAME/KEY: prim_transcript
<222> LOCATION: (1)..(56)
```

```
<220> FEATURE:
<221> NAME/KEY: prim_transcript
<222> LOCATION: (1)..(56)
<223> OTHER INFORMATION: Transposon

<400> SEQUENCE: 2
cccgctgtgc ctttacaact tatgagtatg aaggaaaaag ttaagtcttc ttgagc        56

<210> SEQ ID NO 3
<211> LENGTH: 58
<212> TYPE: DNA
<213> ORGANISM: Artificial Sequence
<220> FEATURE:
<223> OTHER INFORMATION: Transposon Tn5
<220> FEATURE:
<221> NAME/KEY: prim_transcript
<222> LOCATION: (1)..(58)

<400> SEQUENCE: 3
cgaattctga ctcttataca caagttctag attgcggccg cttggttaaa aaatgagc     58

<210> SEQ ID NO 4
<211> LENGTH: 58
<212> TYPE: DNA
<213> ORGANISM: Artificial sequence
<220> FEATURE:
<223> OTHER INFORMATION: Transposon Tn5
<220> FEATURE:
<221> NAME/KEY: prim_transcript
<222> LOCATION: (1)..(58)

<400> SEQUENCE: 4
gataagaaaa ctaaatattc cctaaaagcg ctaagccgga taaccaattt tttactcg     58

<210> SEQ ID NO 5
<211> LENGTH: 47
<212> TYPE: DNA
<213> ORGANISM: Artificial
<220> FEATURE:
<223> OTHER INFORMATION: CLONING VECTOR

<400> SEQUENCE: 5
ccaagcgcgc aactagtcta gactaaagct agcctaggct gggatcc                 47

<210> SEQ ID NO 6
<211> LENGTH: 43
<212> TYPE: DNA
<213> ORGANISM: ARTIFICIAL
<220> FEATURE:
<223> OTHER INFORMATION: CLONING VECTOR

<400> SEQUENCE: 6
ggttcgcgcg ttaattggag tgatttccct tgttttcgga ccc                     43

<210> SEQ ID NO 7
<211> LENGTH: 40
<212> TYPE: DNA
<213> ORGANISM: ARTIFICIAL
<220> FEATURE:
<223> OTHER INFORMATION: CLONING VECTOR

<400> SEQUENCE: 7
tccaattcgc cctatagtga gtcgtattac gcgcgctcac                         40
```

```
<210> SEQ ID NO 8
<211> LENGTH: 44
<212> TYPE: DNA
<213> ORGANISM: ARTIFICIAL
<220> FEATURE:
<223> OTHER INFORMATION: CLONING VECTOR

<400> SEQUENCE: 8
cacgaggtta agcgggatcc gatcgagcat aatgcgcgcg agtg            44
```

MICROLUMINOMETER CHIP AND METHOD TO MEASURE BIOLUMINESCENCE

The present application is a divisional application of U.S. patent application Ser. No. 09/660,581 filed Sep. 12, 2000, now U.S. Pat. No. 6,905,834 issued Jun. 14, 2005, said application being a continuation-in-part application of U.S. Ser. No. 08/978,439 filed Nov. 25, 1997, now U.S. Pat. No. 6,117,643 issued Sep. 12, 2000, the entire contents of which are specifically incorporated herein by reference in its entirety.

The United States government has rights in the present invention pursuant to grant number DE-FG05-94ER61870 from the Department of Energy and grant number F49620-89-C-0023 from the United States Air Force.

BACKGROUND OF THE INVENTION

1. Field of the Invention

Electronic circuitry may be used to detect a luminescent response. In particular, one may use an optical application specific integrated circuit (OASIC), which combines analog signal conditioning, digital signal processing, and wireless transmission with a sensitive electro-optical detector. To achieve maximum sensitivity to the luminescent response of a bioreporter, an OASIC should be sensitive to light in the 400 nm to 700 nm (visible) range, should have low leakage current and low noise, and should have minimal sensitivity to changes in environmental factors such as temperature and humidity. Such devices may be manufactured via a standard complimentary-metal-oxide-semiconductor (CMOS) process on a single substrate.

2. Description of Related Art

A bioluminescent bioreporter is an organism that is genetically engineered to produce light when a particular substance is metabolized. For example, bioluminescent (lux) transcriptional gene fusions may be used to develop light emitting reporter bacterial strains that are able to sense the presence, bioavailability, and biodegradation of organic chemical pollutants such as naphthalene, toluene, and isopropylbenzene. In general, the lux reporter genes are placed under regulatory control of inducible degradative operons maintained in native or vector plasmids or integrated into the chromosome of the host strain.

Due to the widespread use of petroleum products and the current regulations requiring underground storage tanks to be upgraded, replaced or closed by December 1998, the number of petroleum-contaminated sites has abounded. Of particular concern for drinking water quality are the more water-soluble components, benzene, toluene, ethylbenzene and xylenes (BTEX). Natural attenuation which relies on in situ biodegradation of pollutants has received a large amount of attention especially for petroleum contaminants. While microorganisms capable of biodegradation of BTEX compounds are usually present at these sites, there is a need to know whether or not conditions are favorable for biodegradation to occur.

Bioluminescent reporters have been widely used for the real time non-destructive monitoring of gene expression. Heitzer et al. (1992) developed a quantitative assay for naphthalene bioavailability and biodegradation using a nah-lux reporter strain HK44 constructed by King et al. (1990) containing a lux transposon (Tn4431) insertion in nahG of the lower naphthalene degradation operon. The nah-lux reporter was expanded for use as an on-line optical biosensor for application in groundwater monitoring (Heitzer et al., 1994). Other lux fusions have been constructed for monitoring the expression of catabolic genes including those for degradation of isopropylbenzene (Selifonova et al., 1996) and toluene (Applegate et al., 1997).

In addition to catabolic gene fusions, a wide variety of genes and operons have been studied using lux fusions. Lux fusions have been constructed for monitoring heat shock genes expression, oxidative stress, presence of Hg(II) and alginate production. In all these cases, the lux fusions are plasmid-based and were constructed by placing the promoter of interest in front of the promoterless lux genes from Vibrio fischeri contained in pUCD615 (Rogowsky et al., 1987).

3. Deficiencies in the Prior Art

A need has arisen for a monolithic bioelectronic device that contains both a bioreporter and an OASIC, yet is very small, rugged, inexpensive, low power, and wireless. (A monolithic bioelectronic device is a device that contains biological and electrical components and that is constructed on a single substrate layer.) Such a bioluminescent bioreporter integrated circuit (BBIC) could detect substances such as pollutants, explosives, and heavy-metals residing in inhospitable areas such as groundwater, industrial process vessels, and battlefields. Applications for such a device include environmental pollutant detection, oil exploration, drug discovery, industrial process control, and hazardous chemical monitoring. The low cost of such sensors and the wide variety of deployment methods would allow a large number of them to be distributed over a wide area for very comprehensive coverage.

SUMMARY OF THE INVENTION

The invention concerns analyte sensing devices comprising engineered bioluminescent bacteria placed on an integrated microluminometer. The bacteria are engineered to luminesce when a targeted compound is detected or metabolized. The microluminometer detects, processes, and measures the magnitude of the optical signal.

In certain embodiments, the invention discloses an apparatus for detecting the concentration of a selected substance or analyte in a sample. The apparatus generally comprises an integrated circuit that includes a phototransducer operative to generate a signal in response to light, a container for holding bioluminescent bacteria, and a substrate that is attached to the container and to the integrated circuit. The analyte concentration is related to the light signal.

Within the context of the present invention, bioluminescent bacteria may be referred to as bioreporters or bioreporter molecules because of their response to a selected analyte by expressing a luminescent lux gene product.

The apparatus may further comprise a layer of bioresistant/biocompatible material between the substrate and the container, such as a layer of silicon nitride. The integrated circuit is preferably a CMOS integrated circuit, and the phototransducer is preferably a photodiode. The integrated circuit may also include a current to frequency converter and/or a digital counter. Additionally, the integrated circuit may also include one or more transmitters. Such transmitters may be wireless, or conventionally wired. In other embodiments, the apparatus also includes a central data collection station capable of receiving transmissions from the transmitter.

The apparatus may also contain one or more fluid or nutrient reservoirs and one or more microfluidic pumps on the substrate to provide nutrient means for the bioreporter organisms utilized with the apparatus. An exemplary bioreporter is a genetically engineered bacterium, yeast, or animal cell.

The selectively permeable container may comprise a polymer matrix, which allows gas or fluid to reach the bioreporter. Preferably, the matrix is optically-clear. Optionally, the integrated circuit may contain a global positioning system (GPS). The BBIC may be prepared in a housing (e.g., injection molded plastic) that permits free passage of the gas or liquid, yet blocks ambient light. Such a housing may comprise a flat-black finish and a maze-like passage-way. The fluid or gas easily traverses the turns in the passageway, while the ambient light is greatly attenuated (due to the flat-black finish) at each turn.

An additional embodiment of the invention is an apparatus that detects a substance, such as a fluid comprising an integrated circuit including a phototransducer adapted to input an electrical signal into the circuit in response to light, a bioreporter that metabolizes the substance and emitting light consequent to such metabolism, the reporter adapted to contact the substance; and a transparent, biocompatible, and bioresistant separator positioned between the phototransducer and the bioreporter to enable light emitted from the bioreporter to strike the phototransducer. The bioreporter may be a bacterium, fungal, yeast, plant, or animal cell, or alternatively, a nucleotide sequence which encodes a luminescent reporter molecule. The apparatus may also comprise a plastic matrix encasing the bioreporter and enabling contact between the substance and the bioreporter. Such a matrix may be permeable to the substance.

Another aspect of the invention is an apparatus for detecting the concentration of a particular substance, comprising a substrate, a luminescent microorganism such as *Pseudomonas fluorescens* HK44 that metabolizes a selected substance to emit light; a selectively permeable container affixed to the substrate capable of holding the luminescent microorganism and which allows gas or fluid to reach the bioreporter, and prevents ambient light from reaching the bioreporter; a layer of semiconducting material such as silicon nitride between the substrate and the container; a fluid and nutrient reservoir and microfluidic pump on the substrate; a Complementary Metal Oxide Semiconductor (CMOS) integrated circuit on the substrate including a photodiode operative to generate a current in response to the light, a current to frequency converter, a digital counter, and wireless transmitter; and, a central data collection station capable of receiving transmissions from the transmitter.

Yet another aspect of the invention concerns a monolithic bioelectronic device for detecting a substance in a sample. This device generally comprises a bioreporter capable of metabolizing the substance and emitting light consequent to such metabolism; and, a sensor capable of generating an electrical signal in response to the reception of the emitted light. Such a device may also include a transparent, bioresistant and biocompatible separator positioned between the bioreporter and the sensor.

A standard integrated circuit (IC) is coated with a layer of insulating material such as silicon dioxide or silicon nitride. This process is called passivation and serves to protect the surface of the chip from moisture, contamination, and mechanical damage. Although this coating is adequate for general purpose chips, BBICs may be used in a variety of possibly harsh environments for which the standard passivation process is inadequate. For these purposes, BBICs require a second coating that must be biocompatible and bioresistant, must protect the OASIC from chemical stresses, must be optically tuned to efficiently transmit the light from the material under test, must adhere to an oxide coating, must be pin-hole free, and must be able to be patterned in order to form openings over the bonding pads and whatever structures that might be needed to maintain the bioreporter or collect a sample.

While the individual components of the invention described herein may be obtained and assembled individually, the inventors contemplate that, for convenience, the components of the biosensor may be packaged in kit form. Kits may comprise, in suitable container means, one or more bioreporters and an integrated circuit including a phototransducer. The kit may comprise a single container means that contains one or more bioreporters and the integrated circuit including a phototransducer. Alternatively, the kits of the invention may comprise distinct container means for each component. In such cases, one container would contain one or more bioreporters, either pre-encapsulated or encapsulated in an appropriate medium disclosed herein, and another container would include the integrated circuit. When the bioreporter is pre-encapsulated, the kit may contain one or more encapsulation media. The use of distinct container means for each component would allow for the modulation of various components of the kits. For example, several bioreporters may be available to chose from, depending on the substance one wishes to detect. By replacing the bioreporter, one may be able to utilize the remaining components of the kit for an entirely different purpose, thus allowing reuse of components.

The container means may be a container such as a vial, test tube, packet, sleeve, shrink-wrap, or other container means, into which the components of the kit may be placed. The bioreporter also may be aliquoted into smaller containers, should this be desired.

The kits of the present invention also may include a means for containing the individual containers in close confinement for commercial sale, such as, e.g., injection or blow-molded plastic containers into which the desired vials are retained.

Irrespective of the number of containers, the kits of the invention also may comprise, or be packaged with, an instrument for assisting with the placement of the bioreporter upon the integrated circuit. Such an instrument may be a syringe, pipette, forceps, or any other similar device.

In fact, virtually any suitable packaging and delivery of the required components are contemplated to be useful so long as the bioreporter remains functional. For example, long term storage of a bioreporter chip on a matrix such as alginate and a bacterial suspension may require refrigeration and prevention of desiccation for the organisms to remain viable.

The kit may comprise one or more distinct bioreporters and a single photodetector. For example, a kit for detecting naphthalene and toluene in a sample might comprise one bioreporter and a biofilm for detecting naphthalene and a distinct and/or separate biofilm for detecting toluene. The two biofilms may be applied sequentially to the sensor with each compound tested separately, or in certain circumstances, the biofilms may be applied in tandem to the chip and the compounds tested simultaneously. Various examples are given in FIG. 9A, FIG. 9B, FIG. 9C, and FIG. 9D. Several biofilms may be placed in an array as shown in FIG. 9A, allowing several different bioreporters to be tested simultaneously. The inventors contemplate that the number of distinct biofilms may be infinite, provided that the signal produced by a single individual biofilm is detectable by the photodetector. Alternatively, as shown in FIG. 9B, each distinct biofilm may be applied sequentially to the chip. Furthermore, as shown in FIG. 9C, several bioreporters may be mixed within one or more biofilms. Also, the biofilms may be layered as in FIG. 9D to allow several biofilms to be measured simultaneously.

In a certain particular embodiments, the invention includes biosensors for the detection of ammonia, generally determined as ammonium ion. In such examples, a bioreporter microorganism is situated close to the surface of an integrated circuit chip, generally in a semipermeable container or matrix, so that in the presence of an ammonium ion, the microorganism produces a luminescent protein that emits light related to the amount of ammonium ion present. The microorganism is engineered to include lux genes stably integrated into the chromosome which are controlled by promoters responsive to ammonia. Examples are the hau or amo promoters, although it is contemplated that other promoters responsive to ammonia or ammonium ion are also suitable. Exemplary lux genes are the CDABC lux gene fusions that can be prepared for example from lux genes of bacteria such as *Vibrio fischeri*.

Exemplary bacteria into which the lux gene construct may be introduced include *E. coli, Salmonella, Mycobacter tuberculosis, Listeria, Photobacter phosphoreum* or *Vibrio fischeri*.

The invention also includes expression vectors comprising lux CDABE genes operatively linked to a promoter induced by ammonia or ammonia ion, cells transformed by such vectors and any of a number of apparatus comprising the described biosensor. Additionally, the invention is also intended to include methods for detecting ammonia using the biosensor and apparatus described and kits including the biosensors. Such kits will include instructions for use as well as optional materials such as standards for preparing standard curves.

A further exemplary biosensor has been designed to detect estrogens and xenoestrogens for use in eukaryotic cells such as yeast.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 9A, FIG. 9B, FIG. 9C and FIG. 9D show conceptual diagrams depicting methods of utilizing multiple bioreporters. Different bioreporters are symbolized by A, B, C, etc.

FIG. 9A shows a biofilm separated into a number of discreet sections with each section comprising a different bioreporter.

FIG. 9B shows a number of biofilms, each comprising a different bioreporter.

FIG. 9C shows multiple bioreporters combined within a single biofilm.

FIG. 9D shows a biofilm comprising several discreet layers with each layer comprising a different bioreporter.

FIG. 29A shows response due to induction with simple solution, SS.

FIG. 29B shows response due to induction with complex solution, CS.

FIG. 30A shows uptake following induction with SS.

FIG. 30B shows uptake following induction with CS.

DESCRIPTION OF ILLUSTRATIVE EMBODIMENTS

The preferred embodiments of the present invention are illustrated in FIGS. 1-32 of the drawings, like numerals being used to refer to like and corresponding parts of the various drawings.

Genetically engineered bioluminescent bacteria are encapsulated and placed on a specially designed integrated circuit. The bacteria are designed to bioluminesce after metabolizing a targeted analyte, while the integrated circuit is designed to detect the luminescence, process this signal, and report the results. Exemplary bioreporters are described including one for the sensing ammonia and another for estrogens. Methods for adhering these bioreporters to integrated circuits within encapsulation matrices are described as well as several design features of the integrated circuit that improve performance and sensitivity.

Overview of the System

A photodiode is integrated into a semiconductor substrate along with signal processing electronics and either data storage electronics, electronics for transmission of the measured data via a hard-wired communication network or wireless communication electronics for remote read-out of the data. Key elements of the micro-luminometer system are a photodiode compatible with the semiconductor process employed to fabricate the accompanying electronics, novel low-noise electronics for the detection of low-level photosignals in the presence of electronic noise and communications electronics (wired or wireless) to transmit the data to a data processing and storage system.

Figure 1:
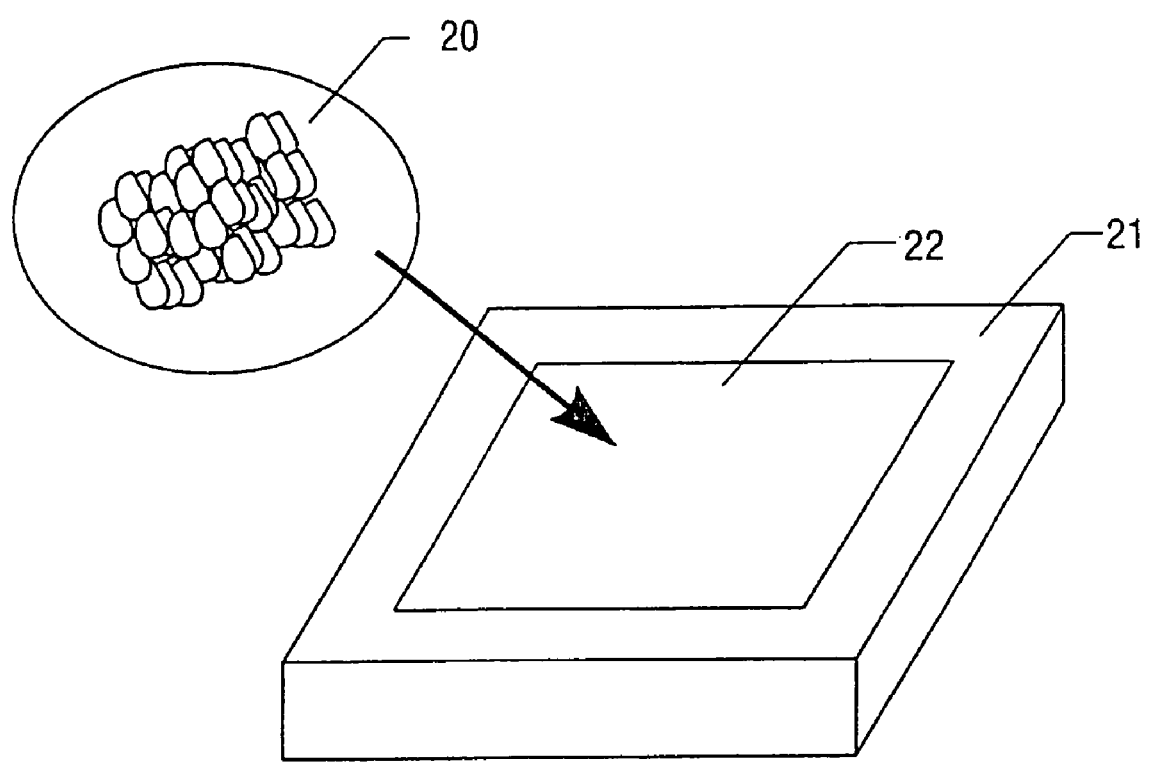
FIG. 1 shows a perspective view of one embodiment of the present invention.

FIG. 1 shows a perspective view of the present invention. The substance 20 that is being detected enters the BBIC 21 through the polymer matrix 22. Once the substance is detected, the BBIC transmits a signal indicating the concentration of the substance to a central location.

Figure 6:
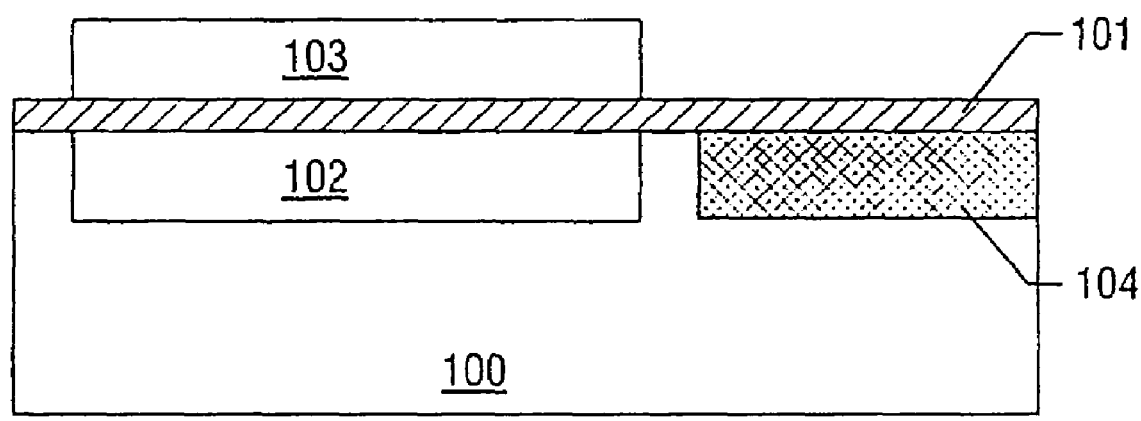
FIG. 6 shows a side view of one embodiment of the present invention.

FIG. 6 shows a side view of the present invention. The bioreporter is enclosed in polymer matrix 103, which is separated from a photodetector 102 by a protective coating 101. A single substrate 100 contains these elements as well as additional circuitry 104 that processes and transmits the signal.

Figure 3A:
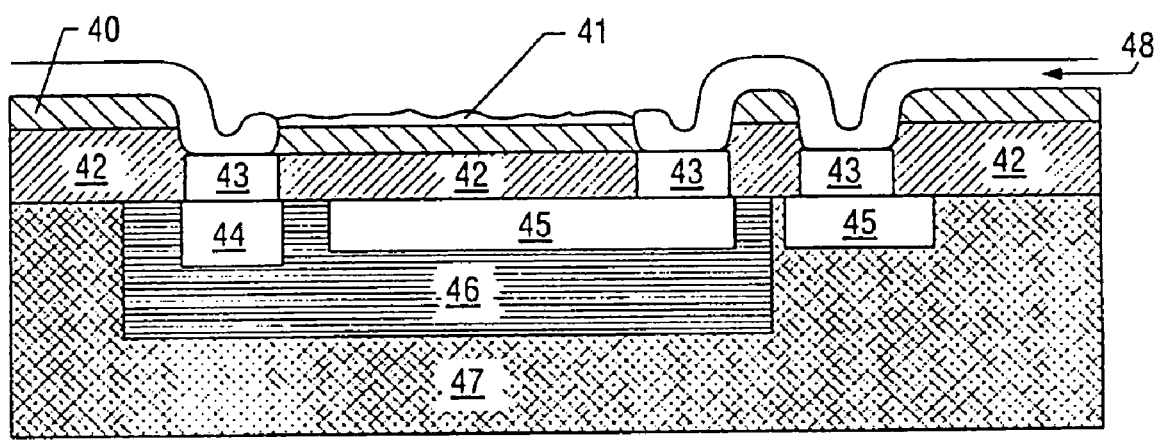
FIG. 3A shows a high-quality photodetector that can be made using a standard N-well CMOS process.

FIG. 3A shows a high-quality photodetector made using a standard N-well CMOS process. The photodetector consists of two reverse biased diodes in parallel. The top diode is formed between the P+ active layer 45 and the N-well 46, and the bottom diode is formed between the N-well 46 and the P-substrate 47. The top diode has good short wavelength light sensitivity (400-550 nm), while the bottom diode provides good long wavelength sensitivity (500-1100 nm). Thus, the complete diode is sensitive over the range from 400 to 1100 nm. The luminescent compound under test 41 is separated from the photodetector by a layer 40 of $Si_3N_4$ and a layer 42 of $SiO_2$.

Figure 4:
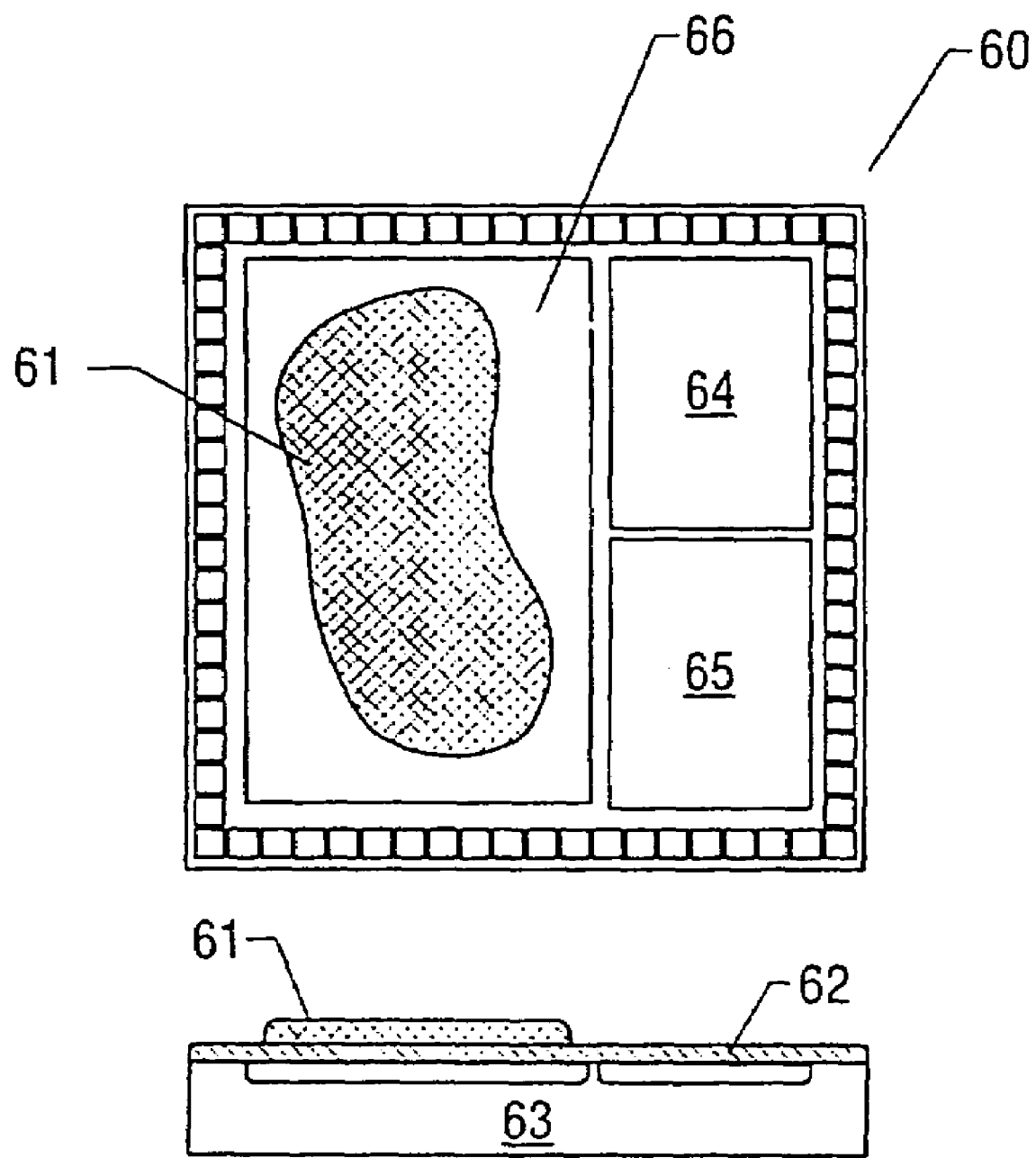
FIG. 4 shows the photodetector in FIG. 1 together with associated signal conditioning and processing circuitry on a single integrated circuit.

FIG. 4 shows the photodetector 66 in FIG. 1 coupled with signal conditioning 65 and processing circuitry 64 on a single integrated circuit 60. The purpose of the analog signal conditioning circuitry is to amplify and filter the relatively small photodetector signal so that it can be compared to a threshold, digitized, or modulated for transmission. While the effects of wideband noise can be reduced by integration of the signal, integration has a much weaker effect on 1/f noise. The effect of low frequency noise can be reduced by using correlated double sampling (CDS) in which two samples are taken within a short interval of time such that one sample consists of signal and noise and the other sample consists only of noise. The low frequency component of the noise is greatly attenuated in the difference of these two samples.

When the targeted substance reaches the bioreporter, it is metabolized and the bioreporter emits light with a wavelength of from between about 400 and about 700 nm (in the visible range). The bioreporter is encased in a polymer matrix that keeps the bioreporter positioned over the photodetector, allows the gas or fluid being sampled to reach the bioreporter, and allows the emitted light to reach the photodetector.

Figure 5:
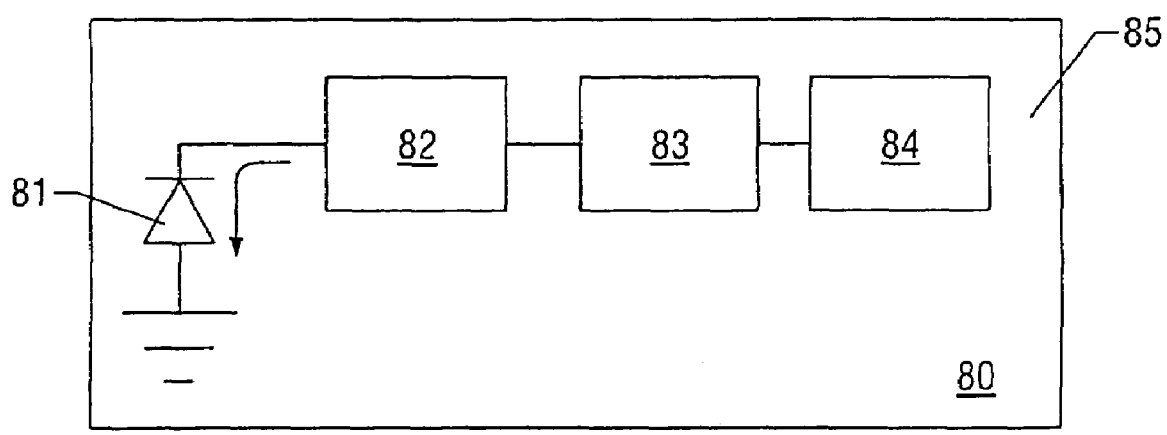
FIG. 5 shows a block diagram of one possible embodiment of the signal processing portion of the present invention.

A block diagram showing one possible embodiment of the signal processing portion of the present invention is shown in FIG. 5. The photodetector in FIG. 3A is a photodiode 81 that responds to light by conducting a current to the ground. A current to frequency converter 82 converts this current into a sequence of pulses that are counted by a digital counter 83. The number of pulses counted in a fixed period of time is directly proportional to the amount of light collected by the photodiode, which in turn is directly proportional to the concentration of the targeted substance. A wireless transmitter 84 then relays this measured concentration 85 to a central data collection station.

Figure 8:
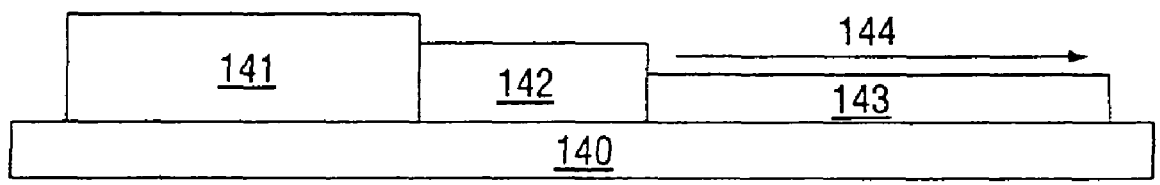
FIG. 8 shows a bioreporter being supplied with water and nutrients.

FIG. 8 shows the bioreporter being supplied with water and nutrients. A fluid and nutrient reservoir 141 is connected to a microfluidic pump 142 so that nutrient and fluid 144 may flow through the polymer matrix 143 enclosing the bioreporter. Each of these components can be constructed on a single substrate 140.

Figure 2:
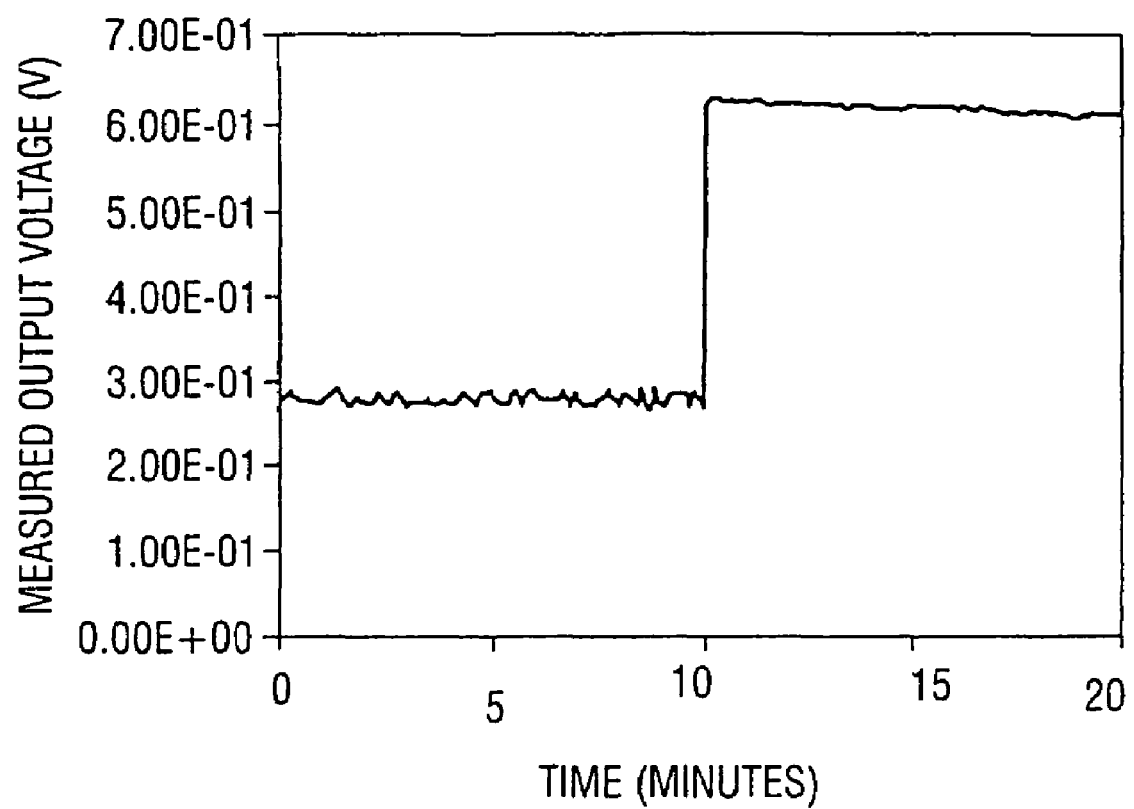
FIG. 2 Shows the measured signal that resulted from a test of a prototype of the present invention.

A prototype device was constructed by coupling *P. fluorescens* HK44, a naphthalene bioreporter, to an OASIC. The resulting device was exposed to naphthalene. The measured signal is shown in FIG. 2. The background reading is indicated from 0 to 10 min, and the reading during induced bioluminescence is shown from 10 to 20 min.

Additional circuitry may be included in the BBIC as required. For example, a BBIC may contain a Global Positioning Satellite system for determining the location of the sensor.

Photodetector

The first element in the micro-luminometer signal processing chain is the photodetector. The key requirements of the photodetector are:

Sensitivity to wavelength of light emitted by the bioluminescent or chemiluminescent compound under test;

Low background signal (i.e., leakage current) due to parasitic reverse biased diodes;

Appropriate coating to prevent the materials in the semiconductor devices from interfering with the bioluminescent or chemiluminescent process under study and to prevent the process under study from degrading the performance of the micro-luminometer; and, Compatibility with the fabrication process used to create the microluminometer circuitry.

Two photodetector configurations that satisfy these requirements are described below. It should be understood, however, that alternative methods of constructing such a photodetector may be used by one skilled in the art without departing from the spirit and scope of the invention as defined in the claims.

In the first embodiment, the photodetector is fabricated in a standard N-well CMOS process. Shown in FIG. 3A, this detector is formed by connecting the PN junction between the PMOS active region and the N-well in parallel with the PN junction between the N-well and the P-type substrate. The resulting detector is sensitive to light between about 400 nm and about 1100 nm, a range that encompasses the 450-600 nm emission range of most commonly used bioluminescent and chemiluminescent compounds or organisms. In order to meet the requirement that the device have a low background signal, the device is operated with a zero bias, setting the operating voltage of the diode equal to the substrate voltage. The photodiode coating may be formed with a deposited silicon nitride layer or other material compatible with semiconductor processing techniques.

In the second photodetector embodiment, the detector is fabricated in a silicon-on-insulator (SOI) CMOS process. The internal leakage current in an SOI process is two to three orders of magnitude lower than in standard CMOS due to the presence of a buried oxide insulating layer between the active layer and the substrate. Two photodetector structures are envisioned in the SOI process. The first structure, shown on the left of FIG. 3B, consists of a lateral PIN detector where the P-layer is formed by the P+ contact layer, the I (intrinsic) region is formed by the lightly doped active layer, and the N region is formed by the N+ contact layer of the SOI CMOS process. The spectral sensitivity of this lateral detector is set by the thickness of the active layer, which may be tuned for specific bioluminescent and chemiluminescent compounds.

Figure 3B:
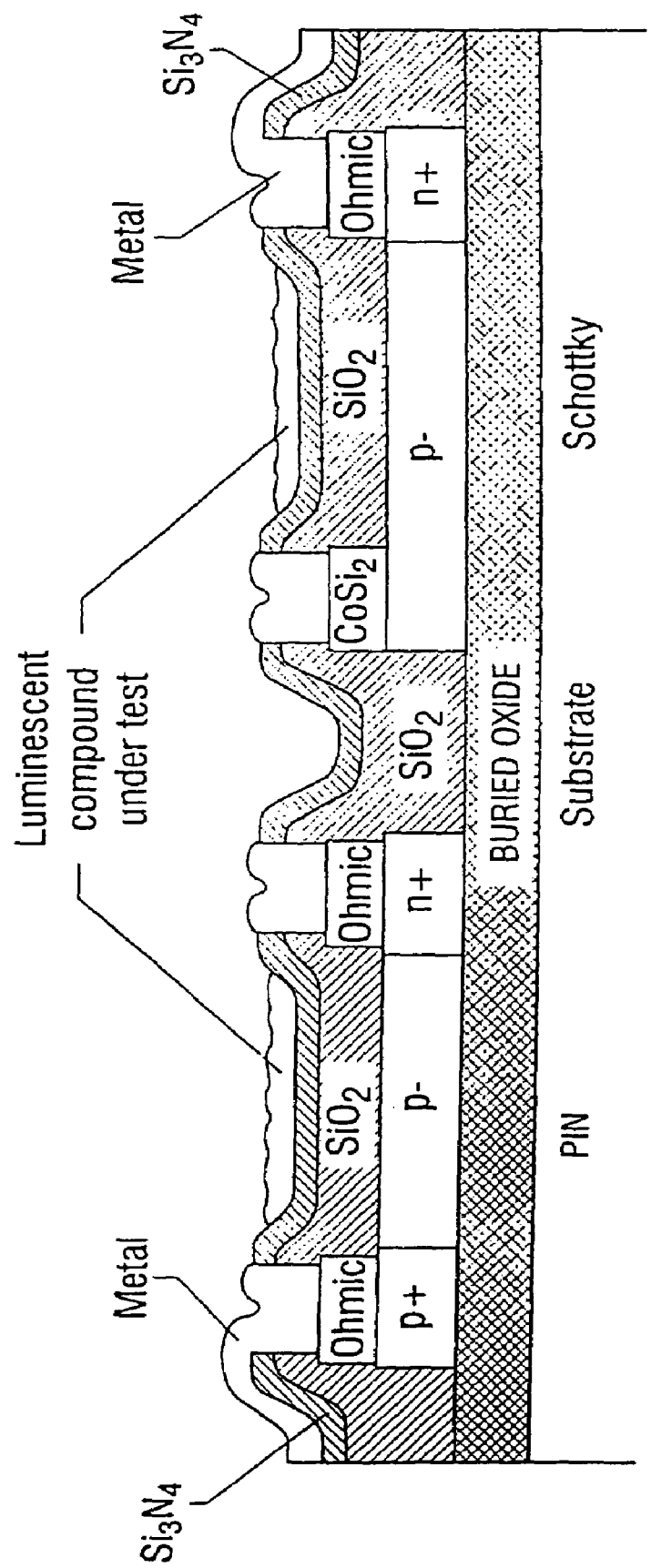
FIG. 3B shows two photodetector structures fabricated in a silicon-on-insulator CMOS process: on the left, a lateral PIN detector; on the right a device similar to left except that the junction is formed with a Schottky junction.

The second structure, shown on the right side of FIG. 3B, is similar to the first except that the junction is formed with a Schottky junction between a deposited cobalt silicide ($CoSi_2$) or other appropriate material layer and the lightly doped active layer.

The inventors contemplate that other photodetector configurations may be envisioned in silicon or other semiconductor processes meeting the criteria set forth above.

Low Noise Electronics

The low noise electronics are the second element in the micro-luminometer signal processing chain. The requirements for the low noise electronics are:

Sensitivity to very low signal levels provided by the photodetector;

Immunity to or compensation for electronic noise in the signal processing chain;

Minimum sensitivity to variations in temperature;

Minimum sensitivity to changes in power supply voltages (for battery powered applications);

For some applications the electronics must have sufficient linearity and dynamic range to accurately record the detected signal level; and, In other applications the electronics must simply detect the presence of a signal even in the presence of electronic and environmental noise.

Three embodiments that satisfy these requirements are considered below. It should be understood, however, that alternative methods of detecting small signals while satisfying these requirements can be used without departing from the spirit and scope of the invention as defined in the claims.

Figure 7A:
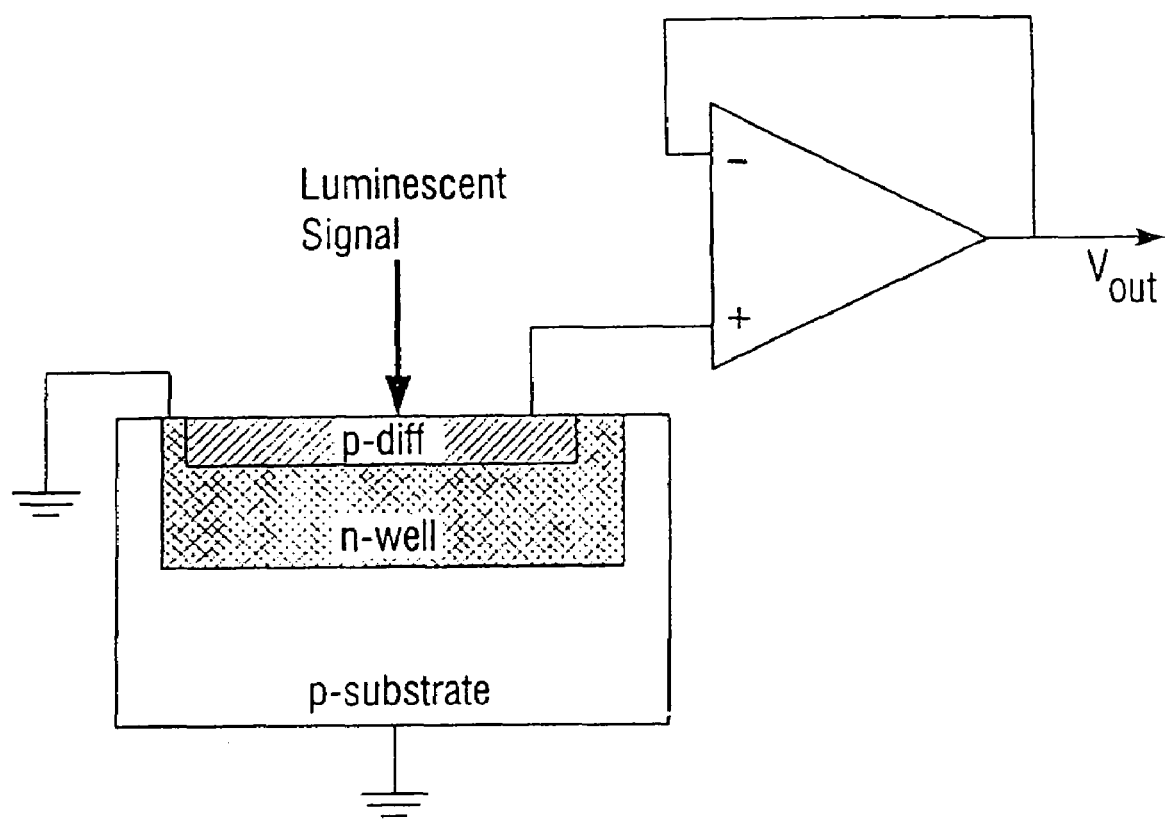
FIG. 7A shows a simple photodiode consisting of a P-diffusion layer, an N-well, and a P-substrate.

FIG. 7A schematically shows the first approach to the detection of very small signals. This device uses a P-diffusion/N-well photodiode, a structure compatible with standard CMOS IC processes, in the open circuit mode with a read-out amplifier (fabricated on the same IC with the photodiode). The luminescent signal generates electron-hole pairs in the P-diffusion and the N-well. The photo-generated electrons in the P-diffusion are injected into the N-well, while the photo-generated holes in the N-well are injected into the P-diffusion. The N-well is tied to ground potential so that no charge builds up in this region. However, since the P-diffusion is only attached to the input impedance of a CMOS amplifier (which approaches infinity at low frequencies), a positive charge collects in this region. Thus, the voltage on the P-diffusion node begins to rise.

As the P-diffusion voltage begins to rise, the P-diffusion/N-well photodiode becomes forward biased, thereby producing a current in a direction opposite to the photo-generated current. The system reaches steady state when the voltage on the P-diffusion node creates a forward bias current exactly equal in magnitude (but opposite in polarity) to the photo-current. If this PN junction has no deviations from the ideal diode equation, then the output voltage is $$V_{out} = V_t \ln(I_p/(A\, I_s) + 1), \tag{1}$$

where $V_t$ is the thermal voltage (approximately 26 mV at room temperature), $I_p$ is the photo-current, A is the cross-sectional area of this PN junction, and $I_s$ is the reverse saturation current for a PN junction with unit cross-sectional area. The value of $I_s$ depends greatly on the IC process and material parameters.

Two major error currents are present in PN junctions operating at low current density: recombination current and generation current. Except at very low temperatures, free carriers are randomly created in the PN junction space charge region. Since this region has a high field, these thermally excited carriers are immediately swept across the junction and form a current component (generation current) in the same direction as the photocurrent. Carriers crossing the space-charge region also have a finite chance of recombining. This creates another current component (recombination current) in the opposite direction of the photocurrent. Therefore, taking into account these error currents, equation (1) becomes $$V_{Out}=V_t \ln((I_p+I_g-I_r)/(A I_s)+1) \qquad (2)$$

This output voltage is a function of parameters that are generally beyond our control. However, we do have control over the junction area, A. Unfortunately, to make our output signal larger, we want a small A, while we want a large A for a high quantum efficiency (QE).

Figure 7B:
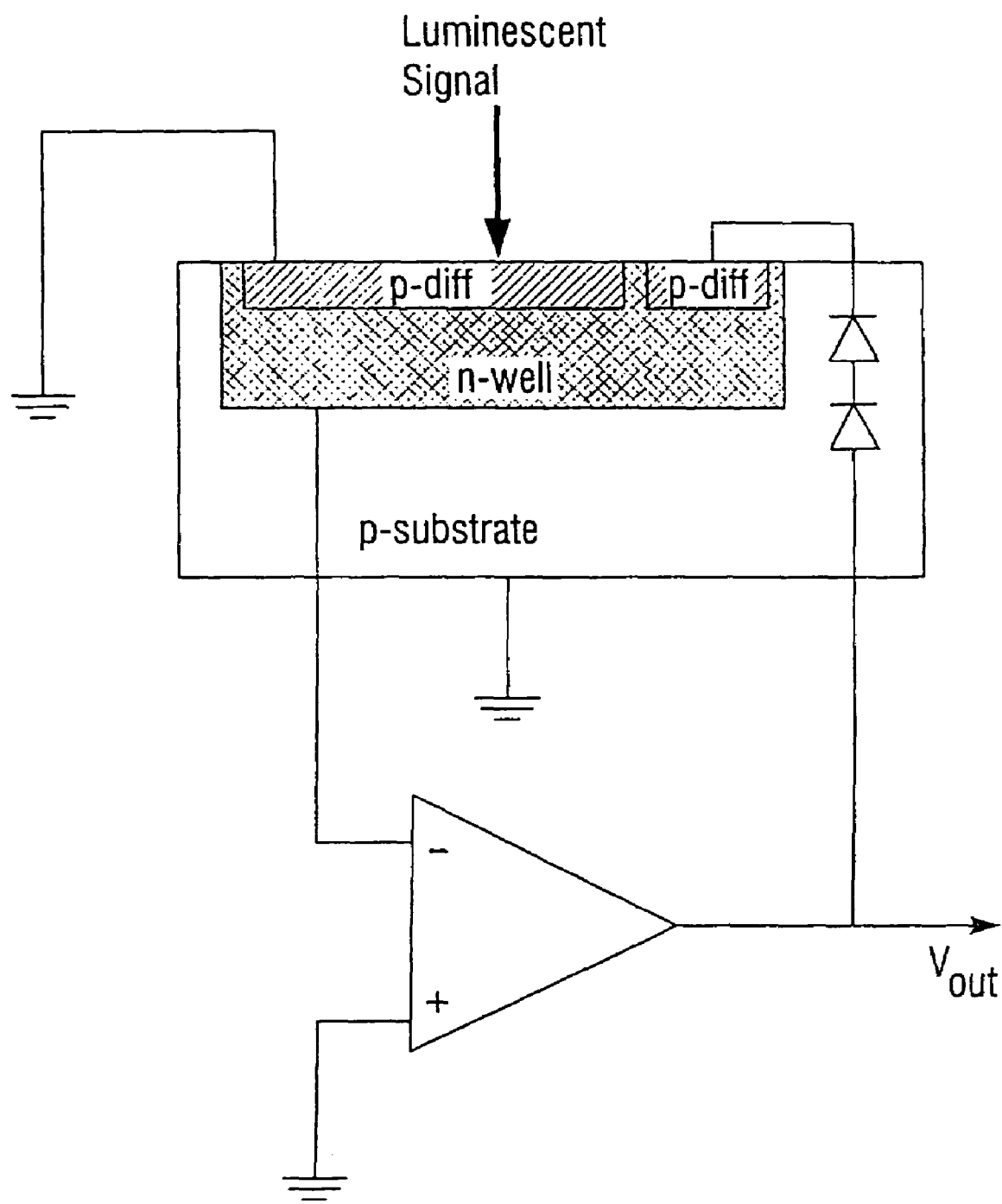
FIG. 7B shows a circuit using a large area photodiode for efficient light collection, and a small-area diode in a feedback loop to supply the forward bias current that cancels out the photo-current.

FIG. 7B shows a second microluminometer embodiment that satisfies both of these needs. This circuit uses a large area photodiode for efficient light collection, but uses a small-area diode in a feedback loop to supply the forward bias current that cancels out the photo-current. Once again, the amplifier and feedback diodes are fabricated on the same IC as the photodiode. For this circuit, $$V_{out}=3 V_t \ln((I_p+I_g-I_r)/(A_{fb}I_s)+1), \qquad (3)$$

where $A_{fb}$ is the small cross-sectional area of the feedback diode. More than one diode is used in the feedback path to make the output signal large compared to the DC offset of any subsequent amplifier stages. This technique allows efficient collection of the light with a large-area photodiode, yet produces a large output voltage because of the small-area diodes in the feedback path.

The feedback circuit of FIG. 7B maintains the photodiode at zero bias. With no applied potential, the recombination and generation currents should cancel. Equation (3) becomes $$V_{out}=3 V_t \ln((I_p/(A_{fb}I_s))+1) \qquad (4)$$

if the smaller recombination and generation currents in the smaller feedback diodes are neglected.

The principal advantages of the second micro-luminometer embodiment shown in FIG. 7B are:

The SNR is totally determined by the photodiode. Noise from the small diode and amplifier are negligible;

Diodes can be added in the feedback path until the signal level at the output of the amplifier is significant compared to offset voltages (and offset voltage drift) of subsequent stages;

This method is completely compatible with standard CMOS processes with no additional masks, materials, or fabrication steps;

This detection scheme can be fabricated on the same IC with analog and digital signal processing circuits and RF communication circuits; and, Measurement can be made without power applied to the circuit. Power must be applied before the measurement can be read, but the measurement can be obtained with no power.

Figure 7C:
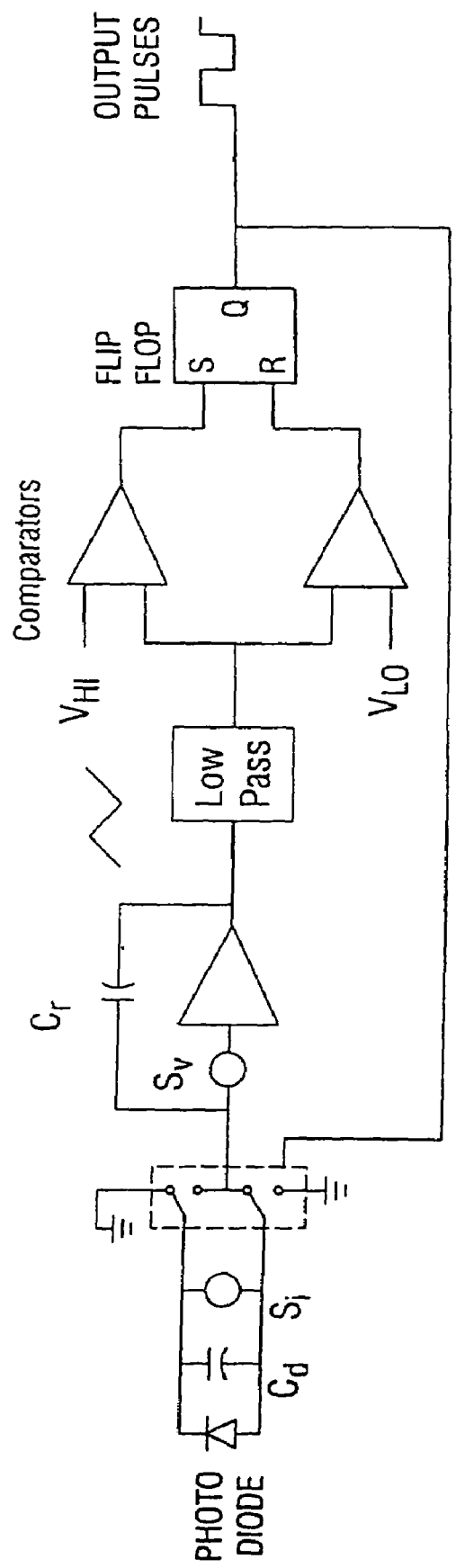
FIG. 7C shows a circuit using correlated double sampling (CDS) to minimize the effects of low frequency (flicker) amplifier noise as well as time or temperature dependent variations in the amplifier offset voltage.

A third micro-luminometer implementation shown in FIG. 7C uses correlated double sampling (CDS) to minimize the effects of low frequency (flicker) amplifier noise as well as time or temperature dependent variations in the amplifier offset voltage. As shown in FIG. 7C, a photodiode with capacitance $C_d$ and noise power spectral density $S_i$ is connected to an integrating preamplifier with feedback capacitance $C_f$ and input noise power spectral density $S_v$ through a set of switches that are controlled by the logical level of a flip-flop output. When the flip-flop output is low, the switches are positioned so that the photocurrent flows out of the preamplifier, causing the output voltage of the integrator to increase. When the low-pass filtered integrator output voltage exceeds a threshold, $V_{HI}$, the upper comparator "fires," setting the flip-flop and causing its output to go high. The detector switches change positions, causing current to flow into the integrating amplifier, which in turn causes the amplifier output voltage to decrease. When the integrator output goes below a second threshold, $V_{LO}$, the lower comparator "fires," resetting the flip-flop and causing the output to go low again. The process repeats itself as long as a photocurrent is present.

The average period of the output pulse, Δt, is given by $$\Delta t = \frac{2C_f(V_{HI}-V_{LO})}{I_p}, \qquad (5)$$

where $V_{HI}$ and $V_{LO}$ are the threshold voltages of the comparators and $I_p$ is the diode photocurrent. Two noise sources contribute to error in the measured value of Δt. $S_i$ is the input noise current power spectral density associated primarily with the photodiode, and $S_v$ is the input noise voltage power spectral density associated primarily with the preamplifier. The diode noise is given by $$S_i = 2q(2I_s+I_p)\left(\frac{A^2}{Hz}\right), \qquad (6)$$

where $I_s$ is the photodiode reverse saturation current and $I_p$ is the photocurrent. As the photocurrent approaches zero, the noise power spectral density approaches a finite value of $4qI_s$ A²/Hz. The noise voltage $S_v$ of the preamplifier is determined by its design and has units of V²/Hz.

The transfer function from the point where the diode noise is introduced to the output of the integrator is given approximately by $$H_i(\omega) \approx \left(\frac{1}{sC_f}\right)\left(\frac{\omega_1}{s+\omega_1}\right), \qquad (7)$$

where $\omega_1$ is the corner frequency of the integrating amplifier and s=j$\omega$. Ignoring for the moment the effect of the switches, the transfer function from the point where the amplifier noise is introduced to the output of the integrator is given approximately by $$H_v(\omega) \approx \left(\frac{C_f+C_d}{C_f}\right)\left(\frac{\omega_1}{s+\omega_1}\right), \qquad (8)$$

The switches perform a correlated double sampling function which attenuates the noise which appears below the switching frequency of the output pulse string. The transfer function of a correlated double sampling circuit is approximated to first order by the expression $$H(\omega) \approx \left(\frac{s}{s+2/\Delta t}\right), \qquad (9)$$

where Δt is the average period of the output pulse string. Thus, taking into account the switches, the transfer function from the point where the amplifier noise is introduced to the output of the integrator is approximately given by $$H_v(\omega) \approx \left(\frac{C_f + C_d}{C_f}\right)\left(\frac{\omega_1}{s+\omega_1}\right)\left(\frac{s}{s+2/\Delta t}\right). \quad (10)$$

This is an important result because the effective zero introduced in the noise voltage transfer function reduces the effect of the flicker noise of the amplifier. This is particularly useful in CMOS implementations of the micro-luminometer where flicker noise can have a dominant effect.

The mean squared output noise at the output of the integrator is $$v_n^2 = \int_{-\infty}^{\infty} S_v(H_v * H_v) + S_i(H_i * H_i) d\omega, \quad (11)$$

and the RMS noise voltage is then given by $$\sigma_v = \sqrt{v_n^2}. \quad (12)$$

The RMS error in the measured period is determined by the slope of the integrated signal and the noise at the output of the integrator following the relationship $$\sigma_t = \frac{\sigma_v}{\frac{dv}{dt}} \quad (13)$$

or, approximately, $$\sigma_t \approx \frac{\sigma_v}{\frac{(V_{HI} - V_{LO})}{\Delta t}}. \quad (14)$$

The error in measuring $\Delta t$ may be reduced by collecting many output pulses and obtaining an average period. The error in the measured average pulse period improves proportionately to the square root of the number of pulses collected, such that $$\overline{\sigma}_t \approx \frac{\sigma_v}{\frac{(V_{HI} - V_{LO})}{\Delta t}} \frac{1}{\sqrt{N}} \quad (15)$$

or $$\overline{\sigma}_t \approx \frac{\sigma_v}{\frac{(V_{HI} - V_{LO})}{\Delta t}} \sqrt{\frac{t_{meas}}{\Delta t}} \quad (16)$$

where $t_{meas}$ is the total measurement time.

Thus, implementation of the micro-luminometer has the following advantages:

The low frequency "flicker" noise of the amplifier is reduced by a correlated double sampling process; and, Ideally, the accuracy of the measured photocurrent may be improved without limit by acquiring data for increasing periods of time.

Of course, practical limitations imposed by the lifetime and stability of the signals produced by the luminescent compound under test will ultimately determine the resolution of this implementation.

Read-Out Electronics

Several methods of reading out the data from the microluminometer may be used. These include:

Generation of a DC voltage level proportional to the photocurrent;

Generation of a DC current level proportional to the photocurrent;

Generation of a logical pulse string whose rate is proportional to the photocurrent;

On-chip implementation of an analog to digital converter that reports a numerical value proportional to the photocurrent;

On-chip implementation of a serial or parallel communications port that reports a number proportional to the photocurrent;

Implementation of an on-chip wireless communication system that reports the value of the photocurrent;

Generation of a logical flag when the photocurrent exceeds a predefined level; and, Generation of a radio-frequency signal or beacon when the photocurrent exceeds a predefined level.

Biosensors for Chemical and Biological Agents

A BBIC requires integration of the appropriate bioreporters, a cell entrapment method, an integrated microluminometer, and a viocompatible/bioresistant protective coating for the integrated chip.

Luminometry

Luminometry is an analytical technique that uses chemiluminescence or bioluminescence to detect the presence and concentration of a particular substance, condition, or organism. Luminescent assays provide one of the most important and widely used analytical tools now in use. For example, luciferase bioluminescence assays are used to quantify the amount of adenosine triphosphate (ATP) present in samples. This type of measurement indicates the presence or absence of small numbers of microbes, and is useful for environmental toxin detection/quantification, water quality measurements, as well as many other applications. Similar bioluminescent techniques have been used to study gene expression (Bronstein, et al., 1994), detect heavy metal and organic environmental pollutants (Applegate, et al., 1996), medical diagnostics or bioluminescent assays for research in auditory neuroscience studies (Wangemann, 1996).

Luminometry is often the analytical technique of choice due to its high sensitivity and is routinely used to detect picogram levels of ATP. There is no requirement for an excitation source, and no radioactive materials are involved. Luminescence is typically measured by bench-top luminometers which use photomultiplier tubes (PMTs), microchannel plates, or films as detection devices. While extremely sensitive, these devices are limited to laboratory use because of size, fragility, and cost. Applications that require in situ, in vivo, in vitro, or a large number of distributed or parallel measurements are not well served by present state-of-the-art luminometers. There is a need to make luminescence-based assays rugged and inexpensive tools that operate in a variety of environments outside the laboratory.

Attributes of the integrated CMOS microluminometer include minimum detectable signal (MDS) and immunity from false signals generated by thermally induced leakage current variations. These attributes are determined by the material characteristics, biasing, and front-end signal processing of the CMOS photodiodes used to detect the luminescence.

CMOS Microluminometer Design

Figure 36:
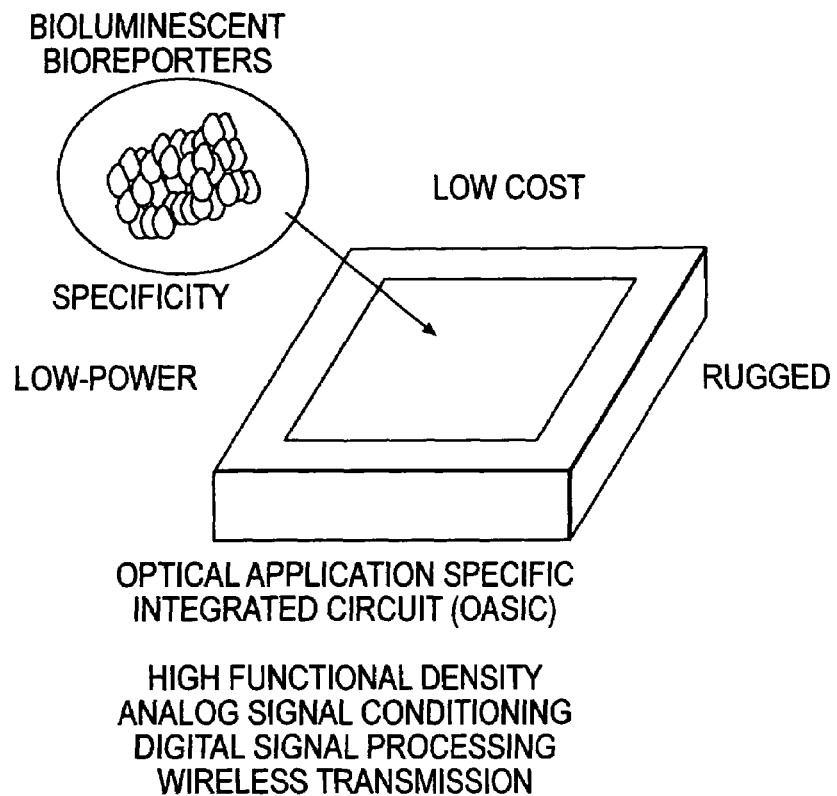
FIG. 36 shows a bioluminescent bioreporter integrated circuit formed by placing genetically-engineered bioluminescent cells on an optically-sensitive integrated circuit (IC). The molecular specificity is provided by the cells, while the IC provides the advantages of a microelectronic format.
Figure 37:
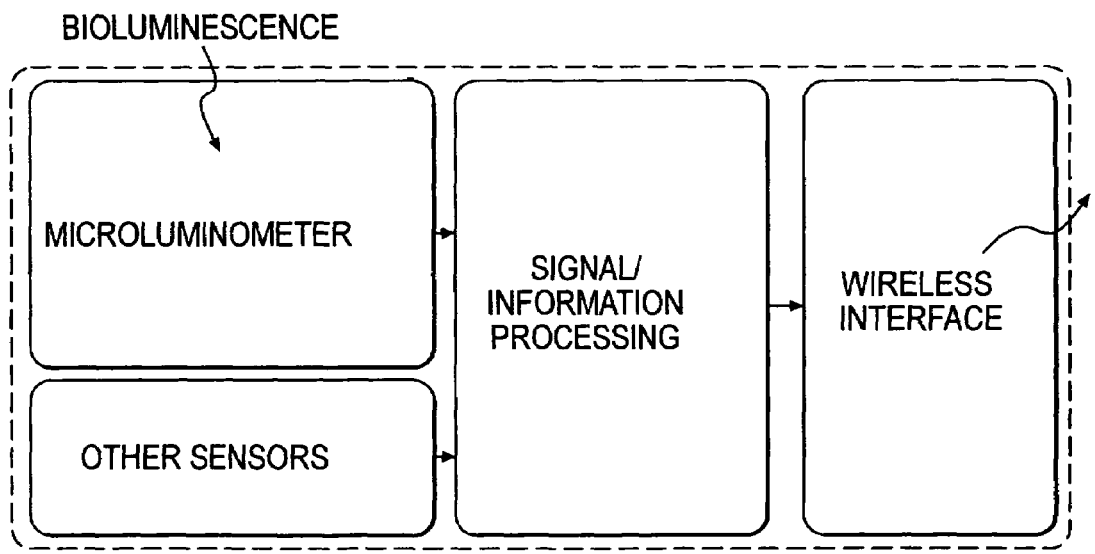
FIG. 37 shows a BBIC with a microluminometer for detecting bioluminescence and other integrated sensors (e.g. temperature sensor), information processing circuitry, and wireless telemetry.

Applications for BBICs include environmental monitoring, food and water quality testing, in vivo sensors for disease detection and management, and other remote applications where size, power consumption, and cable plant concerns are the dominant issues. Therefore, the integrated circuit (IC) portion of the BBIC should reside on a single chip, be compatible with battery operation, and be compatible with RF circuits for wireless telemetry in addition to allowing the integration of high-quality photodiodes and low-noise analog signal processing. FIG. 36 shows a bioluminescent bioreporter integrated circuit formed by placing genetically-engineered bioluminescent cells on an optically sensitive integrated circuit (IC). The molecular specificity is provided by the cells, while the IC provides the advantages of a microelectronic format. FIG. 37 shows a block diagram of one embodiment of the IC portion of a BBIC.

A standard 0.5-μm bulk CMOS process that meets optical and signal processing requirements, while allowing the realization of RF circuits operating in the 916-MHz band may be used. The design and performance of the two major components of the microluminometer; the CMOS photodiodes and the front-end signal processing, are described.

An integrated CMOS microluminometer for the detection of low-level bioluminescence in whole-cell biosensing applications has been developed. The microluminometer is the microelectronic portion of the bioluminescent bioreporter integrated circuit (BBIC). This device uses the n-well/p-substrate junction of a standard bulk CMOS IC process to form the integrated photodetector. The photodetector uses a distributed electrode configuration that minimizes detector noise. Signal processing is accomplished with a current-to-frequency converter circuit that forms the causal portion of the matched filter for dc luminescence in wide-band white noise. Measurements show that luminescence can be detected from as few as $4 \times 10^5$ cells/mL.

Size, power consumption, and cable plant concerns are important in many applications. Ideally, the integrated circuit (IC) portion of the BBIC resides on a single chip, is compatible with battery operation, and allows flexible communications with central data collection stations in addition to accommodating the integration of high-quality photodiodes and low-noise analog signal processing. A standard 0.5-μm bulk CMOS process that meets optical and signal processing requirements was selected which provided the desired size and power attributes. The design and performance of the two major components of the microluminometer: the CMOS photodiodes and the front-end signal processing are described.

CMOS Photodiodes

CMOS technology allows the realization of phototransistors, photodiodes, and photogates without any modification or additions to the standard processing steps. As normally used, these devices have broad spectral responsivities that peak in the red/near infrared region. Peak external quantum efficiency of 50%-80% has been reported for CMOS photodiodes (Kramer, et al., 1992).

Figure 38:
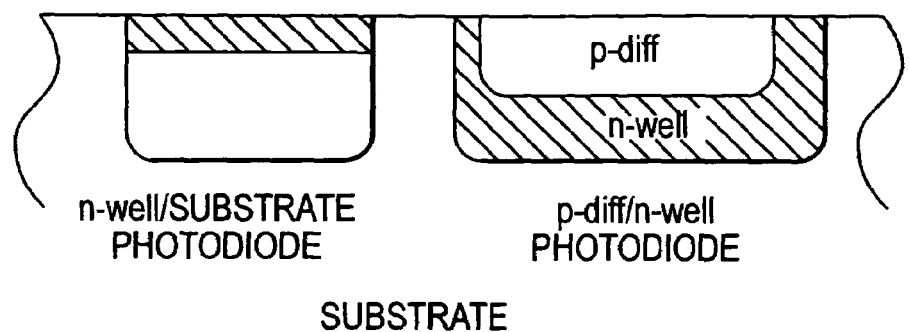
FIG. 38 shows two of the semiconductor junctions available for photodiode realization in bulk, n-well, CMOS IC processes. An n-well/substrate junction provides higher quantum efficiency.

FIG. 38 shows two junctions are available for the realization of CMOS photodiodes in standard CMOS processes: p-diff/n-well and n-well/substrate. The shallower junction (p-diff/n-well) would seem to be the most attractive for this application since its response peaks near the 490-nm wavelength of the bioluminescence, yet drops off quickly at longer wavelengths (Simpson, et al., 1998).

The quantum efficiency of p-diff/n-well photodiodes in small geometry CMOS processes is low (typically less than 10%). One explanation is that the shorter drive-in diffusion step for small geometry processes is insufficient to anneal the lattice damage created by the ion implantation step, thereby leaving a high density of charge traps in these diffusions. In this case, the large number of charge carrier traps severely degrades the quantum efficiency in the blue and green optical regimes. Regardless of the mechanism, the p-diff/n-well junction is not suitable for low-level luminescence detection, prompting selection of the n-well/substrate photodiode for the microluminometer transducer.

Figure 39:
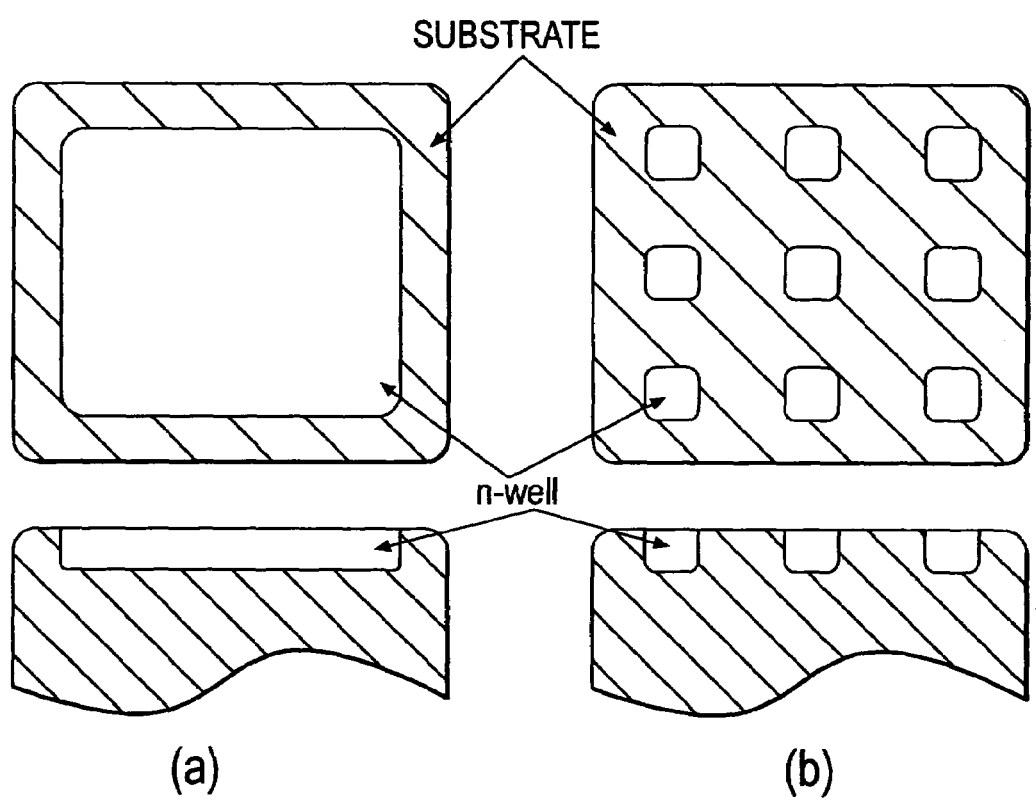
FIG. 39 shows two photodiode electrode configurations: (a) the n-well electrode covers most of the active area of the photodiode; and (b) distributed n-well electrodes reduce leakage current and detector capacitance with an insignificant effect on the quantum efficiency.

The physical layout of the electrodes affects both the quantum efficiency and the reverse leakage current of the photodiode. Two possible electrode configurations are shown in FIG. 39. In the first configuration, the n-well electrode covered the entire active region of the photodiode. The advantage of this approach is that all photo-generated charge is produced in the n-well and must only diffuse a short distance to the n-well/substrate junction without being trapped to produce a photocurrent.

Figure 40:
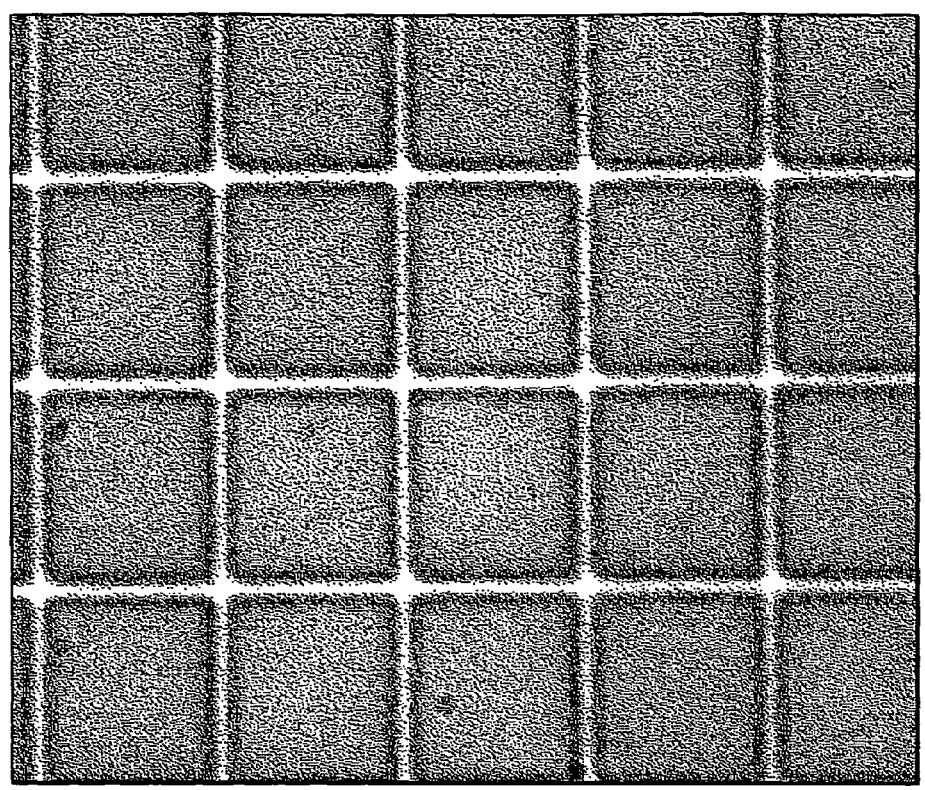
FIG. 40 illustrates a typical photodiode electrode configuration for BBIC applications. The n-wells are 5.6 μm×5.6 μm and the center-to-center spacing is 12.6 μm. The wiring grid above the Si surface is shown. Connection to the n-well electrodes is made at the intersection of the vertical and horizontal wires.

The second approach employs an array of small n-well/substrate junctions spread across the active region of the detector. This approach minimizes the degradation of noise performance caused by detector capacitance and leakage current. However, in this configuration charge created in the substrate regions must diffuse a relatively long distance without being trapped to produce a photocurrent. In principle one could calculate the optimum spacing between electrodes given a detailed knowledge of material parameters such as the diffusion length and the surface recombination velocity. These parameters may vary from run to run so that empirical determination of optimum spacing may be preferred. As an example, an initial choice of 5.6 μm×5.6 μm electrodes spaced 12.6 μm apart (~20% coverage) was made as shown in FIG. 40.

For use with bioluminescent bioreporters, it is desirable to minimize the photodiode reverse leakage current for two reasons. First, the power spectral density of the detector white noise depends directly on the magnitude of the dc leakage current. Possibly more important is the inability to distinguish a low-level dc luminescent signal from a dc leakage current. Variations in the leakage current as a function of temperature cannot be distinguished from a change in the bioluminescence. Conventional solutions, such as chopping the optical signal, are not practical for this integrated, single-chip, analytical instrument. The ideal diode equation, $$I_f = I_s \left( e^{\frac{V_f}{V_T}} - 1 \right) \tag{17}$$

where
 $I_f$=forward current
 $I_s$=reverse saturation current
 $V_f$=forward bias
 $V_T$=thermal voltage (≈26 mV@room temperature)

describes two competing current components: 1) electrons/holes on the n/p side overcoming the potential barrier;

$$I_f = I_s e^{\frac{V_f}{V_T}}, \tag{18}$$

and 2) holes/electrons on the n/p side diffusing to the edge of the space charge region and being swept across $$I_r = -I_s. \tag{19}$$

At zero bias these two components are in dc equilibrium, so the dc leakage current is zero. However, these currents are uncorrelated, so their noise power spectral densities (PSD) add. This simple analysis predicts that the noise PSD at zero bias is higher than it is at any reverse bias.

Unfortunately, the situation is not that simple. Equation (17) describes moderate to strong forward bias current. However, at weak forward bias or in reverse bias, equation (17) underpredicts the magnitude of the current because of surface and generation/recombination effects. $I_r$, as well as $I_f$, will depend on bias, and it is not certain at what bias level the minimum noise is found. However, zero bias is certainly where the minimum dc leakage current is found, and therefore the greatest immunity from thermally generated false signals.

Figure 41:
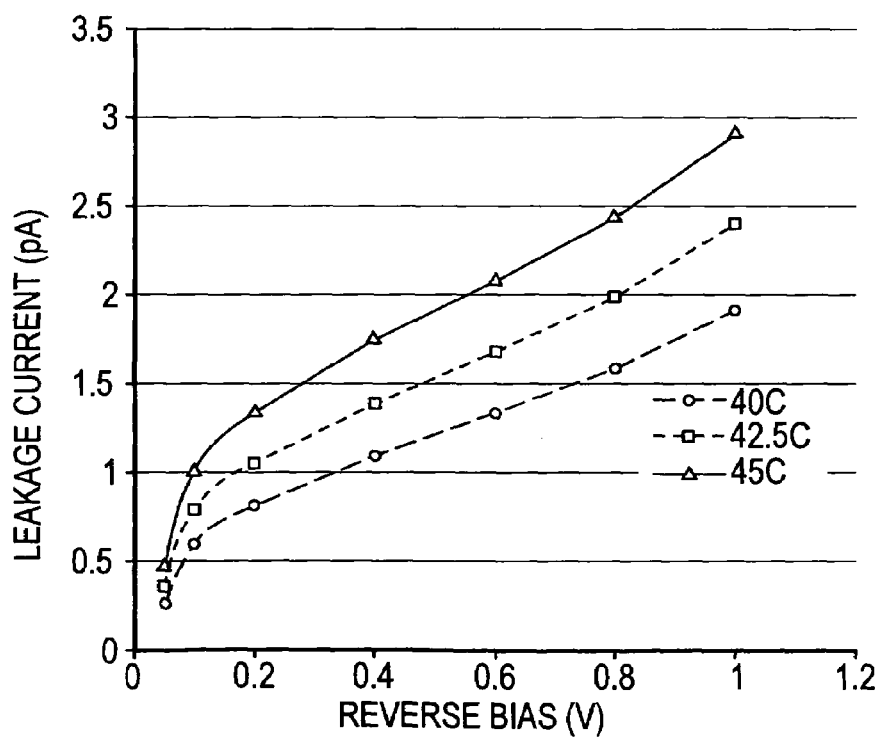
FIG. 41 is a graph showing reverse leakage current vs. reverse bias at 40° C., 42.5° C., and 45° C. for the photodiode of FIG. 40 illustrating the advantage of operating the photodiode at low reverse bias.
Figure 42:
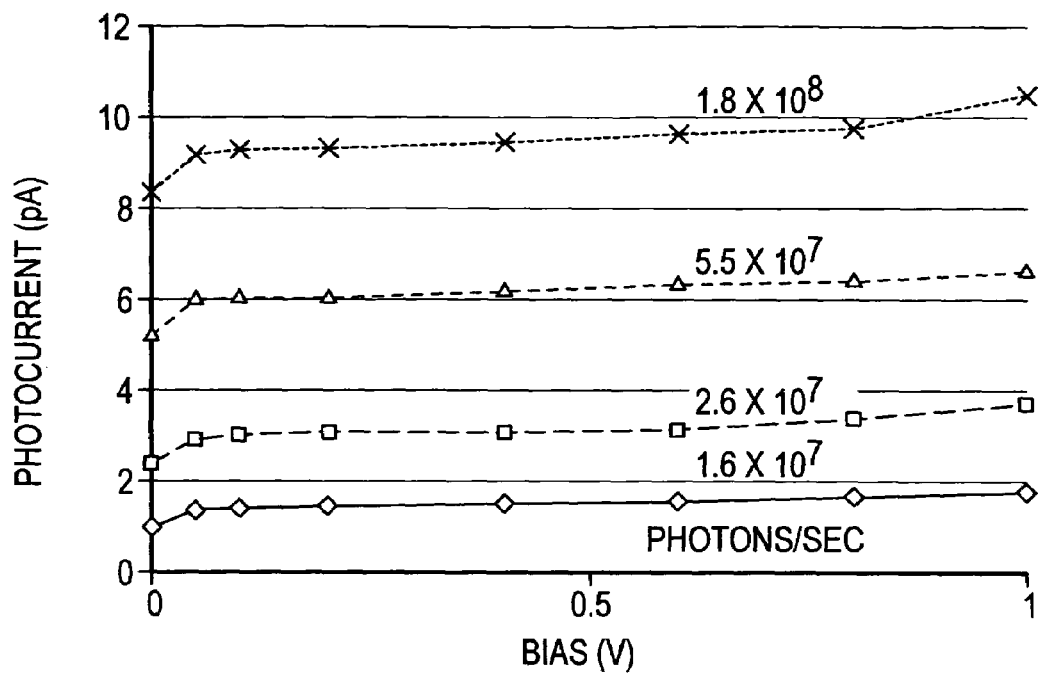
FIG. 42 is a graph of photocurrent vs. reverse bias at input fluxes of $1.6 \times 10^7$, $2.6 \times 10^7$, $5.5 \times 10^7$, and $1.8 \times 10^8$ photons/sec. illustrating that the quantum efficiency is only slightly influenced by the magnitude of the reverse bias above 50 mV.

FIG. 41 shows the reverse leakage current vs. bias for the photodiode of FIG. 40 at three different temperatures. This figure clearly shows that operating at reduced bias greatly reduces the magnitude of the temperature drift of the leakage current. FIG. 42 shows the measured photodiode signal (minimum input flux=$1.6 \times 10^7$ photons/second, wavelength=490 nm) vs. reverse bias for the photodetector shown in FIG. 40. This figure demonstrates that the quantum efficiency has a weak dependence on bias for reverse biases above 50 mV. In addition, this figure shows the quantum efficiency of this detector to be ~70% at 490 nm at 1.75 pA photocurrent for an input flux of 1.6×photons/sec, which indicates that the spacing between n-well electrodes can be increased, thereby further decreasing leakage current and detector capacitance.

Signal Processing

Figure 43:
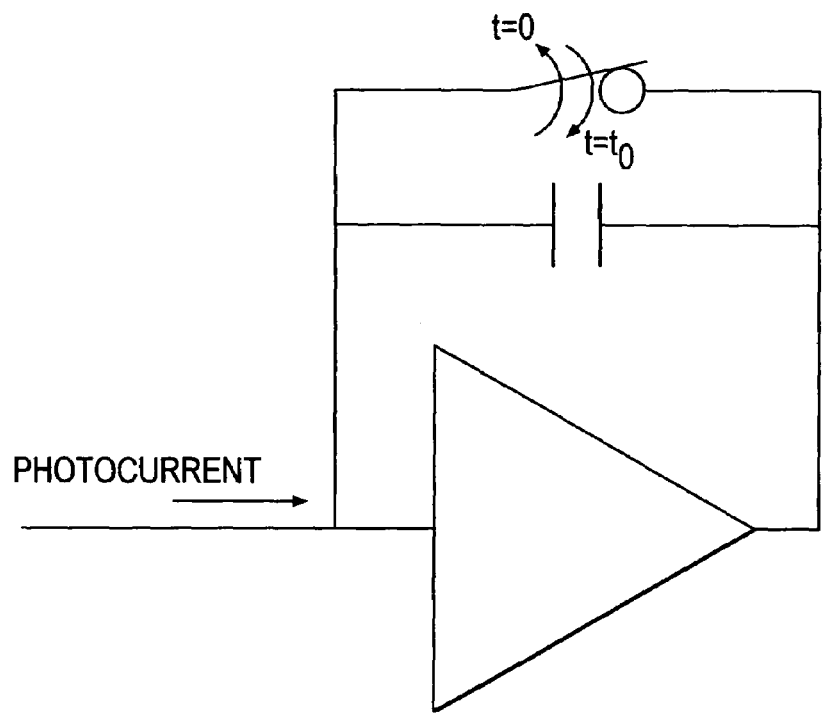
FIG. 43 shows a gated integrator that integrates the photocurrent from $0 \leq t \leq t_0$ forms the causal portion of the matched filter for dc luminescence in wide-band white noise.

The simplest noise approximation for the microluminometer assumes the detection of a dc signal in wide band white noise. If the input signal x(t) is approximated as a step function u(t), then the impulse response of the matched filter is:

$$h_{opt}(t) = ku(t_0 - t), \qquad (20)$$

where k is a constant and $t_0$ is the time of the measurement. The optimal impulse response has an output at negative infinity for an impulse input at t=0, and is therefore non-causal and non-realizable. However, the causal portion of the filter can be realized as a gated integrator with the gate open for $0 < t < t_0$ (FIG. 43).

The noise at the output of a gated integrator due to white detector current noise at the input is:

$$\overline{v_{no}^2} = \frac{\overline{i_n^2} t_0}{2C_f^2}, \qquad (21)$$

where
$\overline{v_{no}^2}$ = mean square output voltage noise
$\overline{i_n^2}$ = mean square photodiode current noise
$C_f$ = integrator feedback capacitor, while $$v_0^2(t_0) = \frac{i_p^2 t_0^2}{C_f^2}, \qquad (22)$$

where
$v_o^2(t_o)$ = output signal power at $t_0$
$i_p$ = photocurrent.

From equations (22) and (23) the signal-to-noise ration (SNR) is:

$$SNR = \frac{2i_p^2 t_0}{\overline{i_n^2}}, \qquad (23)$$

and continues to improve as $t_o$ increases.

Figure 44:
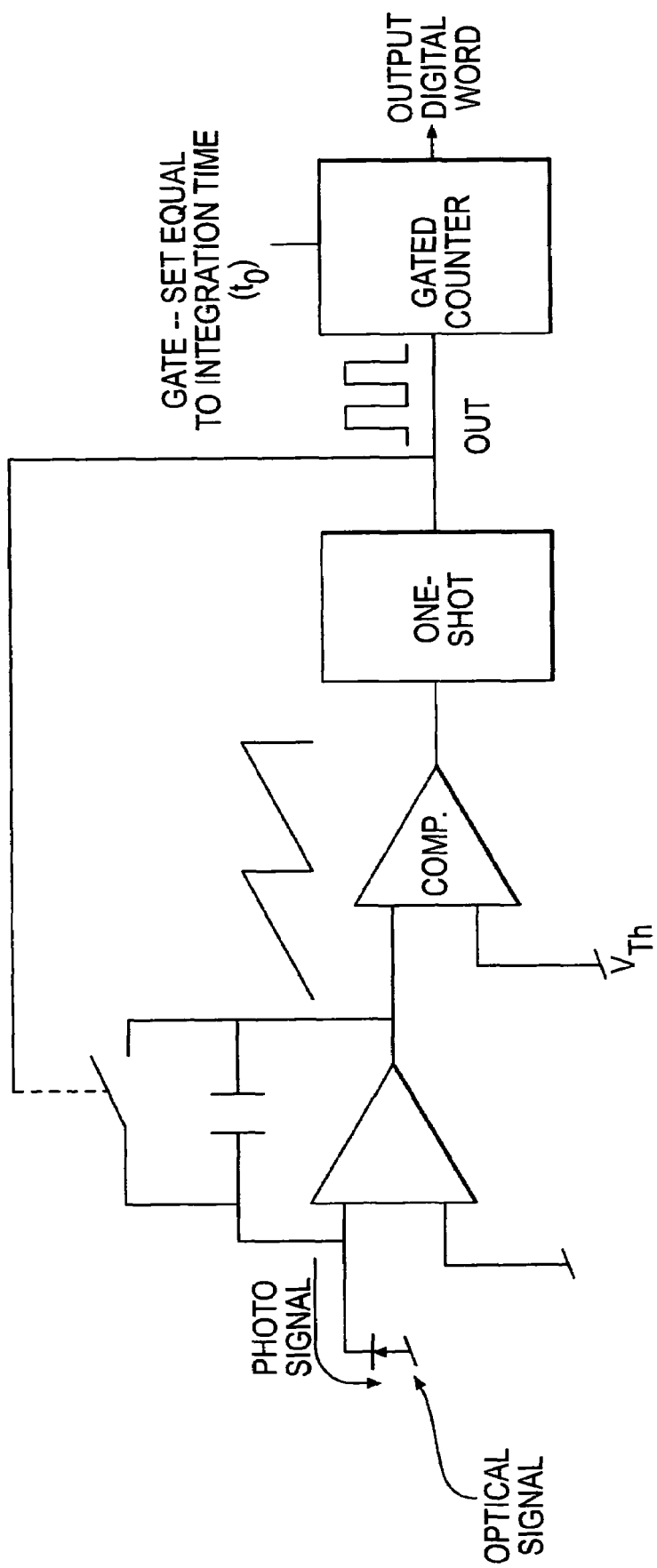
FIG. 44 shows a current-to-frequency converter used to form the long time-constant integrator.

Practical concerns generally limit $t_0$ to several minutes. A remaining problem is capacitor values that are too large for on-chip implementation. This was solved by using a hybrid analog/digital integration scheme as shown in FIG. 44. In this circuit, an analog integrator and a discriminator convert the photodiode current into a train of digital pulses (current-to-frequency converter (CFC)). These pulses are counted for a fixed time ($t_0$), and the result is a digital word that is proportional to the photocurrent. This scheme has several advantages compared to other processing options including fast recovery from overload and ease of analog-to digital conversion. It has been reported as useful in optical detection systems (deGraff and Wolffenbuttel, 1997).

Integrated CMOS Microluminometer

Figure 45:
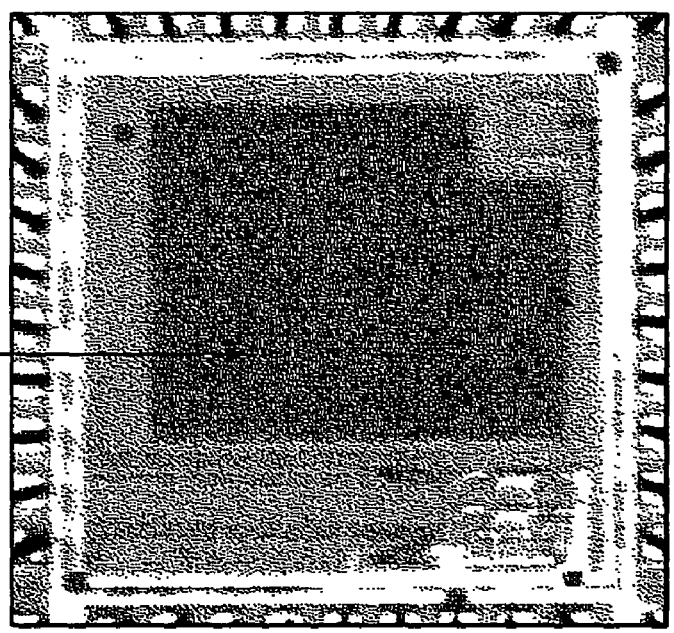
FIG. 45 shows a microluminometer that measures 2.2 mm×2.2 mm.

The disclosed sensors provide the basis for creating wholly self contained biosensors that require no exogenous reagents beyond what can be provided on the IC so that the IC can function independently of any other instrumental component Microluminometer Chip FIG. 45 shows a photograph of the complete microluminometer chip. The chip measures 2.2 mm×2.2 mm with the photodetector occupying ~25% (1.2 mm$^2$—although the total active region of the photodiode may be much larger) of the total chip area. For testing purposes the chip was mounted in a 40-pin ceramic dual inline package.

Nutrient Delivery System

Figure 21:
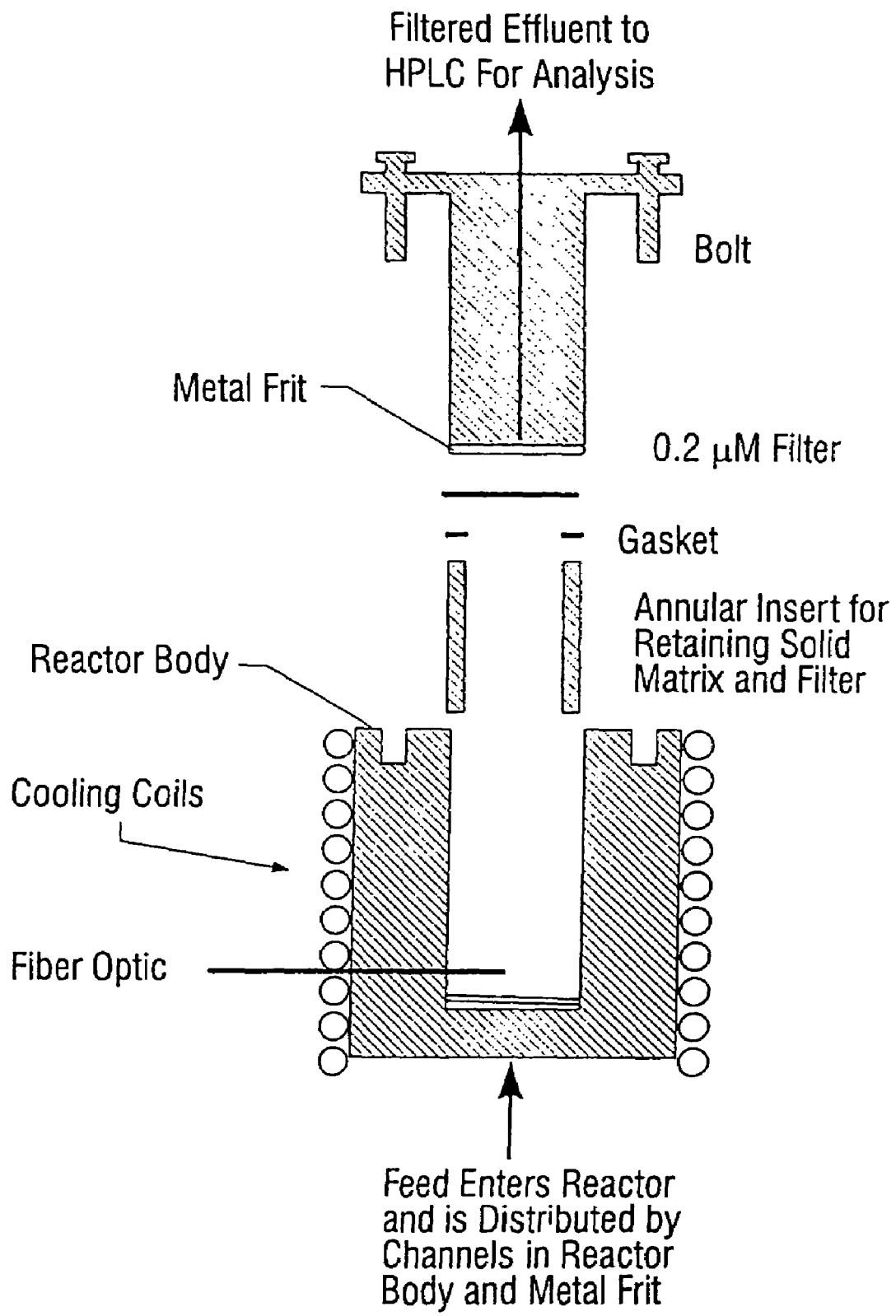
FIG. 21 shows exploded, cutaway diagram of the reactor. Feed is distributed to the reactor cavity filled with cells immobilized in small alginate beads by channels etched in the reactor body and by the attached metal flit. An annular insert holds the 0.2 μM hydrophobic filter against the top metal flit with the effect of providing a significant uniform resistance to flow and providing a clean effluent for automatic injection into the HPLC. The resistance to flow caused by the filter was typically 50 psig for a clean filter.

FIG. 21 illustrates one method of providing nutrients to the living bioreporters on BBICs. The concept has three main components:
a fluid and nutrient reservoir;
a microfluidic pump; and,
a BBIC.

The fluid and nutrient reservoir and microfluidic pump on a different substrate than the BBIC may be easier to implement. However, an implementation that places all three components on the same monolithic substrate could also be used.

The reservoir is simply a container that holds water with the appropriate nutrients in solution. This can be implemented on-chip by depositing a thick oxide over the fluidic area of the chip and defining a reservoir space by photolithographic methods. To increase the volume of such an implementation, an external container (e.g., a plastic pipette tip) may be attached to the on-chip reservoir with an appropriate epoxy.

Microfluidic pumps have been realized in numerous manners including peristaltic pumps, conducting polymer pumps, and electro-osmotic pumps. For an on-chip pump, an electro-osmotic pump is most compatible. This device consists of a capillary that has been etched into the Si and then coated with a thermally-grown oxide. A top plate is required for proper pump operation. Polydimethylsiloxane (PDMS), sold under the brand name Sylgard 184, (Dow Corning) may be used to coat the top plate. Glass or quartz slides may also be used to form the top plate. The capillary could be tens of microns wide and tens of microns in depth. The length can be several centimeters, but on a BBIC would likely be on the order of a few mm. To activate the pump, a voltage is placed across the capillary. In capillary electrophoresis applications, voltages as high as 1 kV are required for rapid separations. However, in this application, we would expect operation at only a few volts.

A gravity pump could be also be used where the floor of the capillary is at a slant. The end of the capillary that supplies the fluid to the bioreporters could be restricted to regulate the flow of fluid or an actuator (e.g., a microcantilever) could gate fluid flow. In practice, any pump that is small, low power, and can operate from low voltages could be used either on-chip or on a separate substrate.

Bioluminescence Detection

Figure 46:
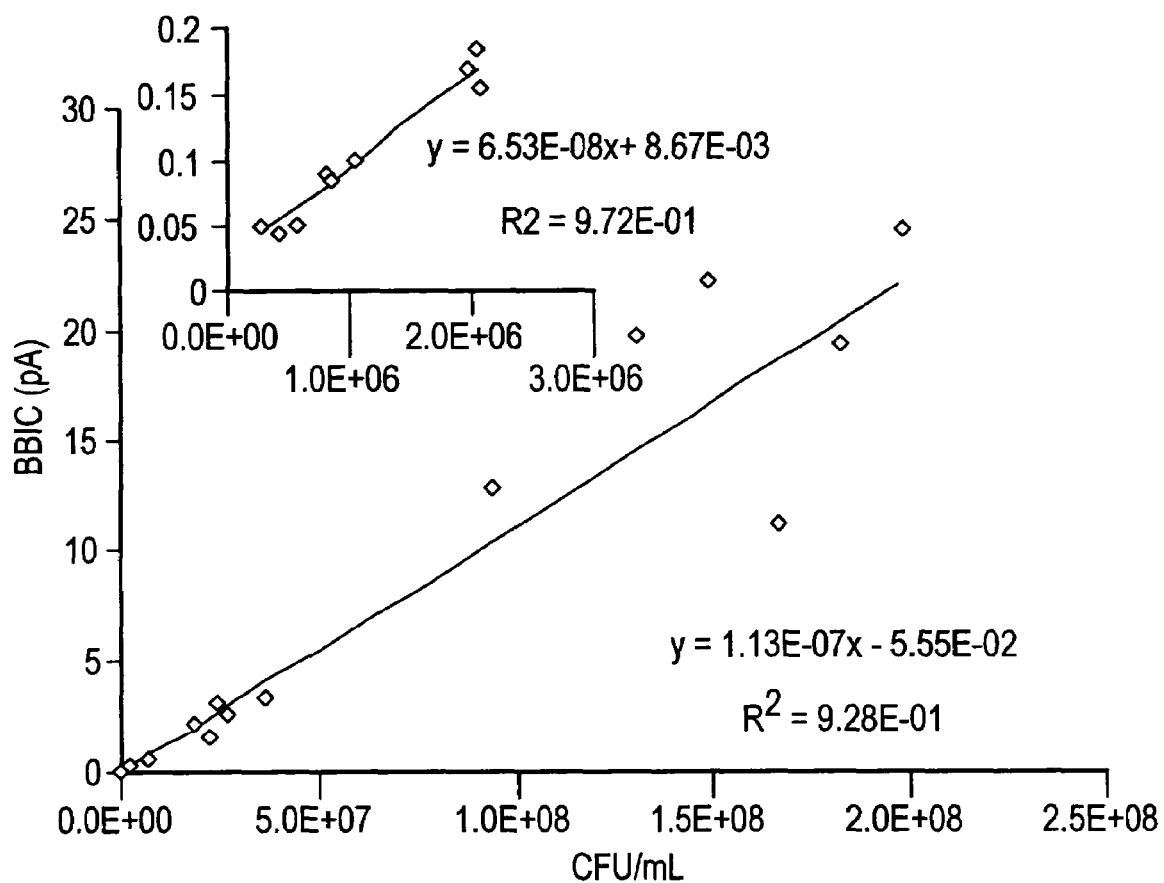
FIG. 46 shows the bioluminescence response for a culture containing various concentrations of *P. fluorescens* 5RL cells. Bioluminescence was determined using the integrated circuit luminometer and a light-tight enclosure mounted above the chip. Linear regression analysis showed that the data fit a linear model indicating that bioluminescence per cell remains constant. Using this linear model, the limit of detection for this experimental configuration was calculated to be $4 \times 10^5$ cells per mL.
Figure 47:
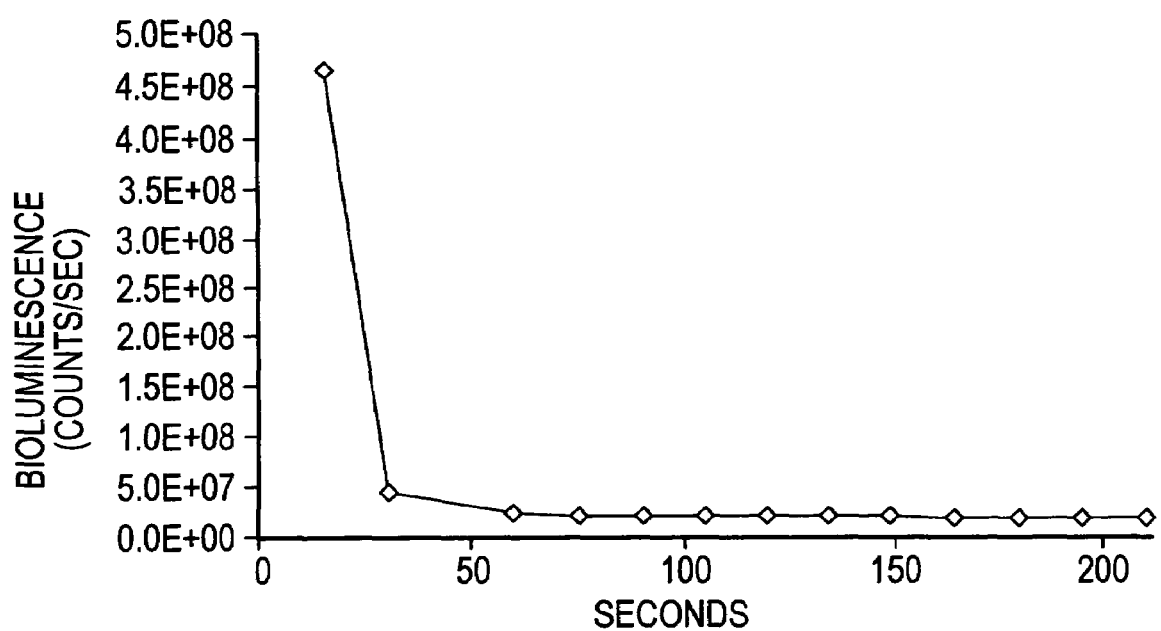
FIG. 47 shows bioluminescence as a function of time for a culture containing $4 \times 10^8$ CFU/mL. The results show a dramatic decrease in the bioluminescence with time, possibly due to oxygen limitation caused by the quiescent conditions of the vial.

Bioluminescence was determined for cultures containing different concentrations of *P. fluorescens* 5RL cells growing in LB supplemented with 10 ppm of the inducer molecule salicylate and 14.7 mg/L tetracycline (FIG. 46). Bioluminescence was determined using the integrated circuit microluminometer and a light-tight enclosure mounted above the chip. Linear regression analysis showed that the data fit a linear model indicating that bioluminescence per cell remains constant for cell concentration ranging from $4 \times 10^5$ to $2 \times 10^8$ CFU/mL and for detector responses ranging from 0.05 to 20 pA (FIG. 46). Using a linear model, the limit of detection for this experimental geometry was estimated to be $4 \times 10^5$ cells per mL. At cell concentrations greater than $4 \times 10^8$ CFU/mL, the bioluminescence decreased, possibly due to oxygen limitation caused by the quiescent conditions of the vial (FIG. 47).

Figure 48:
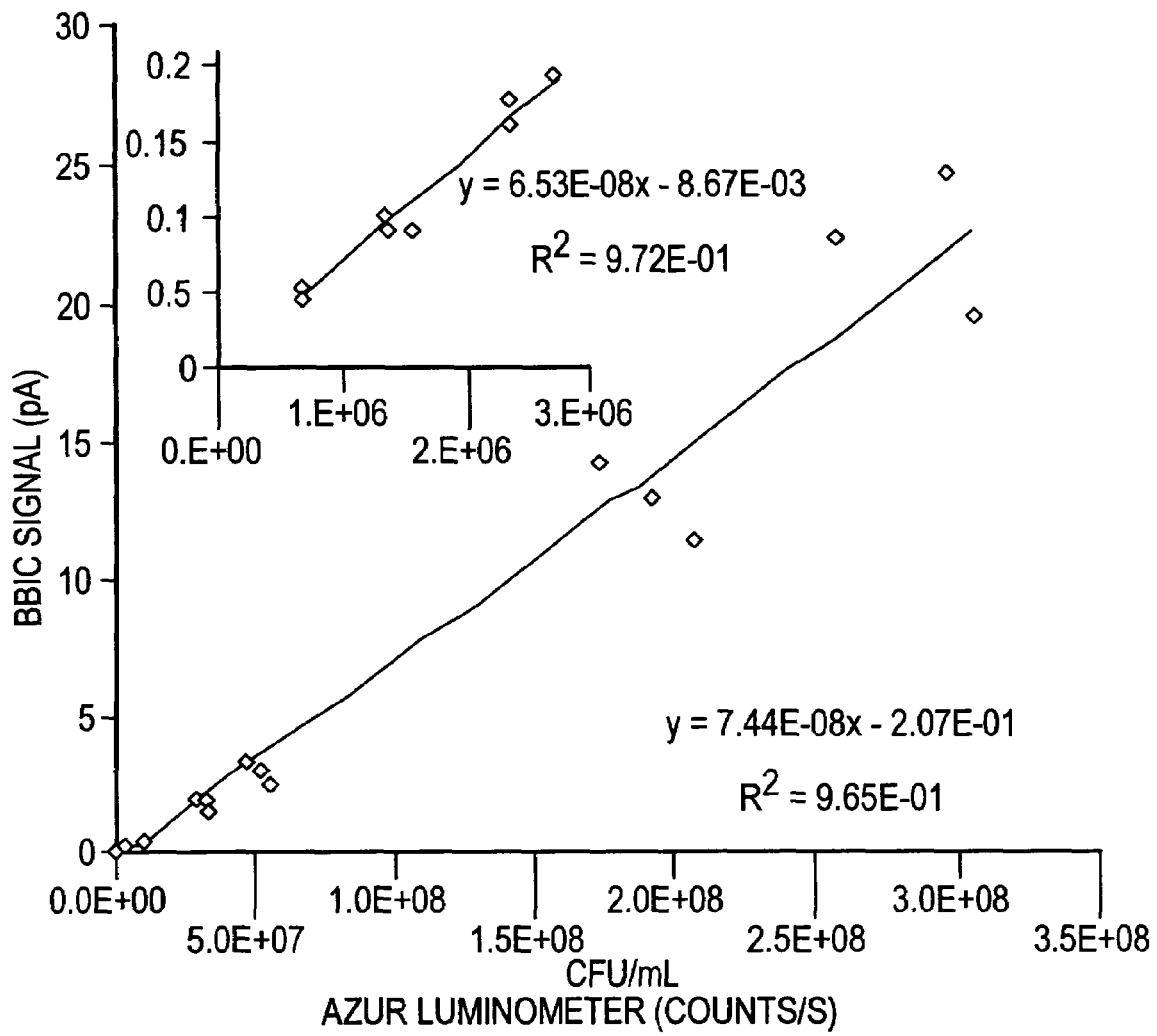
FIG. 48 is a comparison of bioluminescence signal as detected by the integrated circuit and a PMT-based luminometer.

The results obtained with the BBIC microluminometer were compared with results collected with the Azur PMT-based luminometer at each cell concentration (FIG. 48). The data showed that the measured bioluminescence responses were proportional for cell concentrations ranging $4 \times 10^5$ to $2 \times 10^8$ CFU/mL, indicating that the BBIC microluminometer gave consistent results to standard PMT-based detection systems.

Biosensors

A "biosensor" generally refers to a small, portable, analytical device based on the combination of recognition biomolecules with an appropriate transducer, and which detects chemical or biological materials selectively and with high sensitivity. A treatise on this subject is given by Paddle (1996), from which the following is excerpted:

They may be used to detect toxic substances from a variety of sources such as air, water or soil samples or may be used to monitor enclosed environments. They also may be formulated as catheters for monitoring drug and metabolite levels in vivo, or as probes for the analysis of toxic substances, drugs or metabolites in samples of say, blood and urine. Some biosensors with these potentials are currently either commercially available or undergoing commercial development (Alvarez-Icaza and Bilitewski, 1993).

A great number of review articles (e.g., Grate et al., 1993) and several books (e.g., Hall, 1991) have been written describing both the theoretical and practical aspects of individual biosensor technologies and their development.

Biosensors

In biosensors, different biological elements may be combined with various kinds of transducers provided that the reaction of the biological element with the substrate can be monitored. Table 1 lists the transducer types available and biological elements that have been combined with them to form a biosensor (Griffiths and Hall, 1993).

Biological Component of Biosensors

The biological components of biosensors are not only responsible for the selective recognition of the analyte, but also the generation of the physiochemical signal monitored on the transducer and, ultimately, the sensitivity of the final device. They can be divided into two distinct categories: catalytic and non-catalytic. The catalytic group includes enzymes, microorganisms and tissues. Devices incorporating these elements are appropriate for monitoring metabolites in the millimolar to micromolar range and can be used for continuous monitoring. The non-catalytic or affinity class biological component comprises antibodies (or antigens), lectins, receptors and nucleic acids which are more applicable to 'single use' disposable devices for measuring hormones, steroids, drugs, microbial toxins, cancer markers and viruses at concentrations in the micromolar to picomolar range. More recently, a hybrid configuration of biosensor has been introduced which combines the attributes of both the high affinity ('irreversible') binding of an antibody or DNA/RNA probe with the amplification characteristics of an enzyme. These systems are capable of monitoring analytes in the picomolar to femtomolar ($10^{-12}$-$10^{-15}$ M) concentration range and lower.

TABLE 1

BIOSENSOR COMBINATIONS

| | Transducer | |
|---|---|---|
| Biological Element | Type | Examples |
| Electrochemical | | |
| Enzymes<br>Receptors<br>Micro-organisms<br>Plant and animal tissues<br>Enzyme-labeled antibodies | Potentiometric | Redox and ion-selective electrodes (e.g., the pH electrode as well as $CO_2$, $NH_3$, and sulfide electrodes based on this), FETS and LAPS |
| Enzymes<br>Micro-organisms<br>Plant and animal tissues<br>Enzyme-labeled antibodies | Amperometric | Clark oxygen electrode, mediated enzyme electrodes |
| Enzymes<br>Bilayer lipid membranes* | Conductimetric | Pt or Au electrodes for determining the change in conduction of the solution due to the generation of ions |

TABLE 1-continued

BIOSENSOR COMBINATIONS

| Biological Element | Transducer | |
|---|---|---|
| | Type | Examples |
| *Optical* | | |
| Receptors<br>Antibodies | Fluorescence | Optrode, photodiodes, fiber-optic, bulk phase detection |
| Enzymes | Luminescence | Optrode, photodiodes, fiber-optic, bulk phase detection |
| Receptors<br>Antibodies | Evanescent wave | Coated fiber-optic, fluorescence detection |
| Antibodies<br>Antigens<br>Enzymes<br>Nucleic acids | Surface plasmon resonance | BIAcore (coated gold or silver layer on glass support), small haptens must be measured indirectly by displacement assay |
| Antibodies<br>Antigens<br>Enzymes<br>Nucleic acids | Acoustic | Piezoelectric devices |
| Enzymes<br>Micro-organisms<br>Cells | Calorimetric | Thermistor or thermopile |

*Man made.

Enzymes

From an analytical point of view, the most important classes of enzymes are the oxidoreductases, which catalyse the oxidation of compounds using oxygen or NAD, and the hydrolases, which catalyse the hydrolysis of compounds. Most successful biosensors exploit enzymes as the biological recognition/response system because of the range of transducible components such as protons, ions, heat, light, electrons and mass that can be exchanged as part of their catalytic mechanism. This catalytic activity is controlled by pH, ionic strength, temperature and the presence of co-factors. Enzyme stability is usually the deciding factor in determining the lifetimes of enzyme based biosensors (typically between 1 day and 1 or 2 months.

Organelles (e.g., mitochondria, chloroplasts) whole cells (e.g., bacteria) or tissue sections from animal or plant sources have been used as biocatalytic packages in biosensors for a large range of metabolites of clinical interest. Together with the numerous enzymes present are all the other necessary components needed to convert substrates into products in an environment which has been optimized by evolution. The major drawback of the use of such systems is their multi-enzyme behavior, which results in decreased substrate specificity. However, sometimes such behavior can work to advantage because by merely changing the external experimental conditions different substrates can be measured with the same biocatalytic material. The appropriate use of enzyme inhibitors, activators and stabilizing agents also can be used to enhance the selectivity and lifetimes of tissue based biosensors.

Receptors

Naturally occurring receptors are non-catalytic proteins that span cell membranes, extending into both the extracellular and intracellular spaces. They are involved in the chemical senses, such as olfaction and taste, as well as in metabolic and neural biochemical pathways. Within the organism they act as links in cell-cell communication by reversibly binding specific neurotransmitters and hormones liberated from other cells for the purpose of conveying messages through the target cell's membrane to initiate or diminish its cellular activity. They are also the binding sites for many drugs and toxins. Two methods have been defined by which binding of a transmitter molecule to the extracellular side of the receptor leads to modification of intracellular processes.

Attempts at using neuroreceptors as the recognition element in biosensors have largely been restricted to the nicotinic acetylcholine receptor (n-AChR) which can be isolated from the electric organ of the electric eel or ray in relatively large quantities. The unavailability of other receptors for biosensor use is no doubt a reflection of the fact that they are normally only present in small amounts in tissues and are unstable once removed from their natural lipid membrane environment. However, the products of receptor DNA expression in foreign cell lines may produce proteins useful for biosensor applications, yet not fully identical to the native starting material. The n-AChR and associated ion channel complex binds several naturally occurring toxins.

Antigens and Antibodies

An antigen is any molecular species that can be recognized by an animal organism as being foreign to itself and which therefore triggers the defensive mechanism known as the immune response. This recognition has a lower molecular weight cut-off of ~10,000 Da. In natural circumstances such antigens are typically proteins or lipopolysaccharides at the surfaces of viruses, bacteria and microfungi, or at the surfaces of cells and in solution in blood or tissues of other species or even of different individuals of the same species. Foreign DNA or RNA is also antigenic as is material of plant origin.

An antibody (Ab) is a molecule produced by animals in response to the antigen and which binds to the latter specifically. Antibodies to smaller molecular weight environmental contaminants such as pesticides, herbicides, microbial toxins and industrial chemicals can be made after first covalently attaching the latter to a carrier protein such as bovine serum albumin (BSA) or keyhole limpet haemocyanin (KLH). The small molecular component of the resultant conjugate, which has been modified for antigenic recognition, is known as a hapten. A host of other biotoxins of microbial, plant and animal origin are either antigenic or can be rendered antigenic by the formation of hapten-protein conjugates.

In mammals, two distinct types of molecule are involved in the recognition of antigens. These are the proteins called immunoglobulins which are present in the serum and tissue fluids, and the antigen receptors on the surface of specialized blood cells-the T-lymphocytes. It is the immunoglobulins, or antibodies, whose selective and tight binding characteristics for antigens are made use of in immunological methods of analysis. In most higher animals the immunoglobulins, or antibodies, fall into five distinct classes, namely IgG, IgA, IgM, IgD and IgE. These differ from each other in size, charge, amino acid composition and carbohydrate content. They all appear to be glycoproteins but the carbohydrate content ranges from 2-3% for IgG to 12-14% for the others. The basic structure of all immunoglobulin molecules is a Y-shaped unit consisting of two identical light polypeptide chains and two identical heavy polypeptide chains linked together by disulfide bonds. The amino terminal ends of the 'arms' of the Y are characterized by sequence variability and are the antigen binding sites. IgG is the exclusive anti-toxin class of antibody. IgM is a pentamer of five Y-shaped units whose role appears to be to complex infectious organisms.

The binding of antigen to antibody at transducer surfaces can be measured directly and indirectly. Binding can be detected by conjugating the antigen or antibody to a fluorescent label.

Another possibility is to use DNA binding proteins such as RNA polymerases, promoters, repressors and restriction enzymes, which exhibit the ability to bind to a specific DNA sequence in a double-stranded form to develop a biosensor. Since the preparation of the DNA in single-stranded form and its subsequent hybridization would not be required, the method would involve a shorter sample preparation time.

Viruses, Bacteria and Fungi

Viruses are small cellular parasites that cannot reproduce by themselves. They attach to cells via specific receptors and this partly determines which cell types become infected. The particular cells that are infected are ultimately destroyed because of the complex biochemical disturbances accompanying the intracellular replication of the virus. Viruses contain either single-stranded or double-stranded RNA or DNA, which is generally surrounded by an outer shell of one or more virus-specific proteins or glycoproteins. In some viruses there is a further external envelope that consists mainly of lipids but also contains some virus-specific proteins. It is the surface coat proteins, which are the viral antigens that trigger the immune response and antibody production. Viruses (and bacteria) have a large number of antigenic determinants on their surfaces and therefore each organism can bind a number of antibody units. This results in a considerable increase in stability of virus-antibody complexes over hapten-antibody complexes (up to $10^3$-$10^4$-fold depending on the antibody).

TABLE 2

PATHOGENIC ORGANISMS

| Viruses | Bacteria | Fungi |
| --- | --- | --- |
| Variola virus | *Rickettsia prowazecki* | *Coccidioides immitis* |
| Chikungunya virus | *Rickettsia rickettsi* | *Histoplasma capsulatum* |
| Eastern encephalitis virus | *Rickettsia tsutsugamushi* | *Norcardia asteroides* |
| Venezuelan encephalitis virus | *Bacillus anthracis* | |
| Western encephalitis virus | *Francisella (Pasteurellas tularensis)* | |
| Dengue virus | *Pasteurella pestis* | |
| Yellow fever virus | *Brucella melitensis. B. suis* | |
| Japanese encephalitis virus | *Coxiella burnetti* | |
| Russian spring-summer encephalitis virus | *Salmonella typhi* | |
| Argentine haemorrhagic fever virus | *Salmonella paratyphi* | |
| Lassa fever virus | *Vibrio comma* | |
| Lymphocyte choriomeningitis virus | *Corynebacterium diphtheria* | |
| Bolivian haemorrhagic fever virus | *Actinobacillus mallei* | |
| Crimean-Congo haemorrhagic fever virus | *Pseudomonas pseudomallei* | |
| Haantan (Korean haemorrhagic fever) virus | *Mycobacterium tuberculosis* | |
| Rift Valley fever virus | | |
| Marburg virus | | |
| Ebola virus | | |
| Hepatitis A virus | | |

Nucleic Acids

The specific sequence of bases along a strand of DNA and the unique complementary nature of the pairing between the base pairs (adenine and thymine or cytosine and guanine) of adjacent strands in the double helix is the basis of biodiversity. The ability of a single-stranded nucleic acid molecule to recognize and bind (hybridize) to its complementary partner in a sample has been used in genetic analyses and may also be used in a biosensor.

Sample preparation might include one or more of the following steps: (a) extraction of the DNA from the cells in a sample; (b) preparation of the DNA in single stranded form; and (c) increasing the total amount of DNA present by the use of the polymerase chain reaction (PCR™).

Certain pathogenic bacteria synthesize and secrete exotoxins as part of the mechanism underlying the specific symptoms of the diseases that they produce. Examples of these proteins that poison or kill susceptible mammalian cells are the *Shigella dysenteria* toxin. *Staph. aureus* enterotoxin, tetanus toxin and *botulinum* neurotoxin, as well as the toxins produced by *Bacillus anthracis* and *Corynebacterium diphtheriae*. Other pathogenic bacteria (the *Salmonella* and *Brucella* species in Table 2) liberate toxins when they are lysed. These toxins are components of the bacterial cell wall and are conjugates of protein, lipid and carbohydrate and have been called endotoxins. Both types of toxin are antigenic. The different types of bacteria have different cell wall structures. All types (Gram-positive (G+), gram-negative (G−) and mycobacteria) have an inner cell membrane and a peptidoglycan wall. Gram-negative bacteria also have an outer lipid bilayer in which lipopolysaccharide is sometimes found. The outer surface of the bacterium may also contain fimbriae or flagellae, or be covered by a protective capsule. Proteins and polysaccharides in these structures can act as targets for the antibody response.

Some fungi are pathogenic to man because they can invade the body tissues and proliferate there rather than because they liberate toxins. Three of these are listed in Table 2. Other fungi are dangerous to humans because of the toxins they produce and liberate into the environment. A particular example of the latter is the *fusarium* species, which produce tricothecene mycotoxins mentioned.

Fungi may be utilized as a bioreporter. The inventors contemplate the use of fungi (e.g., yeast) in methods of the present invention. For example, yeast strains may be constructed by methods similar to those disclosed herein for bacterial strains in which the yeast will emit a bioluminescent signal in response to an environmental signal or stress.

Biosensors Based on Antibodies

There is a wide range of toxins for which enzyme based and receptor based strategies are not available for the development of biosensors. However, assuming that one can obtain the appropriate antibodies, antibody based biosensors are possible for several of toxic chemicals and probably all toxins and pathogenic micro-organisms listed in Table 2.

One of the continuing challenges in the development of immunosensors is to be able to immobilize the antibodies at high density on the appropriate surface whilst still maintaining their functional configuration and preventing stearic hindrance of the binding sites. This has led to the use of self-assembling long chain alkyl membrane systems (SAMSs) on glass or silica and gold surfaces. The terminal functional groups on each chain are designed to react with specific groups on antibodies or antibody fractions to form a uniform geometrical array of antigen binding sites.

The stability of the immobilized antibodies is also a critical factor for future immunosensor research. A problem associated with this is that if on-site preparation of the system for the capture process is required, this may take several h and methods need to be developed to speed this up. A further requirement which is more important for immobilization on piezoelectric devices is the need to reduce non-specific protein binding to the sensor surface. Perhaps one approach to this problem would be to use a SAM formed from a mixture of two long chain alkane thiolates, one with a terminal functional group for reaction with, for example, Fab-SH groups and the other presenting a short oligomer of ethylene glycol to resist the non-specific adsorption of protein at the membrane surface (Mrksich & whitesides, 1995). This mixture would allow the possibility of controlling the spacing of the covalently bound antibody fraction and optimizing specific antigen binding.

Most immunological reactions are essentially irreversible because of their large association constants ($K_a$s of $10^5$-$10^9$ $M^{-1}$). The $K_a$S are composed of large forward [$k_1$] and small reverse [$k_{-1}$] rate constants ranging from $10^7$ to $10^9$ $M^{-1}$ $s^{-1}$ and $10^2$ to $10^{-4}$ $s^{-1}$, respectively. Developing antibodies with sufficiently fast antigen dissociation rates to allow reversible measurements in real time could lead to continuous or at least sequential measurements of the antigen without the need to replace the antibody or reverse the binding by the use of chaotropic solutions. Recombinant technology will eventually allow the production of antibodies with new binding properties.

An approach that may solve the problem of irreversibility is the development of catalytic antibodies. Haptens designed to mimic the stereoelectronic features of transition states can induce antibodies capable of catalysing a wide range of chemical transformations, ranging from simple hydrolyses of esters and amides to reactions that lack physiological counterparts or are normally disfavored. Thus, it is conceivable that if catalytic antibodies can be obtained for toxic chemicals and toxins, then biosensors for these substances, capable of continuous unattended running and not requiring fresh supplies of sensor material, could become a reality.

Alternatively, to utilize immunoreactions effectively in sensor design, the problem of irreversibility may be circumvented by creating a reservoir that passively releases immunoreagents to the sensing region of the particular device. Controlled release polymers have been used for this purpose.

Recently, Wallace and co-workers (see Sadik et al., 1994) have suggested that because the Ag-Ab interaction is a multi-step process (involving a variety of different molecular interactions according to the distance apart), it is possible that specificity is locked in at the early stages and irreversibility occurs at the later stages, accompanied by conformational changes. Wallace et al. have presented evidence of this specificity from pulsed amperometric measurements using a platinum electrode coated in a film of polypyrrole containing the antibody to thaumatin. During continuous pulsing of the applied potential in the presence of the antigen, rapid and reversible peaks of current were observed whose height was directly proportional to the antigen concentration. Injections of BSA and other proteins gave very much reduced responses but it is not clear how much of this was due to the difference in charge structure.

Nucleic Acid Based Biosensors

The time consuming preparative steps in gene probe assays make it difficult for them to be considered as the basis of biosensors for the on-site detection of pathogenic micro-organisms. The major time-consuming steps are the DNA isolation and amplification (PCR™) procedures and the hybridization detection step. Recently, it has been possible to grow ss-DNA on the surface of optical fibers and to detect the hybridization process with complementary ss-DNA in a sample by using the fluorescence of ethidium bromide trapped in the double-stranded regions of the bound DNA. Besides, the possibility of being very sensitive and selective, such a nucleic acid based sensor has some advantages over antibody based biosensors. First, it is more stable and can be stored for longer periods. Also, the probe can be repeatedly regenerated for further use by a short immersion in hot buffer. Future work will be directed towards developing appropriate DNA probes for pathogenic bacteria and fungi and improving the methods for immobilizing them on the sensor surface. Detection of hybridization may be further improved by covalently immobilizing the ds-DNA sensitive fluorescent dye directly onto the immobilized ss-DNA at the glass fiber surface.

Microbial Biosensors Using Multiplexed Bioluminescence

Whole cell biosensors are occasionally limited in terms of sensitivity and reliability by signal transduction mechanisms and by non-specific interferences. Wood and Gruber (1996) provide an overview of accurately transducing the genetic sensing mechanisms of microbes into readily measurable signals. Because living cells are a steady-stage ensemble of hundreds of interacting biochemical pathways, it is difficult to change one path without affecting, to some degree, several other paths. With many potential internal and external conditions being sensed simultaneously in a cell, a change in any one could affect the cellular physiology in unpredictable ways. In a microbial sensor, this may lead to unreliable and even uninterpretable responses to environmental conditions.

In order to make microbial sensors more reliable, it may be necessary to ascertain the effects of the non-specific stimuli and eliminate them from the sensor response. The cumulative effect of the non-specific stimuli may be determined through a second signal transducer (not coupled to the specific genetic sensing system) to yield an internal control signal. This control signal may serve as a dynamic baseline with which to compare the target signal. Since the signal from the target transducer indicates the effects of both the targeted and non-specific stimuli, by normalizing the target signal to the control signal, the effects of the target stimulus can be isolated.

This may be achieved by employing two genetic reporters which behave essentially identically within the complex chemical environment of living cells, but yield readily differentiated signals. In preferred embodiments, the two genetic reporters may include bioluminescence proteins with subtle modifications between each other, such modifications providing a distinguishable change in emission wavelength. Examples of such variants are commercially available for many bioluminescent reporters and are well known in the art (see e.g., Wood, 1990).

Multiple bioluminescent reporters may be constructed to be translated into a single polypeptide comprising two functional bioreporters. If the excitation spectrum of one or more of the reporters is within the range of emission of one or more of the other reporters in such a construct, the inventors contemplate that this "hybrid" construct would provide increased signal strength or sensitivity or both over those comprising only one reporter. Alternatively, as opposed to being translated into a single polypeptide, the multiple bioluminescent reporters may be translated into separate polypeptides that encode regions that allow the reporters to bind each other or be in close proximity to each other. "Close proximity" refers to an arrangement where the emission of one or more of the reporters is able to excite one or more of the other reporters.

Recombinant Vectors Expressing Bioluminescence Genes

One important embodiment of the invention is a recombinant vector which comprises one or more nucleic acid segments encoding one or more bioluminescence polypeptides. Such a vector may be transferred to and replicated in a prokaryotic or eukaryotic host, with bacterial cells being particularly preferred as prokaryotic hosts, and yeast cells being particularly preferred as eukaryotic hosts.

In other embodiments, it is contemplated that certain advantages will be gained by positioning the coding DNA segment under the control of a recombinant, or heterologous promoter. As used herein, a recombinant or heterologous promoter is intended to refer to a promoter that is not normally associated with a DNA segment encoding a crystal protein or peptide in its natural environment. Such promoters may include promoters normally associated with other genes or promoters isolated from any bacterial, viral, eukaryotic, or plant cell, or both. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology. The promoters employed may be constitutive, or inducible, and can be used under the appropriate conditions to direct high level expression of the introduced DNA segment.

In a first embodiment, the recombinant vector comprises a nucleic acid segment encoding one or more bioluminescence polypeptides. Highly preferred nucleic acid segments are the lux genes of *Vibrio fischerii*, luxCDABE. Other preferred nucleic acid segments may include, but are not limited to, those that encode firefly luciferase, the luciferase proteins of other beetles, Dinoflagellates (*Gonylaulax; Pyrocystis*), Annelids (*Dipocardia*), Molluscs (Lativa), Crustacea (*Vargula; Cypridina*), green fluorescent protein of *Aequorea victoria* or *Renilla reniformis*, or luciferases from other organisms capable of bioluminescence.

In a second embodiment of the present invention, the inventors contemplate a recombinant vector comprising a nucleic acid segment encoding one or more enzymes that are capable of producing a reaction that yields a luminescent product or a product that can be directly converted to a luminescent signal. For example, substrates of the commonly used $\square$-galactosidase and alkaline phosphatase enzymes are commercially available that are luminescent (chemiluminescence) when converted by the respective enzyme.

In a third embodiment of the present invention, the inventors contemplate a recombinant vector comprising a nucleic acid segment encoding one or more enzymes that are capable of producing a reaction that yields a chromogenic product or a product that can be directly converted to a chromogenic signal. For example, substrates of the commonly used $\square$-galactosidase and alkaline phosphatase enzymes are commercially available that are chromogenic when converted by the respective enzyme. Appropriate choices of excitation and emission wavelengths will permit detection and quantization of the chromogenic compound. Likewise, any chromogenic substrate for which a standard assay is available for spectrophotometric analysis should be readily adaptable for use in the present methods.

In a fourth embodiment of the present invention, the inventors contemplate a recombinant vector comprising a nucleic acid segment encoding one or more polypeptides that expressed on the surface of a cell, or secreted from a cell. In a preferred embodiment, the nucleic acid segment encodes one or more TnPhoA polypeptides. In another embodiment, the polypeptide is an antigen of an antibody that, directly or indirectly, is capable of producing a bioluminescent, chemiluminescent, or chromogenic product.

In each of the above embodiments, the recombinant vector may comprise the gene of interest operatively linked to a promoter that is responsive to an environmental factor. In a preferred embodiment the lax genes of *Vibrio fischerii*, luxCDABE are operatively linked to the tod operon within a mini-Tn5 transposon. However, the inventors contemplate that virtually any recombinant vector that allows the nucleic acid segment of interest to be operatively linked to a promoter that is responsive to an environmental factor may be used. Useful recombinant vectors may include, but are not limited to, the gene of interest operatively linked to a promoter that is responsive to an environmental factor by means of gene fusions, operon fusions, or protein fusions.

Another important embodiment of the invention is a transformed host cell which expresses one or more of these recombinant vectors. The host cell may be either prokaryotic or eukaryotic, and particularly preferred host cells are those which express the nucleic acid segment or segments comprising the recombinant vector which encode the lux genes of *Vibrio fischerii*, luxCDABE. Bacterial cells are particularly preferred as prokaryotic hosts, and yeast cells are particularly preferred as eukaryotic hosts A wide variety of ways are available for introducing a nucleic acid segment expressing a polypeptide able to provide bioluminescence or chemiluminescence into the microorganism host under conditions which allow for stable maintenance and expression of the gene. One can provide for DNA constructs which include the transcriptional and translational regulatory signals for expression of the nucleic acid segment, the nucleic acid segment under their regulatory control and a DNA sequence homologous with a sequence in the host organism, whereby integration will occur or a replication system which is functional in the host, whereby integration or stable maintenance will occur or both.

The transcriptional initiation signals will include a promoter and a transcriptional initiation start site. In preferred instances, it may be desirable to provide for regulative expression of the nucleic acid segment able to provide bioluminescence or chemiluminescence, where expression of the nucleic acid segment will only occur after release into the proper environment. This can be achieved with operators or a region binding to an activator or enhancers, which are capable of induction upon a change in the physical or chemical environment of the microorganisms. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon or codons, a terminator region, and optionally, a polyadenylation signal (when used in an Eukaryotic system).

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon or codons, the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

By "marker" the inventors refer to a structural gene which provides for selection of those hosts which have been modified or transformed. The marker will normally provide for selective advantage, for example, providing for biocide resistance (e.g., resistance to antibiotics or heavy metals); complementation, so as to provide prototrophy to an auxotrophic host and the like. One or more markers may be employed in the development of the constructs, as well as for modifying the host.

Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host. Desirably, the nucleic acid segment able to provide bioluminescence or chemiluminescence will be in close proximity to the gene providing for complementation as well as the gene providing for the competitive advantage. Therefore, in the event that the nucleic acid segment able to provide bioluminescence or chemiluminescence is lost, the resulting organism will be likely to also have lost the complementing gene, and the gene providing for the competitive advantage, or both.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the $\lambda_L$ and $\lambda_R$ promoters, the tac promoter. See for example, U.S. Pat. No. 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, U.S. Pat. No. 5,441,884, incorporated specifically herein by reference.

The desired gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for bioluminescence or chemiluminescence activity. If desired, unwanted or ancillary DNA sequences may be selectively removed from the recombinant bacterium by employing site-specific recombination systems, such as those described in U.S. Pat. No. 5,441,884, specifically incorporated herein by reference.

Methods for Preparing Antibodies

In another aspect, the present invention contemplates an antibody that is immunoreactive with a polypeptide. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. In a preferred embodiment, an antibody is a polyclonal antibody.

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for given polypeptides may be prepared using conventional immunization techniques, as will be generally known to those of skill in the art. A composition containing antigenic epitopes of particular polypeptides can be used to immunize one or more experimental animals, such as a rabbit or mouse, which will then proceed to produce specific antibodies against the polypeptide. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored or the animal can be used to generate mAbs (below), or both.

One of the important features provided by the present invention is a polyclonal sera that is relatively homogenous with respect to the specificity of the antibodies therein. Typically, polyclonal antisera is derived from a variety of different "clones," i.e. B-cells of different lineage. mAbs, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are therefore more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality up to 90% or 95% or greater is contemplated.

To obtain mAbs, one would also initially immunize an experimental animal, often preferably a mouse, with a polypeptide-containing composition. After a period of time sufficient to allow antibody generation, one would obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired polypeptide.

Following immunization, spleen cells are removed and fused, using a standard fusion protocol with plasmacytoma cells to produce hybridomas secreting mAbs against a polypeptide of interest. Hybridomas which produce mAbs to the selected antigens are identified using standard techniques, such as ELISA and Western blot methods. Hybridoma clones can then be cultured in liquid media and the culture supernatants purified to provide the polypeptide of interest-specific mAbs.

Of particular utility to the present invention are antibodies tagged with a fluorescent or enzymatic molecule. Methods of tagging antibodies are well known to those of skill in the art and a large number of such antibodies are available commercially. Fluorescent tags include, but are not limited to, fluorescein, phycoerythrin, and Texas red. Enzymatic tags, include, but are not limited to, alkaline phosphatase and horseradish peroxidase.

Nucleic-Acid Segments

The present invention also concerns nucleic acid segments that can be isolated from virtually any source, that are free from total genomic DNA and that encode bioluminescence peptides disclosed herein. Nucleic acid segments encoding these peptide species may prove to encode proteins, polypeptides, subunits, functional domains, and the like of lux-related or other non-related gene products. In addition these nucleic acid segments may be synthesized entirely in vitro using methods that are well-known to those of skill in the art.

As used herein, the term "nucleic acid segment" refers to a nucleic acid molecule that has been isolated free of total genomic nucleic acid of a particular species. Therefore, a nucleic acid segment encoding a bioluminescence peptide refers to a nucleic acid segment that contains a bioluminescence polypeptide coding sequences yet is isolated away from, or purified to be free from, total genomic nucleic acid of the species from which the nucleic acid segment is obtained. Included within the term "nucleic acid segment," are nucleic acid segments and smaller fragments of such segments, and also recombinant vectors, including, for example, plasmids, cosmids, phagemids, phage, viruses, and the like.

Similarly, a nucleic acid segment comprising an isolated or purified bioluminescence gene refers to a nucleic acid segment which may include, in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those skilled in the art, this functional term includes both genomic sequences, cDNA sequences and smaller engineered gene segments that express, or may be adapted to express proteins, polypeptides or peptides. In a preferred embodiment, the nucleic acid segment comprises an operon of lux genes.

"Isolated substantially away from other coding sequences" means that the gene, or operon, of interest, in this case, an operon encoding bioluminescence polypeptides, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The various probes and primers designed around the disclosed nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12, and so on. For a 15-mer, the probes correspond to bases 1 to 15, 2 to 16, 3 to 17, and so on. For a 20-mer, the probes correspond to bases 1 to 20, 2 to 21, 3 to 22, and so on.

It will also be understood that this invention is not limited to the particular nucleic acid sequences which encode peptides of the present invention. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by humans may be introduced through the application of site-directed mutagenesis techniques, e.g., to introduce improvements to the bioluminescence of the protein or to test mutants in order to examine activity at the molecular level.

If desired, one may also prepare fusion proteins and peptides, e.g., where the peptide-coding regions are aligned within the same expression unit with other proteins or peptides having desired functions, such as plastid targeting signals or "tags" for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning or PCR™ technology, or both in connection with the compositions disclosed herein.

In other embodiments, it is contemplated that certain advantages will be gained by positioning the coding nucleic acid segment under the control of a recombinant, or heterologous, promoter. As used herein, a recombinant or heterologous promoter is intended to refer to a promoter that is not normally associated with a nucleic segment encoding one or more bioluminescence polypeptides in its natural environment. Such promoters may include promoters normally associated with other genes, or promoters isolated from any bacterial, viral, eukaryotic, or plant cell, or both. Naturally, it will be important to employ a promoter that effectively directs the expression of the DNA segment in the cell type, organism, or even animal, chosen for expression.

The use of promoter and cell type combinations for protein expression is generally known to those of skill in the art of molecular biology, for example, see Sambrook et al., 1989. The promoters employed may be constitutive, or inducible, and can be used under the appropriate conditions to direct high-level expression of the introduced DNA segment, such as is advantageous in the large-scale production of recombinant proteins or peptides. Preferred promoters are those that are induced in the presence of environmental factors or stress.

The ability of such nucleic acid probes to specifically hybridize to bioluminescence polypeptide-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of such as 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, etc.; 60, 61, 62, 63, etc.; 70, 71, 72, 73, etc., 80, 81, 82, 83, etc., 90, 91, 92, 93, etc.; 100, 101, 102, 103, etc.; 150, 151, 152, 153, etc.; including all integers through the 200-500; 500-1,000; 1,000-2,000; 2,000-3,000; 3,000-5,000; 5,000-10,000 ranges, up to and including sequences of about 12,001, 12,002, 13,001, 13,002 and the like nucleotides or so, identical or complementary to nucleic acid sequences disclosed herein are particularly contemplated as hybridization probes for use in, e.g., Southern and Northern blotting. Smaller fragments will generally find use in hybridization embodiments, wherein the length of the contiguous complementary region may be varied, such as between about 10 to 14 and about 100 or 200 nucleotides, but larger contiguous complementary stretches may be used, according to the length complementary sequences one wishes to detect.

The use of a hybridization probe of about 14, 15, 16, 17, 18, or 19 nucleotides in length allows the formation of a duplex molecule that is both stable and selective. In order to increase stability and selectivity of the hybrid molecules having contiguous complementary sequences over stretches greater than 14, 15, 16, 17, 18, or 19 bases in length are generally preferred and thereby improve the quality and degree of specific hybrid molecules obtained; however, one will generally prefer to design nucleic acid molecules having gene-complementary stretches of 15 to 20 contiguous nucleotides, or even longer, where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202, incorporated herein by reference, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt, or high temperature conditions, such as provided by about 0.02 M to about 0.15 M NaCl at temperatures of about 50° C. to about 70° C., or both. Such selective conditions tolerate little, if any, mismatch between the probe and the template or target strand, and would be particularly suitable for isolating bioluminescence polypeptide-encoding DNA segments. Detection of DNA segments via hybridization is well known to those of skill in the art.

Of course, for some applications, for example, where one desires to prepare mutants employing a mutant primer strand hybridized to an underlying template or where one seeks to isolate bioluminescence polypeptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature does. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent and enzymatic, which are capable of giving a detectable signal. In preferred embodiments, one will likely desire to employ a fluorescent label or an enzyme tag, such as urease, alkaline phosphatase or peroxidase. In the case of enzyme tags, colorimetric indicator substrates are known that can be employed to provide a means visible to the human eye or spectrophotometrically to identify specific hybridization with complementary nucleic acid-containing samples. Similarly, in the case of fluorescent tags, fluorescent indicators are known that can be employed to provide a means visible to the apparatus of the present invention.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). After washing of the hybridized surface so as to remove nonspecifically bound probe molecules, specific hybridization is detected, or even quantitated, by means of the label. Means for probe labeling and hybrid detection are well known to those of skill in the art.

Methods for Preparing Mutagenized DNA Segments

In certain circumstances, it may be desirable to modify or alter one or more nucleotides in one or more of the promoter sequences disclosed herein for the purpose of altering or changing the transcriptional activity or other property of the promoter region. In general, the means and methods for mutagenizing a DNA segment are well known to those of skill in the art. Modifications to such segments may be made by random or site-specific mutagenesis procedures. The promoter region may be modified by altering its structure through the addition or deletion of one or more nucleotides from the sequence which encodes the corresponding unmodified promoter region.

Mutagenesis may be performed in accordance with any of the techniques known in the art such as and not limited to synthesizing an oligonucleotide having one or more mutations within the sequence of a particular promoter region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired promoter region or peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector.

The preparation of sequence variants of the selected promoter-encoding DNA segments using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment.

A number of template dependent processes are available to amplify the target sequences of interest present in a sample. One of the best-known amplification methods is the polymerase chain reaction (PCR™). Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products and excess primers will bind to the target and to the reaction products. The process is then repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs.

Q-beta Replicase may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR), is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Still other amplification methods may be used in accordance with the present invention. In one application, "modified" primers are used in a PCR™ like, template and enzyme dependent synthesis. The primers may be modified by labeling with a capture moiety (e.g., biotin) and/or a detector moiety (e.g., enzyme). In another application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) include nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

A nucleic acid amplification process involving cyclically synthesizing single-stranded RNA ("ssRNA"), single-stranded DNA (ssDNA), and double-stranded DNA (dsDNA), may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H(RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target ssDNA followed by transcription of many RNA copies of the sequence. This scheme is not cyclic, i.e. new templates are not produced from the resultant RNA transcripts. Other amplification methods include "RACE", and "one-sided PCR™" which are well known to those of skill in the art.

Methods based on ligation of two (or more) oligonucleotides in the presence of nucleic acid having the sequence of the resulting "di-oligonucleotide", thereby amplifying the di-oligonucleotide, may also be used in the amplification of DNA sequences of the present invention.

Biological Functional Equivalents

Modification and changes may be made in the structure of the peptides of the present invention and DNA segments, which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons listed in Table 3.

TABLE 3

TABLE OF CODONS

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as antigen-binding regions of antibodies or binding sites on substrate molecules. Since it is the interactive capacity and nature of a protein that defines that protein's biological functional activity, certain amino acid sequence substitutions can be made in a protein sequence; and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Bioluminescent Bioreporters

In prokaryotes, a bioluminescent bioreporter, designated lux, consists of a luciferase composed of two different subunits coded by the genes luxA and luxB that oxidize a long chain fatty aldehyde to the corresponding fatty acid resulting in a blue-green light emission near 490 nm (Tu and Mager, 1995). The system also contains a multienzyme fatty acid reductase consisting of three proteins (a reductase encoded by luxC, a transferase encoded by luxD, and a synthetase encoded by luxE) which initially converts and recycles the fatty acid to the aldehyde substrate. Thus, no exogenous addition of substrate is required to induce luminescence. The genes are contained on a single continuous operon. This genetic configuration allows the cloning of the complete lux gene cassette (reporter genes) downstream from different promoters for the utilization of bioluminescence to monitor gene expression.

Implicit in the use of a bioreporter strain for a BBIC is that the bioluminescent signal generated is directly related to the concentration of the target substance, most desirably in a selective and quantitative manner. In general, lux reporter genes are placed under the regulatory control of inducible operons maintained in native plasmids, broad host range plasmids, or chromosomally integrated into the host strain. In these genetic systems, the target analyte or its degradation products act as the inducer of the bioluminescence genes, and are responsible for selectivity and the resultant response. For example, *P. fluorescens* HK44 is a bioreporter that produces light in the presence of naphthalene. This strain has two genetic operons positively regulated by a LysR protein. One of the operons contains the lux bioluminescence genes and the other the genes responsible for the degradation of naphthalene to salicylate, the metabolic intermediate of naphthalene degradation. Both operons are induced when salicylate interacts with the regulatory protein NahR. Exposure of HK44 to either naphthalene or salicylate results in increased naphthalene gene expression and increased bioluminescence.

Studies in continuous cultures of *P. fluorescens* HK44 have demonstrated that the magnitude of the bioluminescence response correlated with the aqueous phase concentration of naphthalene under dynamic pulsed perturbation conditions (King, 1990). Reproducible bioluminescence was observed not only in aqueous naphthalene samples but also in soil slurry samples which were spiked with naphthalene, complex soil leachates, and the water soluble components of jet fuel (Heitzer, et al., 1992). *P. fluorescens* HK44 can be applied in environmental use for either quantitative analysis of contaminant presence or bioavailability. However, for such applications both the chemical complexity of the environment and the physiological conditions of the organisms must be considered in interpreting the bioluminescence response.

Many types of bioluminescent (lux) transcriptional gene fusions have been used to develop light emitting bioreporter bacterial strains to sense the presence, bioavailability, and biodegradation of other pollutants including toluene (Applegate, et al., 1997), and isopropylbenzene (Selifonova, et al., 1993) Analogous genetic approaches have also been reported for inducible heavy metal detoxification and resistance systems including mercury as well as the heat shock response and response to oxidative stress. In addition, genetically engineered Gram positive bioreporters have been used to examine the efficacy of antimicrobial agents where decreased light was equated to greater efficacy (Andrew and Roberts (1993). Eukaryotic bioreporters have also been generated to detect toxic compounds (Andrew and Roberts, 1993), oxygen, ultraviolet light, and estrogenic and antiestrogenic compounds (Anderson, et al., 1995). Environmental applications involving bioluminescence measurements have been reviewed (Steinberg and Poziomek, 1995).

Cell Entrapment

Various methods exist for the entrapment of microbial cells at or near the light-sensing portion of the IC. For instance, cells can be simply entrapped behind a porous membrane or encapsulated in natural or synthetic polymers.

Polymeric matrices can provide a hydrated environment containing nutrients and co-factors needed for cellular activity and growth. In addition, encapsulated cells are protected from toxic substances in their environment and maintain increased plasmid stability. Cells can be encapsulated in thin films or small diameter beads in order to be adaptable to the small surface area available on the IC. Thin films can be formed by mixing cells in a liquid polymer that is then micropipetted on the IC in a thin layer and allowed to polymerize. Larger blocks of cells can also be made from which films of virtually any desired thickness can be sliced and attached to the IC. Microbeads are produced by spraying the liquid polymer/cell mixture through a nebulizer into a polymerizing agent.

Sol-gels have been used to exemplify a suitable encapsulation medium. Sol-gel is a silica-based glass that polymerizes under room temperature conditions. Although sol-gel has been used to encapsulate yeast cells, the reaction conditions necessary for polymerization (primarily low pH) are generally too harsh for bacterial cell immobilizations. Utilizing sonication methods, polymerization under pH conditions conducive to cell survival has been achieved. Toluene bioreporter (*Pseudomonas putida* TVA8) and a naphthalene bioreporter (*Pseudomonas fluorescens* HK44) have successfully been encapsulated in sol-gel and shown to produce bioluminescence when exposed to their specific inducers. However, cracking and drying within the thin sol gel matrices after polymerization may occur.

Alternatively, an alginate polymerization matrix may be utilized for on-chip applications. Alginate lacks the structural integrity of encapsulation agents such as sol gels, but has a significant advantage because of its straightforward adaptability to microbial encapsulation and its subsequent widespread use in cellular immobilization procedures. To increase mechanical stability, alginate encapsulated cells have been entrapped in 0.1 μm low adsorption/absorption filter membranes and hollow fiber membranes which allow for influx of chemical analytes while inhibiting alginate degradation and cellular release into the surrounding medium. Lyophilization is expected to increase long term storage of the encapsulated cells.

Additional Aspects of the Present Invention

In addition to the embodiments described in detail herein, the inventors further contemplate that the BBIC of the present invention may be used to detect pollutants, explosives, heavy-metals, or other chemical or biological agents residing in areas like groundwater, streams, rivers, oceans, or other environments. Furthermore, the BBIC of the present invention may be used in combinatorial chemistry in bio-medical-drug and anti-cancer screening, sensors for oil exploration, industrial process control, and biomedical instrumentation. The BBIC of the present invention may be used to respond to the absence or low abundance of test chemicals, e.g., $Fe^{+2}$ or $PO_4^{-3}$. In addition to compounds, the BBIC of the present invention may be used to detect environmental conditions, such as temperature, radiation, and pressure. The inventors contemplate that essentially any signal transduction pathway may be utilized provided the organism of the BBIC is capable of detecting the presence or absence of a substance or condition and alter the expression of a promoter operatively linked to a reporter gene.

Besides those described in detail herein, the inventors contemplate additional methods of powering the bioluminescent bioreporter integrated circuits (BBICs) of the present invention. They may be powered remotely by induction of RF, optical energy (including solar), mechanical energy (vibration, water flow, air flow, etc.), chemical energy, or thermal energy. In some embodiments of the present invention, the light generated by the sensing organism or compound may be used to power the BBIC.

The inventors contemplate that the BBICs of the present invention may be readout by wireless means (e.g., RF or on-chip light-emitting device) or alternatively, wired means (e.g., direct analog, digital, or passive means including resistance, capacitance, and inductance, etc.). The BBICs of the present invention may also be realized in bipolar silicon, silicon-germanium, GaAs, InP or other semiconductor IC processes.

The light-emitting agent of the present invention may be biological or chemical, wherein the light producing mechanism may be luminescence, fluorescence, or phosphorescence. The inventors further contemplate that the light emitting agent may be placed on the IC at the time of manufacture or selected and placed on the IC at the time of use. In other embodiments of the present invention, the inventors contemplate BBICs comprising arrays of light-emitting agents further comprising a matching array of light-detection devices. With the addition of signal processing (analog, digital, neural network, etc.), this array device may be used to detect a family of chemicals instead of an individual chemical. Additionally, the BBICs comprising arrays of light-emitting elements with different emission wavelengths further comprise an integrated photo-spectrometer. For example, by measuring the spectra of the emitted light, this embodiment may be used to detect a number of chemicals simultaneously or sequentially, instead of detecting a single chemical.

A number of methods of packaging the BBICs of the present invention may be envisioned. Generally, the type of packaging chosen may reflect the predicted environment to which the BBIC would be subjected. Such environments may include, but are not limited to, aqueous, gaseous, or solid environments. For example, the inventors contemplate a BBIC encased in concrete near a rebar to detect corrosion. In another embodiment, the inventors contemplate packaging the BBIC in a manner that may allow in vivo measurements for biomedical application (e.g., detecting disease, sensing a patient's condition, etc). Generally, the BBIC would be packaged in a semi-permeable membrane that would permit the particular fluid being examined (e.g., blood) to pass, while substances which would harm or interfere with the BBIC (e.g., a animal host defense mechanism) would be blocked.

Figure 33:
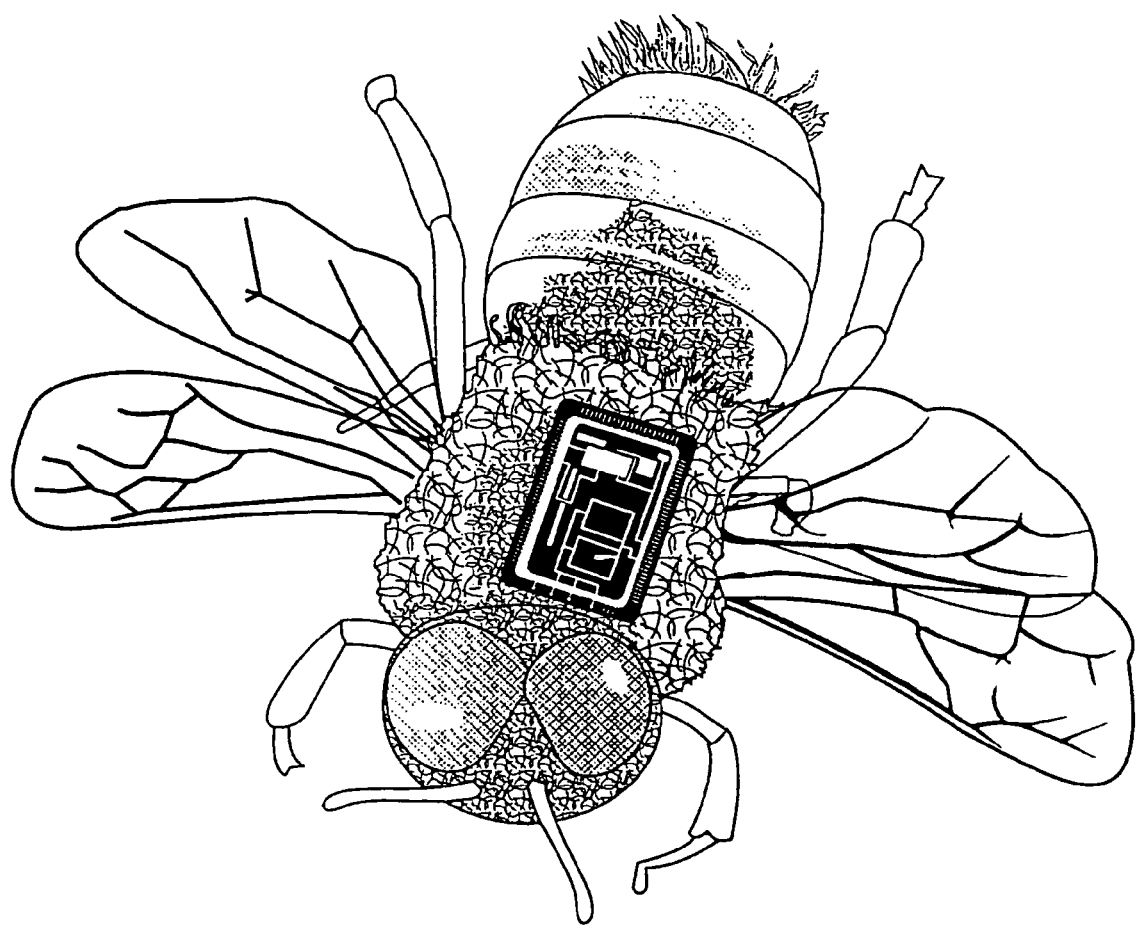
FIG. 33 shows IC mounted on a common honeybee as part of Oak Ridge National Laboratory research on microtransmitters.

In certain embodiments, the light-emitting agent of the present invention may comprise a multicellular organism (e.g., an insect). It is well known that larger organisms such as insects can be genetically engineered to bioluminesce in the presence of targeted substances. In such cases, the IC portion of the BBIC may be attached to an insect in such a way that the chip would detect the resulting bioluminesce. Such a system would be mobile, since the insect itself is mobile and unaffected by the presence of the attached BBIC. One such example of this application of the apparatus disclosed herein is illustrated in FIG. 33. The inventors further contemplate that when the light-emitting agent is a multicellular organism, the BBIC may be self-propelling and/or self-powering.

The inventors contemplate a BBIC comprising global position sensing that may allow the BBIC to sense location as well as the presence or absence of a certain compound or biological agent.

The inventors contemplate an array of BBICs connected in a wired or wireless distributed network to form an artificially intelligent sensing network. This array of BBICs may comprise on-chip processing capability on each BBIC.

Figure 34:
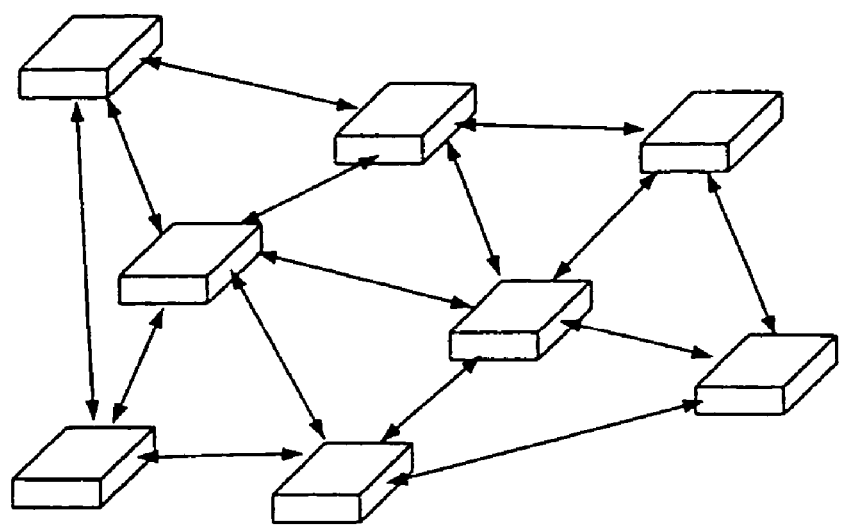
FIG. 34 shows BBICs connected together in a distributed neural network
Figure 35:
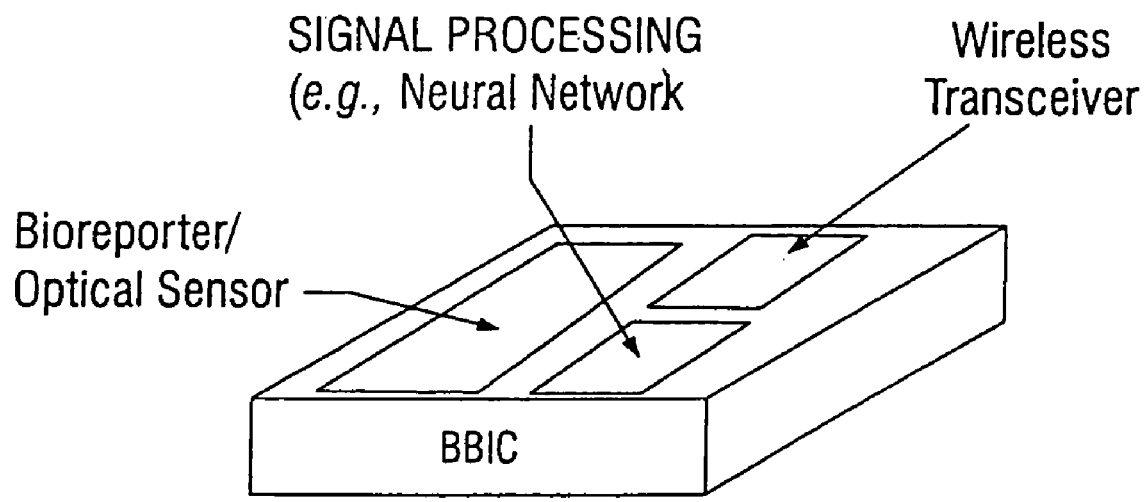
FIG. 35 shows a single BBIC from the distributed neural network.

BBICs could be distributed over a wide area, yet wirelessly connected together as shown in FIG. 34. If each BBIC had on-chip signal processing capabilities (e.g., neural network processing), this distributed network would form an artificially intelligent sensor system. For example, consider a large network of BBICs deployed over a large area where a toxic gas leak has occurred. As the gas cloud enters the area of the BBIC network useful information such as gas composition, speed, and direction of the cloud could be determined by the sensor network. If other information such as wind conditions, terrain topology, temperature, etc., were available to the network, the network could make predictions of risks to human populations.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Modified Mini-Tn5 System for Chromosomally-Introduced Lux Reporters

This example describes a cloning plasmid which allows inserts to be directionally cloned into a mini-Tn5 transposon vector. Such vectors are useful for preparing the bioreporter constructs useful in the methods of the present invention. As an exemplary embodiment, a tod-lux fusion was constructed and introduced into *Pseudomonas putida* F1 to examine the induction of the tod operon when exposed to BTEX compounds and aqueous solutions of JP-4 jet fuel constituents. Since this system contains the complete lux cassette (luxCDABE), bacterial bioluminescence can be measured in whole cells without the need to add an aldehyde substrate. The resultant strain was also evaluated for its stability and fitness compared to the wild type strain F1.

Materials and Methods
  Organisms and Culture Conditions
  Strains used in these studies are shown in Table 4. All cultures were grown at 28° C. except for *E. coli* strains, which were grown at 37° C.
  DNA Isolation and Manipulation
  Large scale plasmid DNA isolation was accomplished using a modified alkaline lysis protocol (Promega, 1992). Chromosomal DNA was prepared using the protocol outlined by Ausubel et al. (1989). All DNA preparations were further purified by CsCl EtBr ultracentrifugation (Sambrook et al., 1989). DNA modifications and restriction endonuclease digestions were performed.
  Cloning and Transposon Construction
  The transposon mini-Tn5KmNX was constructed using site-directed mutagenesis and the polymerase chain reaction. Two 58 base oligonucleotides, 5' and 3' with respect to the kanamycin resistance gene ($Km^R$) in PCRII™ (Invitrogen, San Diego, Calif.) were synthesized using a Beckman Oligo 1000 DNA synthesizer (Palo Alto, Calif.) following the manufacturer's protocol. Base substitutions were made to generate both I and O insertion sequences as well as unique NotI and XbaI sites inside the transposon for cloning. An EcoRI site and a NheI site were added to the end of each oligonucleotide, respectively, to allow cloning of mini-Tn5KmNX into the delivery vector pUT (Herrero et al., 1990). The sequence and base changes can be seen in FIG. 10. The primers were used to amplify the kanamycin resistance gene from pCRII™ using Touchdown PCR™ (Don et al., 1991) using the manufacturer's protocol with the following thermocycler conditions: 94° C. initial denaturation, 5 min; 5 cycles at 94° C. for 1 min, 72° C. annealing for 1 min, 72° C. extension for 2 min; the annealing temperature was lowered 5° C. every 5 cycles until 42° C. at which 8 cycles were run, followed by a final extension of 15 min at 72° C. The 1.3 kb product was cloned into pCRII™ using a TA cloning kit (Invitrogen, San Diego, Calif.) according to the manufacturer's protocol. The resultant plasmid pUTK210 containing the mini-Tn5KmNX was sequenced to verify the incorporation of both the I and O insertion sequences. After confirmation, pUTK210 was cleaved with NheI and EcoRI and gel-purified using agarose gel electrophoresis. The purified mini-Tn5 KmNX fragment was cloned into the XbaI-EcoRI site of the mini-Tn5 delivery vector, pUT and electroporated into *E. coli* S 17-1 (λpir). Electroporants with the proper inserts were selected on LB plates with 50 µg/ml kanamycin. DNA minipreps were obtained and inserts were verified by cleavage with restriction endonucleases.

The cloning vector, pLJS was constructed from pBluescript II (KS) (Stratagene, LaJolla Calif.) by cleaving with BssH II and religating to remove the multicloning site (MCS). Ligated DNA was transformed into DH5α and spread on LB plates supplemented with ampicillin (50 µg/ml) and X-gal (40 µg/ml). Transformants without the MCS were white since they were incapable of α-complementation. The resultant plasmid was named pBSMCS(−). Two oligonucleotides (a 47-mer and a 44-mer) with base substitutions were synthesized as previously described to regenerate the multicloning site and add the following restriction sites, XbaI, NheI, SpeI, and AvrII. The sequences and orientation of the added sites can be seen in FIG. 10. The new multicloning site was amplified from pBluescript II (KS) using the manufacturer's protocol with the following thermocycler conditions: 94° C. initial denaturation 5 min; 38 cycles of denaturation at 94° C. for 30 sec, annealing at 42° C. for 1 min, extension at 72° C. for 30 s; and, final extension at 72° C. for 15 min. The amplified fragment was cleaved with BssHII, ligated into pBSMCS(−) and transformed into DH5α™. Transformants were screened on LB agar with ampicillin (50 µg/l) and X-gal (40 µg/ml). Blue colonies were selected since they indicated restored α-complementation. The construct was sequenced to confirm the base substitutions and integrity of the MCS. pLJST2 was generated by directionally-cloning the 0.77 kb HindIII-HincII fragment containing the 5S ribosomal rrnB $T_1T_2$ transcription terminator from pKK223-3 (Pharmacia, Piscataway, N.J.) into pLJS cleaved with HindIII and SmaI. The NotI-AvrII terminator fragment from pLJST2 was subsequently cloned into the NotI-XbaI site of mini-Tn5KmNX. This allowed for the subsequent destruction of the XbaI site by heterologous ligation and the regeneration of the NotI and XbaI unique sites in mini-Tn5KmNX downstream of the terminator (pUTK211). Mini-Tn5 Kmtod-lux (pUTK214) was generated by directionally cloning the 10.2 kb NotI-XbaI tod-lux fragment from pUC 18 Not tod-lux (Table 4) into the NotI-XbaI site of pUTK211. Both insert and vector DNA were purified by agarose gel electrophoresis and electroelution before cloning. All other plasmids and relevant constructs are described in Table 4.

TABLE 4

PLASMIDS

| Plasmid | Relevant Genotype/Characteristics |
|---|---|
| pDTG514 | pGem3Z with a 2.75 kb EcoRI-SmaI fragment from pDTG350 containing the tod promoter, $P_{tod}$, $Ap^R$ |
| pUCD615 | Promoterless luxCDABE cassette, ori pSa, ori pBR322, $Ap^R$, $Km^R$ |
| pKK223-3 | Expression vector containing the 5S ribosomal terminator rrnB $T_1T_2$ |
| pBSKS | pBluescript IIKS+ with multicloning site (MCS) KpnI-SacI, $Ap^R$ |
| pBSMCS(−) | pBluescript without the MCS (BssH II-BssH II fragment removed), $Ap^R$ |
| pLJS | pBSMCS(−) with added XbaI, NheI, AvrII and SpeI sites, $Ap^R$ |
| pLJS-tod | pLJS containing the 1.8 kb SmaI-Xho I tod promoter fragment from pDTG514, $Ap^R$ |
| pLJS-lux | pLJS containing the 8.35 kb KpnI-PstI luxCDABE cassette from pUCD615, $Ap^R$ |
| pLJST2 | pLJS containing the 0.77 kb HindIII-Hinc II fragment from pKK223-3 cloned into HindIII-SmaI site, $Ap^R$ |
| pUC18 Not | Cloning vector containing multicloning site flanked by NotI sites, $Ap^R$ |
| pUC18 Not-lux | Contains the 8.35 kb XbaI-Pst I fragment from pLJS-lux, $Ap^R$ |
| pUCI8 Not-todlux | Contains the 1.8 kb SpeI-XhoI fragment from pLJS-tod, $Ap^R$ |
| pUT | 5.2 kb cloning vector containing mob RP4, ori R6K and Tn5 tnp lacking NotI sites, $Ap^R$ |
| pCR™II | 3.9 kb cloning vector for PCR™ products with 3′ A overhangs, $Ap^R$, $Km^R$ |
| pUTK209 | pCR™ II containing mini-Tn5KmNX with unique NotI and XbaI sites, $Ap^R$, $Km^R$ |
| pUTK210 | pUT containing mini-Tn5KmNX, $Ap^R$, $Km^R$ |
| pUTK211 | pUT/mini-Tn5KmT2 containing the 0.8 kb NotI-AvrII rrnB $T_1T_2$ fragment, $Ap^R$, $Km^R$ |
| pUTK214 | pUT/mini-Tn5Kmtod-lux containing the 10.2 kb NotI-XbaI fragment from pUC18 Not-todlux, $Ap^R$, $Km^R$ |

Electroporation

Electrocompetent cells were prepared as outlined by the manufacturer (BTX, San Diego, Calif.). Electroporations were performed using a BTX Electroporator 600 with the following conditions: 40 µl cells, 1 µl ligation mixture, a 2.5 kV pulse for about 4.7 ms using a 2 mm gap cuvette. After the pulse, cells were immediately resuspended in LB (to 1 ml) and allowed to recover for 1 h at 37° C. (200 rpm) before plating on LB plates with the appropriate antibiotic selection.

DNA Sequencing

The mini-Tn5KmNX in pCRII™ was sequenced to confirm that the site-directed mutagenesis was successful using both the forward and reverse sequencing primers for pCRII™. Sequencing was performed using an Applied Biosystems Model 373A (Foster City, Calif.).

Transposon Mutagenesis

E. coli S 17-1 (λpir) containing pUTK214 was mated into P. putida F1 by plate mating. Donor and recipient cells were mixed in a ratio of approximately 5 to 1, spotted onto LB plates and incubated at 25° C. for 24 h. Mutants were selected on Pseudomonas isolation agar supplemented with 50 µg/ml kanamycin. Colonies were subsequently subcultured to grid plates and exposed to toluene vapor. Colonies which produced light were grown in mineral salts media (MSM) (Stanier et al., 1966) with toluene vapor to ascertain whether or not the transposon had inserted into a required gene for the cell. The strains were also evaluated for their performance as bioreporters in liquid growing cell assays (Heitzer et al., 1992).

Confirmation of Transposition

The selected strain was subjected to DNA:DNA hybridization to verify transposition as opposed to recombination by using a $^{32}P$-labeled probe specific for the Tn5 transposase (tnp) contained on pUT. Equal target amounts of luxA, todC and tnp DNA were loaded onto a Biotrans™ nylon membrane (ICN, Irvine, Calif.) using a Bioslot blot apparatus (Biorad, Hercules, Calif.) according to the manufacturer's protocol. The blot consisted of chromosomal DNA from F1, TVA8 and the aforementioned controls. The DNA was loaded in triplicate and the blot was subdivided and each separate blot was hybridized with either luxA, todC, or tnp PCR™-generated $^{32}P$-labeled DNA probes. Blots were hybridized and washed as previously described (Applegate et al., 1997).

Stability Assays

Batch stability assays were performed by transferring 1 ml of a 100 ml overnight culture grown on LB with 50 µg/ml kanamycin ($Km_{50}$) to a 250 ml Erlemeyer flask using toluene as a sole carbon source as described for the growth curves. One ml of culture was transferred every day for five days to flasks with 100 ml MSM supplied with toluene vapor (without Km). Assays were performed in triplicate. Before each transfer, cells were plated on selective ($LBKm_{50}$) and non-selective media (LB) to ascertain loss of kanamycin-resistance resulting from deletion or excision of the transposon. Colonies were subjected to colony hybridization using a 295 bp luxA DNA probe (Johnston, 1996).

Stability was also assayed in continuous culture using a New Brunswick Bio Flow fermentor (Edison, N.J.) with a 370 ml vessel operated at 28° C. at 180 rpm. The feed consisted of MSM supplemented with toluene at approximately 100 mg/L at a flow rate of 1.0 ml/min. This was accomplished by simultaneously adding toluene saturated-MSM at a flow rate of 0.2 ml a min and MSM at a flow rate of 0.8 ml a min using FMI metering pumps (Oyster Bay, N.Y.). The chemostat was maintained at 28° C. using a cold finger and a refrigerated circulating water bath (Brinkman, Westbury, N.Y.). The chemostat was operated for 14 days, which corresponded to about 100 generations. Monitoring for both bioluminescence and optical density was performed daily. Cells from the chemostat were also plated every 7 days and colony hybridizations were performed as described previously.

Growth Curves

Growth curves of TVA8 and F1 were obtained by growing cells in 100 ml MSM with toluene vapor supplied as a sole carbon source in 250 ml Erlemeyer flasks. Cultures were started from a fresh overnight culture, grown to an $ODS_{546}$ of 1.0 in 100 ml of LB and washed twice in 100 ml MSM and resuspended in 100 ml of media. A one ml aliquot of this suspension was added to the toluene flasks. The cultures were shaken at 200 rpm at 28° C. and sampled approximately every hour. The $OD_{546}$ was measured for each culture and rates of increase in optical density were determined from the linear portion of the curves.

Bioluminescence Sensing

Bioluminescent assays were conducted as described by Heitzer et al. (1992). An overnight culture from a frozen stock of TVA8 was prepared in a 250 mL Erleumeyer flask containing 100 mL LB with 50 µg/ml kanamycin. A subculture was prepared in yeast extract-peptone-glucose media (YEPG), grown to an $OD_{546}$ of 0.35-0.45 and assayed every 30 min. In preliminary studies, an incubation time of 2 hours was shown to provide a consistent light response which maximized the signal intensity. After 2 hours, the final $OD_{546}$ was measured and values are expressed as specific bioluminescence (namp/$OD_{546}$).

Test Sample Preparation

An aqueous solution of JP-4 jet fuel constituents was prepared by adding JP-4 to sterile deionized water in a 1 to 10 jet fuel to water ratio. The solution was shaken on a rotary shaker for 24 hours. After phase separation, aqueous phase aliquots were added to test vials. Test solutions of toluene, benzene, ethylbenzene, phenol and isomers of xylene were prepared as above.

Bioluminescence Measurements

Sample vials were placed in a light-tight box and the light output was measured using a liquid light pipe and an Oriel photomultiplier and digital display (Model 77340 and Model 7070, Stratford, Conn.), using 25 mL scintillation vials were used. Bioluminescent readings were taken every 30 minutes. Light measurements for growth curves and the chemostat were measured as above with the exception that the light-tight box was modified to hold a cuvette allowing for light measurement after OD readings.

Results

Strain Construction

Figure 10:
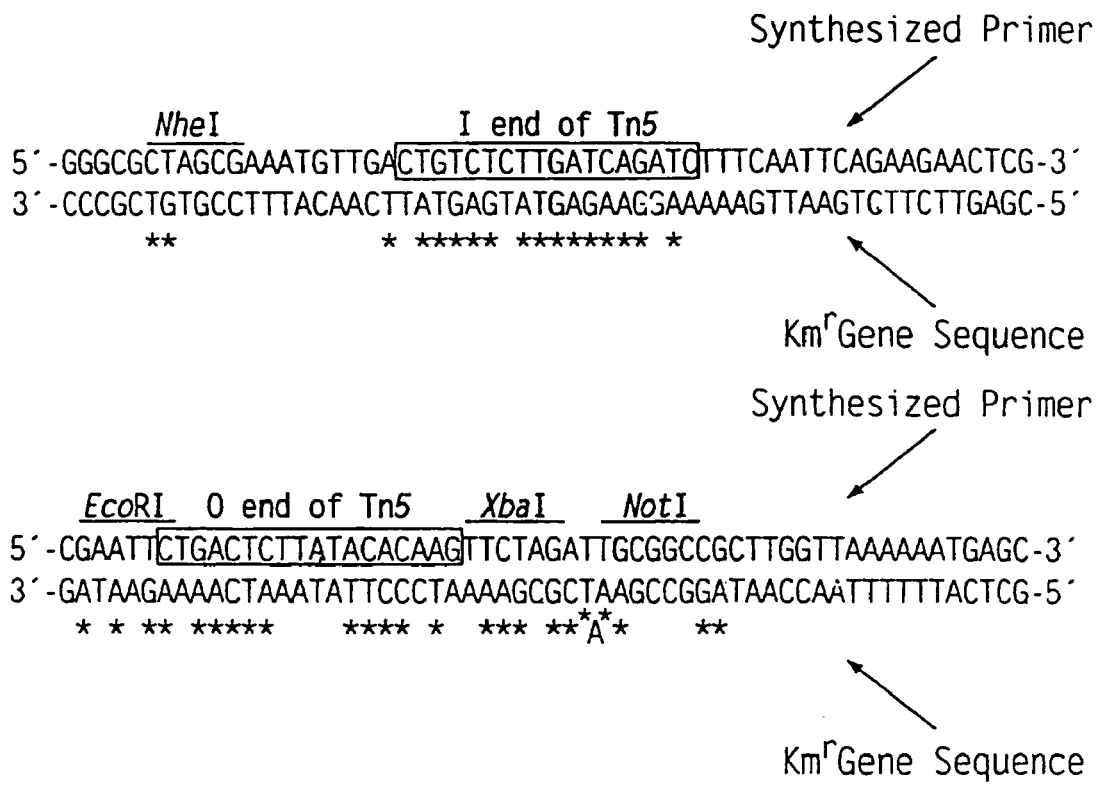
FIG. 10 shows the sequence of primers (SEQ ID NO's.: 1-8) used in site-directed mutagenesis to generate the modified mini-Tn5 and the cloning vector, pLJS. Asterisks denote mismatches between the primer and the target sequence. *A* denotes an extra adenine which was inadvertently synthesized.
Figure 10:
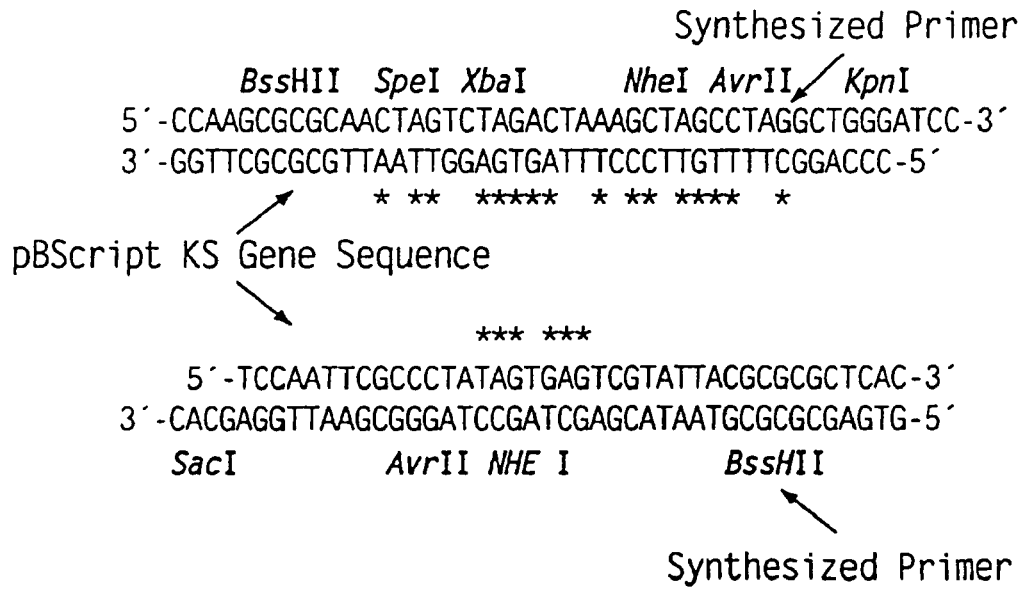
Figure 11:
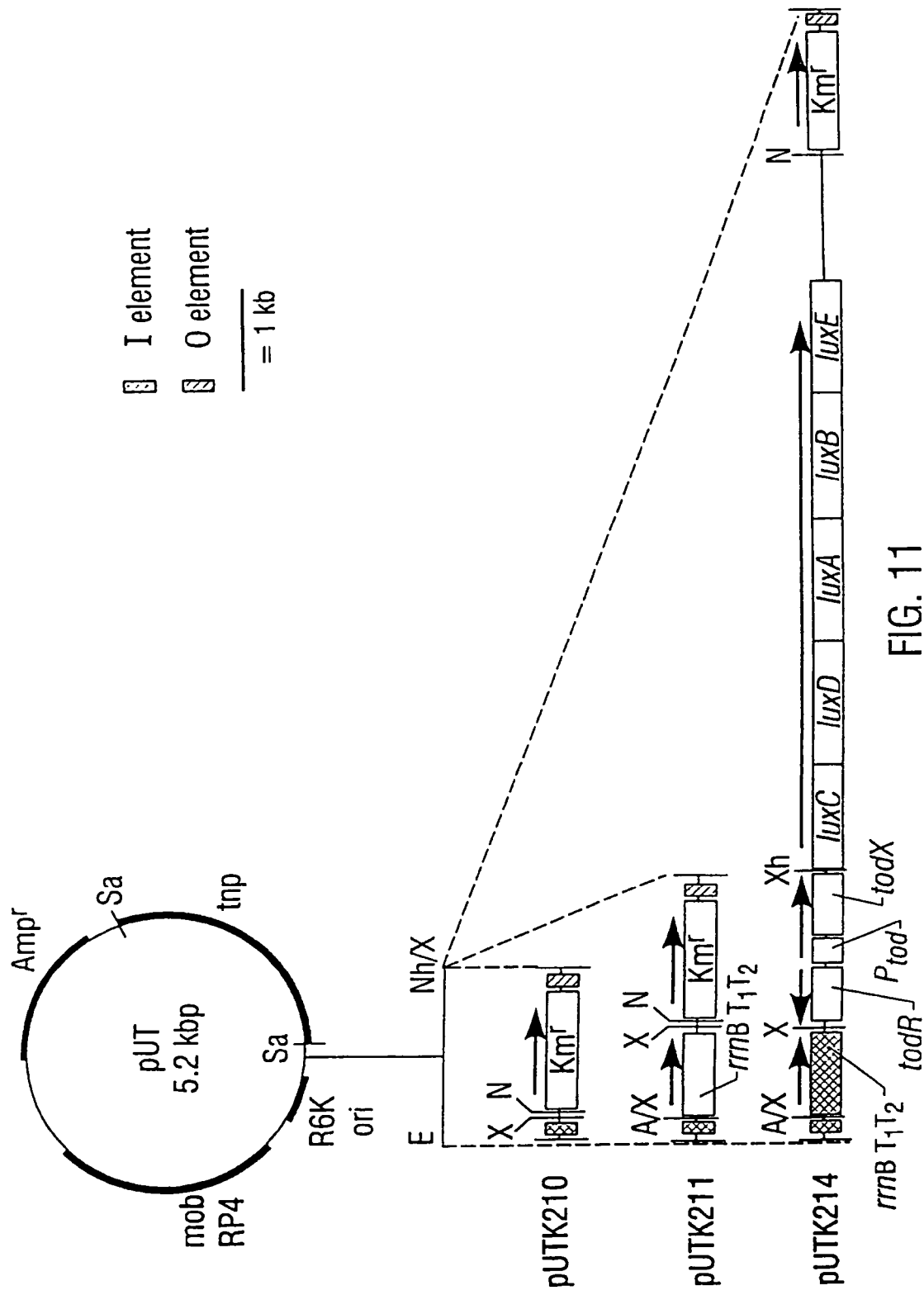
FIG. 11 shows a diagram for the construction of the mini-Tn5Kmtod-lux. A/X and Nh/X represent AvrII-XbaI and NheI-XbaI heterologous cloning sites, respectively. Abbreviations: N, NotI; Sa, Sal I, X, XbaI.
Figure 12:
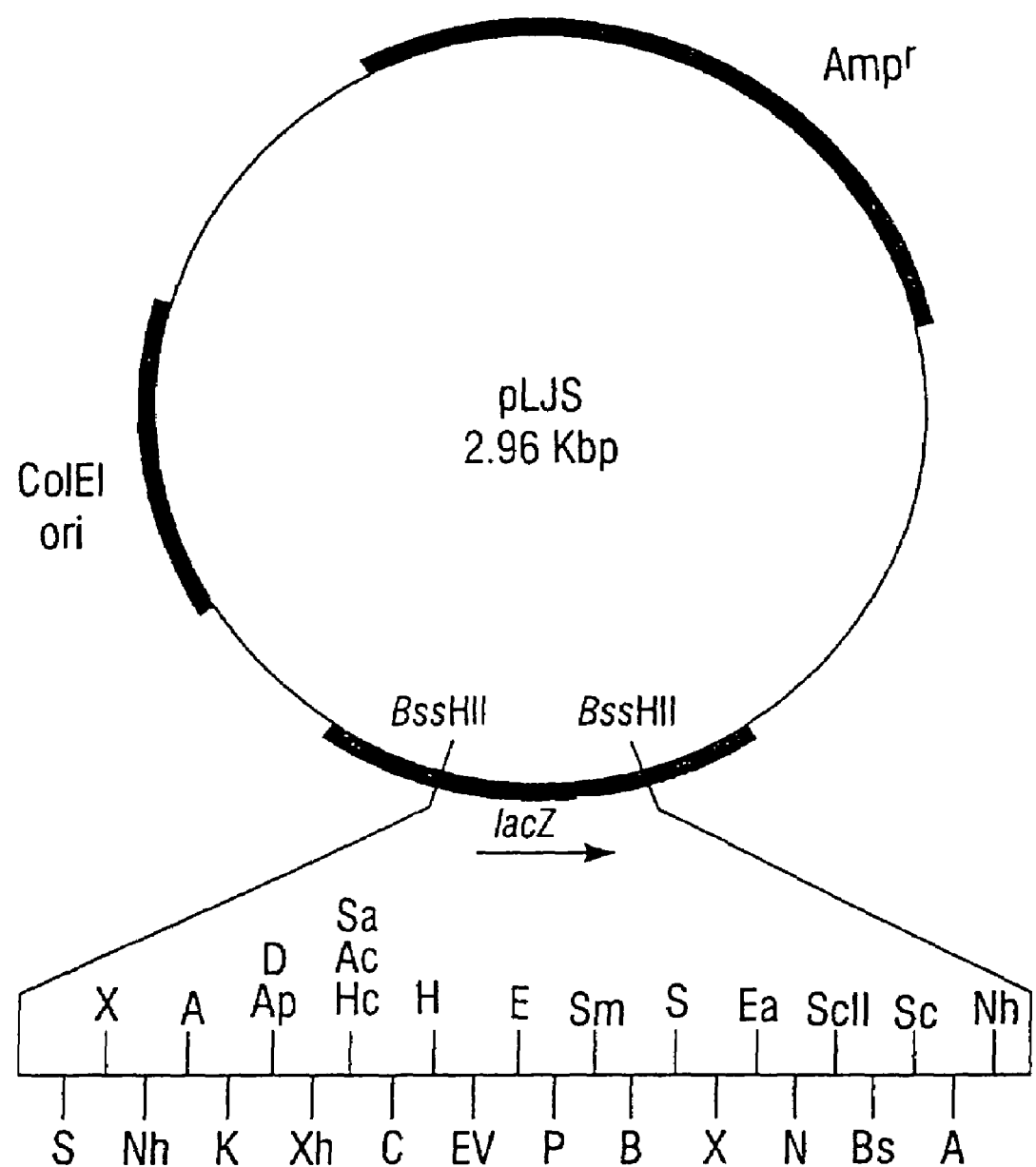
FIG. 12 shows the cloning plasmid pLJS with unique restriction sites. Abbreviations: A, AvrII; Ac, Acc I; Ap, Apa I; B, Bam HI; Bs, Bst XI; C, Cla I; D, Dra II; E, Eco RI; Ea, Eag I; EV, Eco RV; H, HindIII; Hc, Hinc II; K, Kpn I; N, NotI; Nh, NheI; P, Pst I; S, SpeI; Sa, Sal I; Sc, Sac I; Sc II, Sac II, Sm, SmaI; X, XbaI, Xh, Xho I.

Sequence analysis of the resultant mini-Tn5KmNX showed that both the I and O insertion sequences were identical to the primers that were used to generate the transposon (see FIG. 10). The extra adenine that was mistakenly added did not affect the construct. The plasmid pLJS (FIG. 12) was also sequenced to confirm that the added sites were incorporated and to determine the integrity of the multicloning site (MCS). Sequence data showed that the MCS and all of the added sites were intact. The resultant cloning vector also maintained the ability for α-complementation. A schematic representation of the mini-Tn5KmNX construction and the final construct mini-Tn5Kmtod-lux can be seen in FIG. 11.

The S 17-1 (λpir) strain of *E. coli* harboring mini-5Kmtod-lux was mated with F1 and resultant mutants were screened for their ability to produce bioluminescence when exposed to toluene. Fourteen strains were evaluated for their ability to grow on toluene MSM and number 8 was chosen and designated TVA8. The strain was examined to confirm that it was a result of a transposition event and not a recombination event. DNA:DNA hybridization showed that TVA8 contained the lux genes but did not show hybridization with tnp. Blots hybridized with tnp were re-probed with todC to verify that DNA was present. The negative transposase result confirmed that transposition had occurred.

Stability of TVA8

In stability studies with batch and continuous cultures, the transposon insertion in F1 appeared to be stable. Plate counts from selective (LBKm$_{50}$) and non-selective media (LB) were compared to determine whether the kanamycin marker was being lost, and colony blots were subsequently hybridized with luxA probe to confirm that all colonies contained the lux transposon insert (and were not contaminants). For the succinate chemostat without antibiotic selection, the selective plate counts were approximately five percent lower than the non-selective plate counts after 10 days, however, 100% of colonies from both plate types were lux-positive. In batch stability studies with toluene vapor supplied as sole carbon source, TVA8 did not demonstrate instability when subjected to the same evaluation. The selective:non-selective plate count ratio was 1.12±0.13 after 5 daily transfers, and all colonies hybridized with the luxA probe. Similar results were observed for TVA8 stability under continuous culture conditions with toluene supplied at approximately 100 mg/L. After a 14 day period (approximately 100 generations), the selective:non-selective plate count ratio was 1.05±0.13 and all colonies from selective and non-selective plates were lux-positive.

Figure 13:
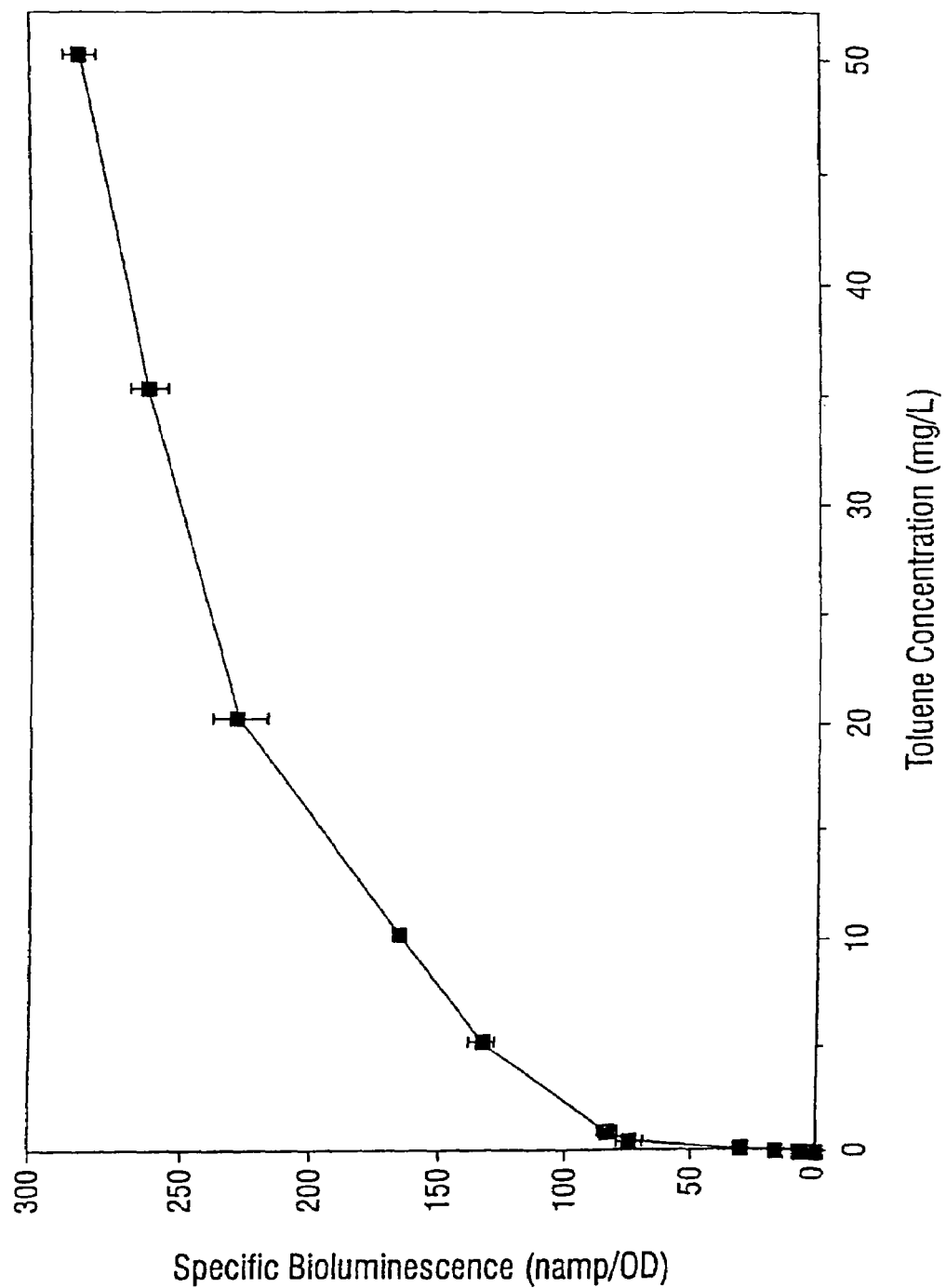
FIG. 13 shows the bioluminescence response of TVA8 to increasing concentrations of toluene after 2 h exposure. Values are averages of three replicates and have been normalized to the cell density ($OD_{546}$).

Quantitative response of Tod-Lux Reporter Strain to Toluene, BTEX Compounds and JP-4 Jet Fuel An increase in bioluminescence response for increasing toluene concentrations was observed (see FIG. 13). The bioluminescence response to toluene concentration over the range, 5 to 20 mg/L was linear with specific bioluminescence values of 133 to 228 namp/$OD_{546}$. The fold increase in light response for concentrations above 20 mg/L was less, showing 290 namp/$OD_{546}$ for 50 mg/L. The overall bioluminescence response curve showed a Michaelis-Menten (enzyme kinetics) shape, showing saturation at higher inducer concentrations. The toluene detection limit was determined to be less than 50 µg/l.

TVA8 was examined for its bioluminescence response to BTEX compounds as well as phenol and water-soluble JP-4 jet fuel components. There was a significant light response to benzene, m- and p-xylenes, phenol and JP-4 (Table 5) as well as to toluene. The same concentrations of toluene and benzene (50 mg/l) resulted in a similar light response. There was no increase of bioluminescence upon exposure to o-xylene. The light response due to JP-4 was significantly greater than the additive responses for JP-4 components (i.e. BTEX compounds) present at their estimated concentrations (Smith et al., 1981). The increased response may be the result of induction due to other components of JP-4 which were not tested. A significant light response was observed for ethylbenzene after 4 hours. After 2 hours incubation, the cell densities for the ethylbenzene treatments were significantly less than the other samples, indicating that there may have been a toxicity effect. Other studies showed that 50 mg/L ethylbenzene would induce the bioluminescence response without a lag period when cells were previously grown on ethylbenzene and then subjected to growing cell assays.

TABLE 5

EFFECT OF BTEX, PHENOL AND JP-4 CONSTITUENTS
ON THE BIOLUMINESCENCE RESPONSE OF TVA8

| Treatment[a] | Exposure Time (hours) | Specific Bioluminescence (namp/OD)[b] |
|---|---|---|
| Buffer (Control) | 2 | 0.2 ± 0.1 |
| Toluene | 2 | 291 ± 6 |
| Benzene | 2 | 242 ± 9 |
| Ethylbenzene | 2 | 1.0 ± 0.2 |
|  | 4 | 47 ± 6[c] |
| o-xylene | 2 | 0.5 ± 0.1 |
| m-xylene | 2 | 38 ± 3 |
| p-xylene | 2 | 24 ± 2 |
| Phenol | 2 | 70 ± 2 |
| JP-4 | 2 | 93 ± 4 |

[a]Final concentration for BTEX and phenol treatments was approximately 50 mg/L, added as a hydrocarbon-saturated MSM solution. The final percentage of water-soluble JP-4 constituents was approximately 2%.
[b]Values are averages ± standard deviation of three replicate samples. Values were normalized to the final cell density ($OD_{546}$).
[c]Value for the 4 hour reading was that measured from a similar but separate study.

Toluene Growth Comparison of Bioluminescent Reporter with F1

Figure 14:
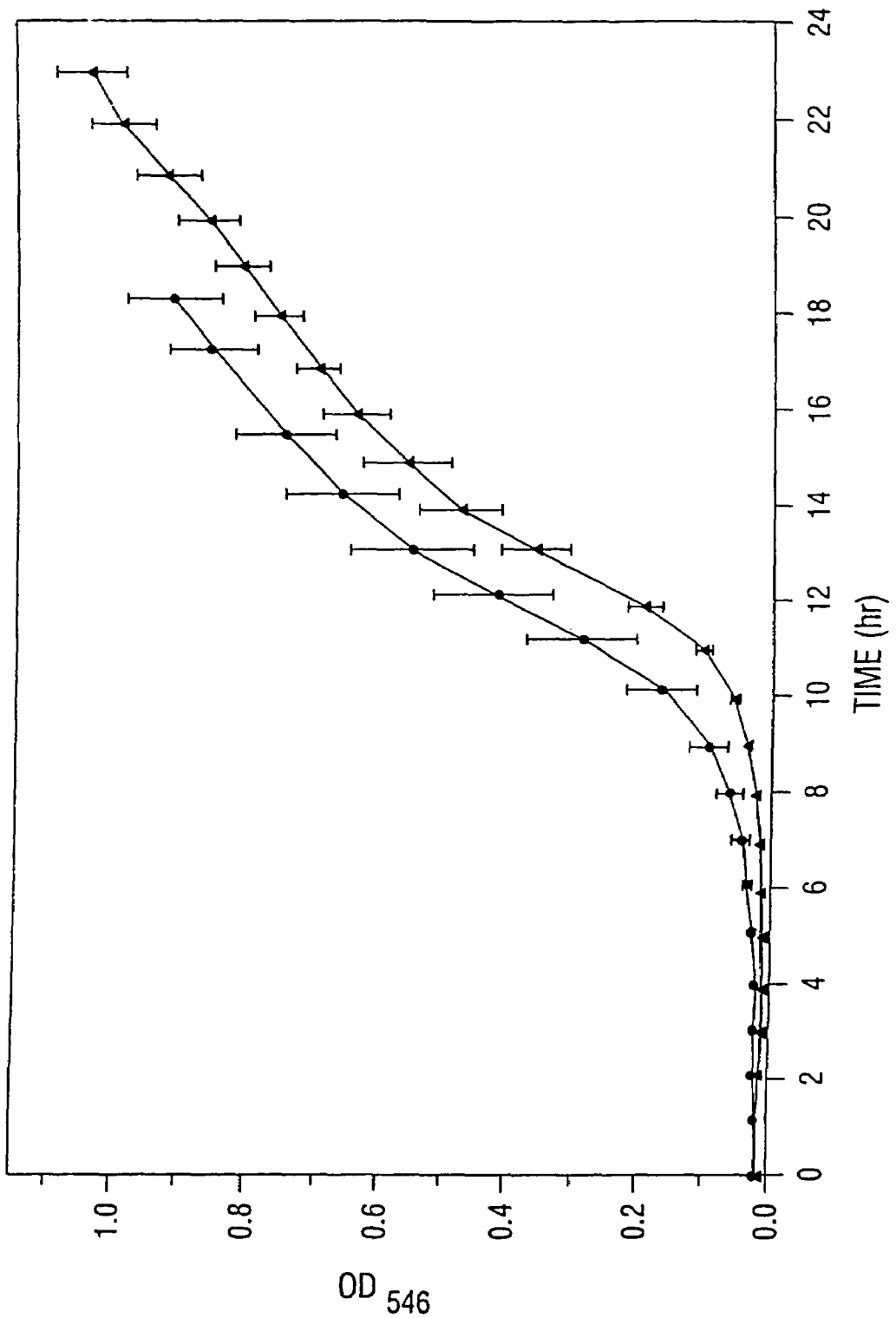
FIG. 14 shows growth curves for batch cultures of TVA8 (circles) and F1 (triangles) grown on MSM with toluene vapor. Values are averages of three replicates and error bars represent one standard deviation.

Growth curves for TVA8 and the parent strain, F1 on toluene vapor are shown in FIG. 14. The curves show similar shapes with different lag times for TVA8 and F1 which can be attributed to slightly different inoculum concentrations. Rates were computed from the slopes of the linear portion of the growth curve for both strains. The average rate of increase in optical density for F1 and TVA8, 2.14±0.3 and 2.2±0.3 $min^{-1} \times 10^{-3}$, respectively, were not statistically different ($\alpha=0.05$). These results demonstrate that the bioluminescence reactions do not appear to affect cell growth.

Figure 15:
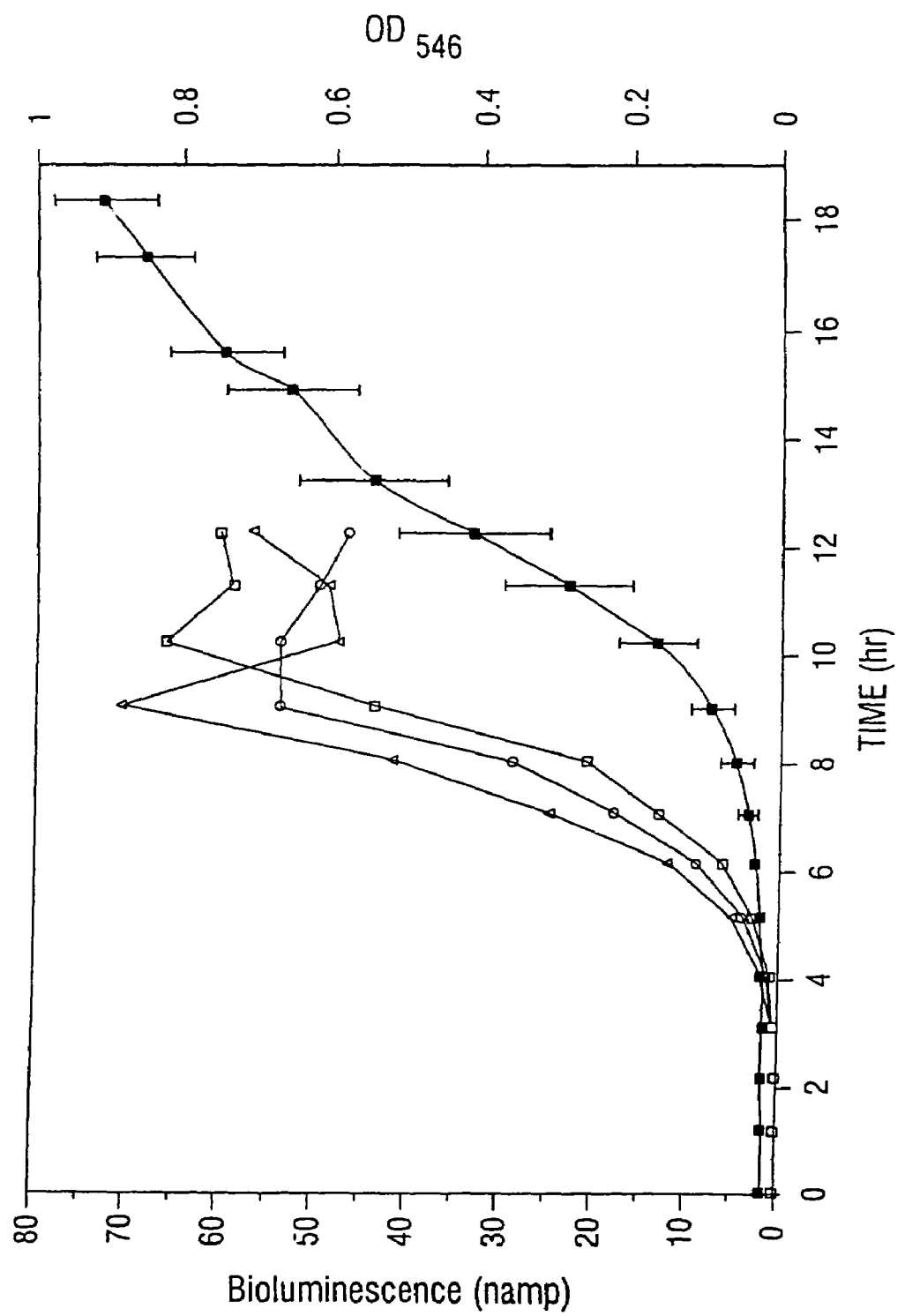
FIG. 15 shows a bioluminescence and growth of TVA8 on toluene vapor under batch conditions. O,□, Δ represent individual replicates of bioluminescence readings over time. The closed squares represent the average optical density at 546 nm ($OD_{546}$) of three replicates.

Bioluminescence of TVA8 was measured during growth on toluene and is shown along with the cell density data in FIG. 15. The bioluminescence plots show a similar trend to the TVA8 growth curve, although, they are shifted to earlier time points. The graph shows that there is a definite correlation between an increase in biomass and an increase in light production. At higher cell densities, cells likely became limited for oxygen resulting in decreased bioluminescence values.

Advantages of the Chromosomally Inserted Tod-Lux System

The majority of bioluminescent reporters currently being used are the result of cloning a promoter in front of the promoterless luxCDABE gene cassette in pUCD615 and transferring the plasmid construct into the strain which contained the particular promoter. Plasmid-based systems have obvious drawbacks such as the need for constant selective pressure to ensure plasmid maintenance as observed by Rice et al. (1995). Another important consideration is that of plasmid copy number. If the system is positively regulated, copy number can negatively effect gene expression. Multiple copies of the promoter binding region for the regulatory protein on the plasmid compete with the binding site on the chromosome causing less expression of the operon being studied (Lau et al., 1994). This negative effect is important when using lux fusions for on-line monitoring of bacterial processes.

Another strategy used in the construction of bioluminescent reporters is the use of the lux transposon Tn4431 (Shaw et al., 1988). The desired reporter strain is transposon-mutagenized and constructs are selected for bioluminescence upon addition of the specific inducer as in the case of the nah-lux reporter HK44 (King et al., 1990). However, a problem with creating a lux fusion by transposon insertion is that the pathway in which insertion occurs is usually disrupted. For example, in HK44 the lux insertion disrupted nahG (salicylate hydrogenase) and therefore the strain was no longer able to mediate the complete degradation of naphthalene via the nah and sal pathways (Menn et al., 1993). To develop a strain for use in monitoring naphthalene degradation, the reporter plasmid had to be conjugated with another strain able to complete the metabolism of naphthalene. Due to these concerns, researchers have shifted to using transposon delivery systems.

Herrero et al. (1990) constructed a mini-Tn5 delivery system which consisted of a mini-Tn5 transposon with unique NotI and SfiI restriction sites and a pUC derivative containing either of these two restriction sites flanking the multicloning site. The transposase was provided in trans to provide stability in the final construct. The approach involved sub-cloning the relevant insert into the particular pUC derivative, cloning it into the mini-Tn5 vector and transposing it into the chromosome of the strain of interest. One drawback to this system is that it is limited to NotI and SfiI sites and if either of these two enzymes cut within the insert DNA, alternative strategies have to be pursued. Furthermore, it may be difficult to non-directionally clone a large DNA fragment such as greater than 12 kbp.

The system described herein is a modification of that described previously. The mini-Tn5 system constructed in this study is based on the use of five enzymes, AvrII, NheI, SpeI XbaI and NotI, as opposed to two. Mini-Tn5KmNX contains unique NotI and XbaI sites which allow directional cloning of inserts, negating dephosphorylation of the vector DNA. The final version of the mini-Tn5 derivative, pUTK211 also contains a strong transcription terminator 5' to the unique cloning sites to insure that there is no read-through transcription from a gene in which the transposon has been inserted. The cloning vector pLJS used in conjunction with mini-Tn5KmNX allows the utilization of a large region of the multicloning site flanked by AvrII, NheI, SpeI, XbaI and NotI on one side and AvrII, NheI, SpeI and XbaI on the other. If there is a NotI site in the fragment to be cloned, the XbaI site can be used for non-directional cloning. The restriction recognition sequences for these enzymes are rare (6-base sequences with the exception of NotI which recognizes an 8-base sequence). The advantage of the XbaI site is that it allows the heterologous cloning of AvrII, NheI and SpeI since all of these enzymes have the same 5' overhang, CTAG. This system also allows the assembly of larger inserts as seen by the cloning of the transcription terminator destroying the XbaI site by heterologous cloning using AvrII. The resultant cloning step also regenerated the unique XbaI site. One can use this heterologous cloning strategy of destroying and regeneration of the unique XbaI site to assemble different DNA fragments for the desired construct. Using this system, P. putida TVA8, a chromosomally-encoded tod-lux bioluminescent reporter was constructed.

TVA8 was capable of growing on mineral salts media with toluene or succinate demonstrating that the transposon insertion did not disrupt a gene necessary for growth. This is a crucial check that must be performed to ascertain the overall fitness of the strain before further evaluation. Furthermore, TVA8 did not show loss of the transposon insertion or loss of bioluminescence after 100 generations in continuous culture or 5 successive transfers in batch culture.

These results suggest that selective pressure is not necessary for the integrity of the strain. This stability is important since it eliminates the need for antibiotic selection, which if required would exclude the use of this bioreporter in situ. The strain also was compared to the wild type strain F1 to ascertain whether or not the bioluminescent reporter was a significant metabolic drain on the cell, as well as if the site of transposition was a hindrance to the cell. Growth of TVA8 and F1 on toluene vapor showed that there was no difference in growth between the two strains, suggesting that neither the insertion nor the reporter was a significant handicap to the cell.

The tod-lux reporter is quite sensitive with a detection limit below 50 μg toluene/L. The bioluminescence value at this concentration was 80-fold greater than the background bioluminescence level. This bioreporter showed a very low background level of bioluminescence (less than 1 namp/$OD_{546}$). TVA8 was shown to be useful for quantifying toluene present at low concentrations in aqueous solutions. Significant light levels were observed for very low optical densities (FIG. 15).

TVA8 may be described as a generalized BTEX bioreporter rather than simply a toluene bioreporter since it was responsive to benzene, ethylbenzene and m- and p-xylene as well. Since all of these compounds induce the bioluminescence response, TVA8 may be used as a bioreporter for JP-4 jet fuel contamination or presence of any fuel which contains BTEX compounds. The strain may be used for on-line monitoring of TCE cometabolism since the lux and tod operons are under the same regulation, and the toluene dioxygenase also catabolizes TCE. Bioluminescent reporters may have great potential for field use applications since they can provide on-line and non-destructive analyses of gene expression as well as detection of chemical contaminants. The development of stable transposon insertion of reporter genes into environmental isolates expands the utility of bioreporter strains for in situ sensing of gene expression.

Example 2

*Pseudomonas putida* B2: A Tod-Lux Bioluminescent Reporter for Toluene and Trichloroethylene Co-Metabolism The environmental fate and bioremediation potential of trichloroethylene (TCE) have received considerable attention due to its extensive production, use, and occurrence as a groundwater priority pollutant of toxic and carcinogenic concern. Bacterial metabolism of TCE has been extensively reviewed (Ensley, 1991). TCE degradation is co-metabolic in that TCE is not used as a carbon source but is fortuitously degraded. Due to the potential production of carcinogenic vinyl chloride during anaerobic degradation, much of the recent focus on TCE biodegradation has been on aerobic, oxygenase-mediated TCE co-metabolism. Substantial information has been developed on monooxygenase-mediated co-metabolism of TCE with particular emphasis on the methane monooxygenases and a variety of toluene monooxygenases.

Toluene degradation occurs via catabolic pathways containing both monooxygenases and dioxygenases, which have the ability to oxidize TCE. The toluene dioxygenase (todC1C2BA) contained in *Pseudomonas putida* F1 is also capable of transforming TCE.

Central to the use and further development of aerobic co-metabolic TCE bioremediation is the ability to monitor, control and optimize such biodegradative processes. One such strategy has been the development of bioluminescent lux gene fusions for use in on-line reporter technology (King et al., 1990). The use of lux-reporter systems in the study of the on-line monitoring of naphthalene degradation has been well documented (Heitzer et al., 1995). These reporter systems have also been used to assess the bioavailability of pollutants to catabolic organisms.

This example describes the construction of lux bioreporters for monitoring and optimizing the co-metabolic oxidation of pollutants such as TCE. For this purpose the tod system contained in *P. putida* F1 was chosen to develop a tod-lux gene fusion to monitor the expression of toluene dioxygenase.

Materials and Methods

Strain Construction

The strains and plasmids used in this example are shown in Table 6. *Escherichia coli* was grown in Luria-Bertani (LB) broth and on LB agar plates at 37° C. *Pseudomonas putida* F1 was grown on yeast extract-peptone-glucose (YEPG) medium consisting of 0.2 g yeast extract, 2.0 g polypeptone, 1.0 g D-glucose and 0.2 g ammonium nitrate (pH 7.0) in 1 L of distilled water at 28° C.

TABLE 6

STRAINS AND PLASMIDS

| Strain | Plasmid | Relevant Characteristic(s) |
| --- | --- | --- |
| *E. coli* JM109 | pDTG514 | pGem3Z with a 2.75-kb EcoR1-SmaI fragment from pDTG350 containing the tod promoter, Amp ® |
| *E. coli* HB101 | pUCD615 | Promoterless luxCDABE cassette, mob$^+$ Amp$^R$, Km$^R$ |
| *P. putida* F1 | none | Contains chromosomally-encoded tod operon for toluene degradation |
| *P. putida* B2 | pUTK30 | tod-lux reporter containing the tod promoter fragment inserted upstream of the promoterless luxCDABE cassette, Amp$^R$, Km$^R$ |
| *E. coli* DF1020 | pRK2013 | Helper plasmid, Amp$^R$, Km$^R$, Tra$^+$ |

Figure 16:
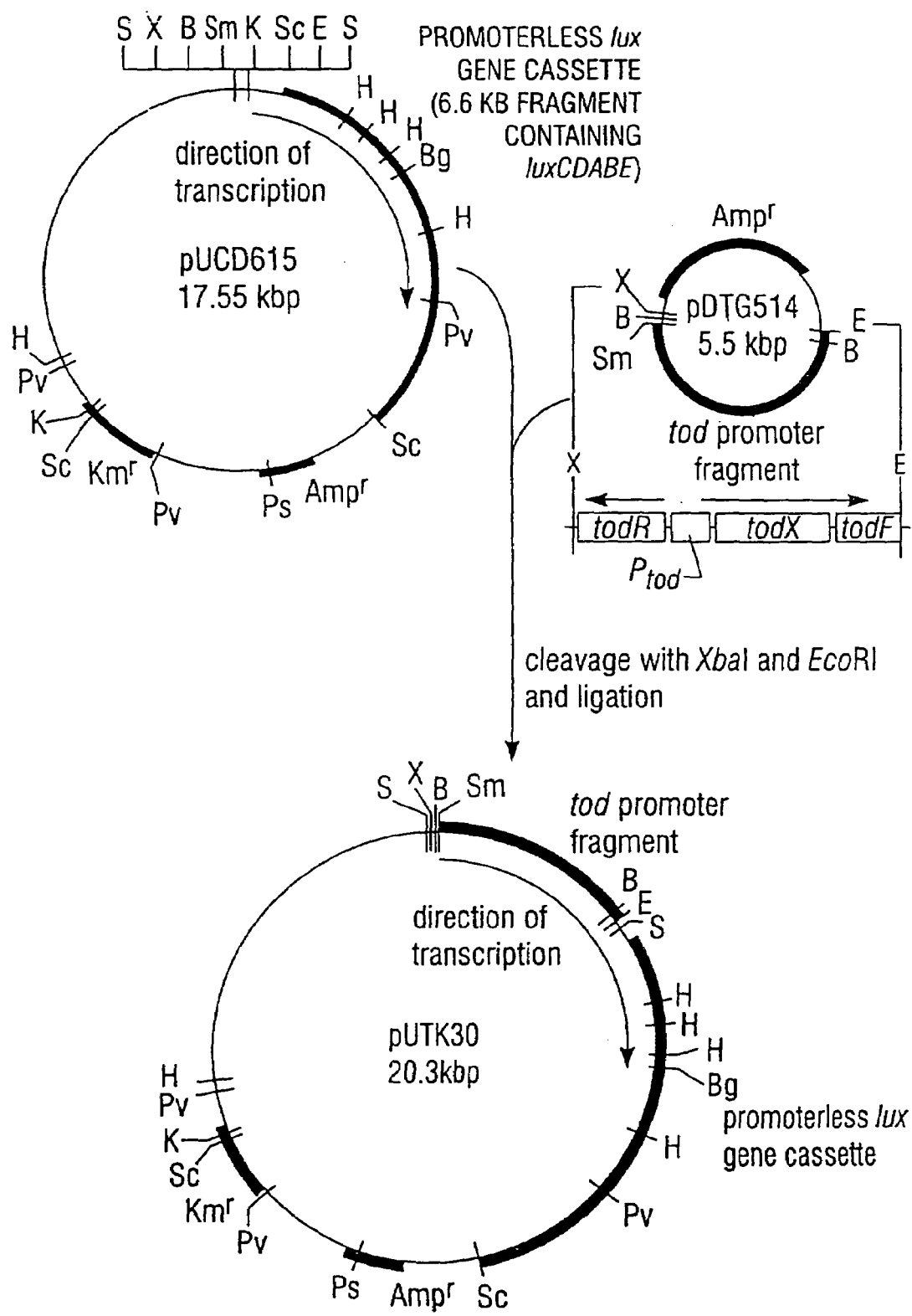
FIG. 16 shows the construction of the tod-lux reporter plasmid pUTK30. The 2.75-kb EcoR1-XbaI fragment from pDTG514 (Menn et al., 1991) was cloned in front of the promoterless lux gene cassette in pUCD615 (Rogowsky et al., 1987). Abbreviations: B, BamHI; Gb, BglII; E, EcoR1; H, HindII; K, KpmI; Ps, PstI; Pv, PvuII; Sc, SacI; S, SalI; Sm, SmaI; X, XbaI.

One-liter cultures of *E. coli* JM109 and HB101 harboring the appropriate plasmids were harvested and plasmid DNA was isolated using a modified alkaline lysis procedure (Promega, 1992). The plasmid DNA was subjected to CsCl density gradient purification, followed by butanol extraction and ethanol precipitation (Sambrook et al., 1989). Plasmid DNA was resuspended in TE buffer (10 mM Tris-base, 1 mM EDTA, pH 8.0) and stored at 4° C. until used. Restriction endonucleases and T4 DNA ligase were obtained from Gibco BRL (Gaithersburg, Md.) and used according to manufacturers' protocols. Cloning techniques were performed as outlined in Sambrook et al. (1989). The reporter plasmid pUTK30 was generated by cloning the tod promoter (Lau et al., 1994; Wang et al., 1995) from pDTG514 (Menn et al., 1991) in front of the lux gene cassette of pUCD615 (Rogowsky et al., 1987). This was accomplished by directionally cloning a 2.75-kb EcoR1-XbaI fragment from pDTG514 into an EcoR1-XbaI digest of pUCD615 (FIG. 16). Transformations were performed using subcloning efficiency competent cells (Gibco BRL, Gaithersburg, Md.) according to the manufacturer's protocol. Transformants were selected on LB plates containing 50 μg ml$^{-1}$ kanamycin. Plasmid minipreps of transformants were performed as described by Holmes and Quigley (1981) and cleaved with BamHI to confirm insertion of the tod fragment. The resultant *E. coli* strain, JBF-7 harbored the reporter plasmid pUTK30.

Triparental matings were carried out using a modified version of the filter technique. Pure cultures of donor (JBF-7, pUTK30), helper (DF1020, pRK2013; Figurski and Helsinki, 1979), and recipient (F1) were grown to an optical density at 546 nm ($OD_{546}$) of approximately 1.0 in LB broth with appropriate antibiotics. Cells were harvested by centrifugation at 9800×g for 10 min. The pellets were suspended and washed three times in 100 ml 50 mM $KH_2PO_4$ (pH 7.0), and suspended in 50 ml 50 mM $KH_2PO_4$.

The three strains were mixed using a ratio of 2:1:1 (donor/helper/recipient). The cell suspension as filtered through a Teflon membrane (47 mM, 022 µm pore size) and the filter was placed on a LB plate. After overnight incubation at 28° C., the filter was removed and washed in 1.5 ml 50 mM $KH_2PO_4$. Serial dilutions were performed and dilutions were plated onto *Pseudomonas* Isolation Agar plates (Difco, Detroit, Mich.). After a 48-hour incubation, toluene vapor was introduced and colonies which produced light were selected for further characterization. One of five kanamycin-resistant strains which emitted light in response to toluene vapor, *P. putida* B2, was chosen for use in the remaining studies.

Bioluminescence Analysis

In the batch and reactor studies, bioluminescence was measured using a photomultiplier, which converts the light to an electric current. The photomultiplier in the resting cell assays and the reactor system was connected to a computer and bioluminescence as namps current was recorded.

Batch Studies

Assays of growing cells were conducted as described by Heitzer et al. (1992). An overnight culture from a frozen stock of *P. putida* B2 was prepared in a 250-ml Erlenmeyer flask containing 100 ml LB and 50 µg ml$^{-1}$ kanamycin. A subculture was prepared and cells were used in mid-log phase ($OD_{546}$ of 0.45-0.48). A 2.5-ml aliquot was added to 2.5 ml mineral salts medium (MSM) containing 0-50 mg L$^{-1}$ toluene or 10-100 µl of JP4 jet fuel-saturated MSM. The concentration of toluene in water saturated with JP4 jet fuel is approximately 8 mg L$^{-1}$ (Smith et al., 1981). Bioluminescence was measured every 30 min.

Cells for resting cell assays were grown on MSM supplemented with 2.7 g L$^{-1}$ succinate. A culture of *P. putida* B2 was harvested at on $OD_{546}$ of approximately 0.8. The cells were centrifuged at 15000×g for 10 min, and resuspended in MSM to $OD_{546}$ of 0.6 four milliliters of culture were added to each of six 26-ml vials with Mininert valves (Dynatech, Chantilly, Va.) with stir bars. One vial was used for multiple toluene exposures, while the remainder were used for single exposures. The vials were magnetically stirred in a light-tight sampling cell. Toluene-saturated MSM and MSM alone were added to yield an $OD_{546}$ of 0.47, and 10 mg L$^{-1}$ toluene was injected six times over a 130-h period of the multiple-exposure vial. At the same time points, a single-exposure vial was injected with 10 mg L$^{-1}$ toluene. The light response was recorded every 3 min with a photomultiplier connected to a data acquisition computer.

Immobilized Cell Reactor System

*P. putida* B2 was encapsulated in alginate beads for the immobilized cell reactor system. Cells were grown in 1 L LB to an $OD_{546}$ of 1.2 and were centrifuged at 5500×g for 10 min, washed three times in 0.9% NaCl and suspended in 40 ml 0.9% NaCl. The cell suspension was added to 80 ml of an alginic acid solution (28 g L$^{-1}$ low viscosity alginate, 0.9% NaCl) (Webb, 1992). The cell-alginate suspension was placed in a 60-ml syringe, forced through a 25-gauge needle, and allowed to drop into a 0.5 M $CaCl_2$ solution. The alginate was cross-linked by the $Ca^{2+}$ ions, thus encapsulating the cells. The cells were subsequently placed in a fresh solution of 0.1 M $CaCl_2$ and allowed to sit for 30 min prior to use.

Figure 17:
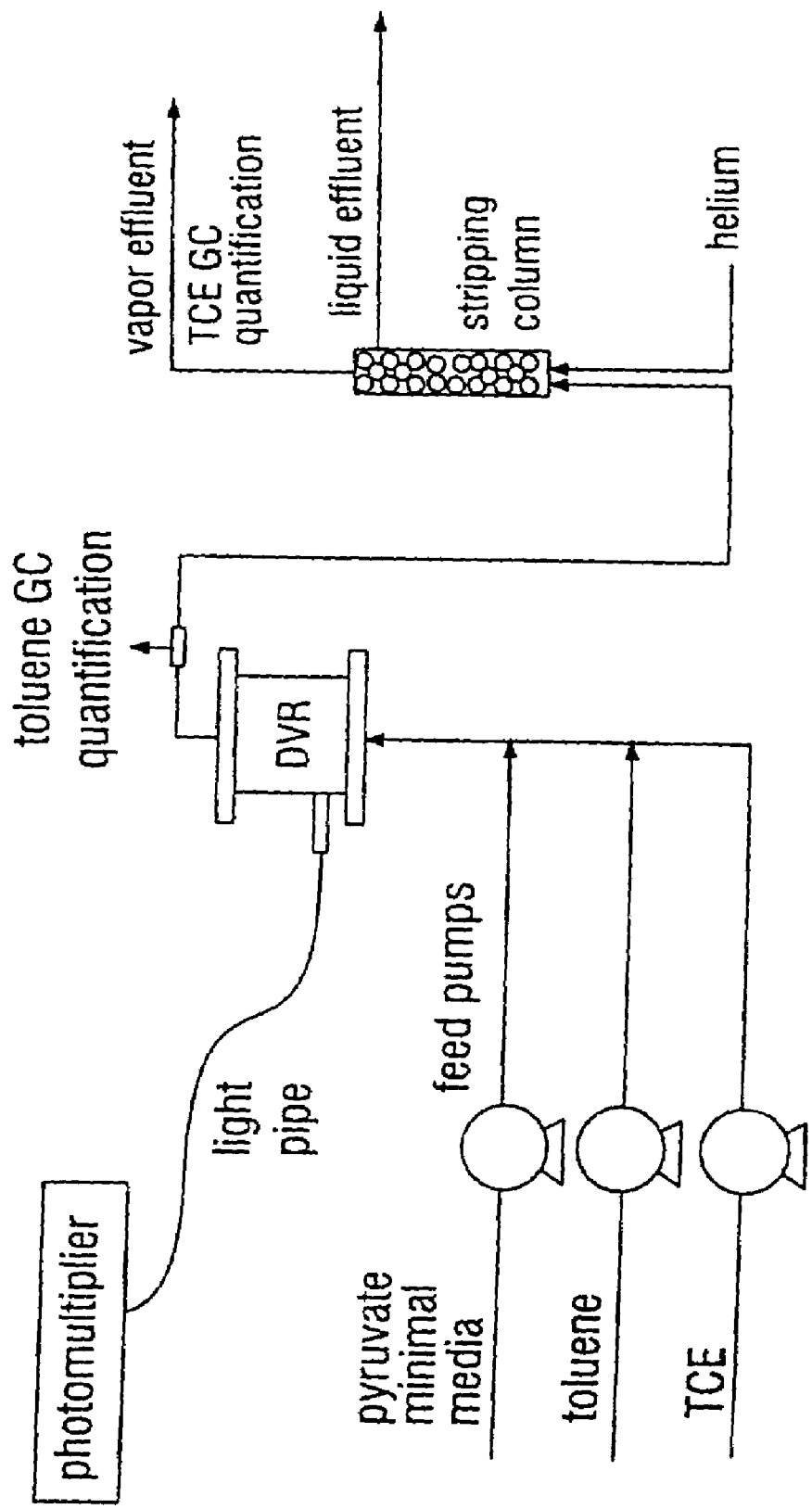
FIG. 17 shows a diagram of the on-line DVR system used to monitor the co-metabolism of TCE.

A differential volume reactor (DVR) was used to simulate a section of an ideal plug flow reactor. Influent to the reactor was dispersed through a porous metal frit to provide a flat velocity profile to the bed. The reactor measured 5.0 cm i.d.×5.0 cm long. A complete description of this reactor can be found in Webb et al. (1991). In this investigation, a system was designed incorporating the DVR as illustrated in FIG. 17. The system was equipped with three Millipore (Bedford, Mass.) stainless steel substrate containers rated to 690 kPa. The feed from the substrate vessels to the reactor inlet was controlled by two Filson (Middleton, Wis.) 301 HPLC pumps. A flow rate of 0.4 ml min$^{-1}$ was maintained. The substrate vessels were pressurized with oxygen to provide the system with an electron acceptor. All medium vessels contained trace mineral medium (Lackey et al., 1993) with the addition of 3 mg L$^{-1}$ pyruvic acid and a 0.1 M solution of Tris-base (pH 7.0). phosphate buffers were not used since phosphate ions complex with $Ca^{2+}$ ions and disrupt with alginate crosslinking. In addition to this medium, two of the vessels contained either TCE or toluene. The inlet concentration of toluene was altered by using square-wave perturbations with 20-h cycles (10 h with toluene, 10 h without toluene) using an HPLC pump controlled by a timer. During feed portions of the cycle, 10 mg L$^{-1}$ toluene was introduced into the inlet of the reactor. The inlet TCE concentration was constant at 20 mg L$^{-1}$.

TCE and Toluene Analysis

Analysis of TCE in the reactor effluent was performed online using a stripping column (12.5 cm length and 0.4 cm inner diameter) packed with 3-mm glass beads to provide adequate surface area for TCE separation. TCE was stripped with helium, the GC carrier gas. The stripping column outlet was attached to a gas chromatograph (GC, Hewlett Packard (Wilmington, Del.) (HP) 5890 Series II) with an electron capture detector by a heated sample line maintained at 75° C. Automatic injections (25 µl) were made by a computerized control process (HP Chem Station software). The GC was equipped with a cross-linked methyl silicone capillary column (length 30 m, i.d. 0.2 mm, 0.33-µm film thickness) while the oven was operated isothermally at 60° C. Other operating parameters included an injection temperature of 150° C., detector temperature of 200° C. and a split ratio of 10:1. This system was equipped with a bypass line around the reactor in order to calibrate the stripping column.

Toluene samples were removed at 0.5-ml aliquots from the effluent sampling port (FIG. 17) and injected into 1.5 ml sample vials. Headspace analysis was performed using a Shimadzu (Columbia, Md.) GC-9A gas chromatograph equipped with a 2.44-m, 3.2-mm diameter Poropak N packed column and a flame ionization detector. The isothermal temperature of the oven was 210° C., and both the detector and injector temperatures were 220° C.

Results

Batch Studies

Figure 18:
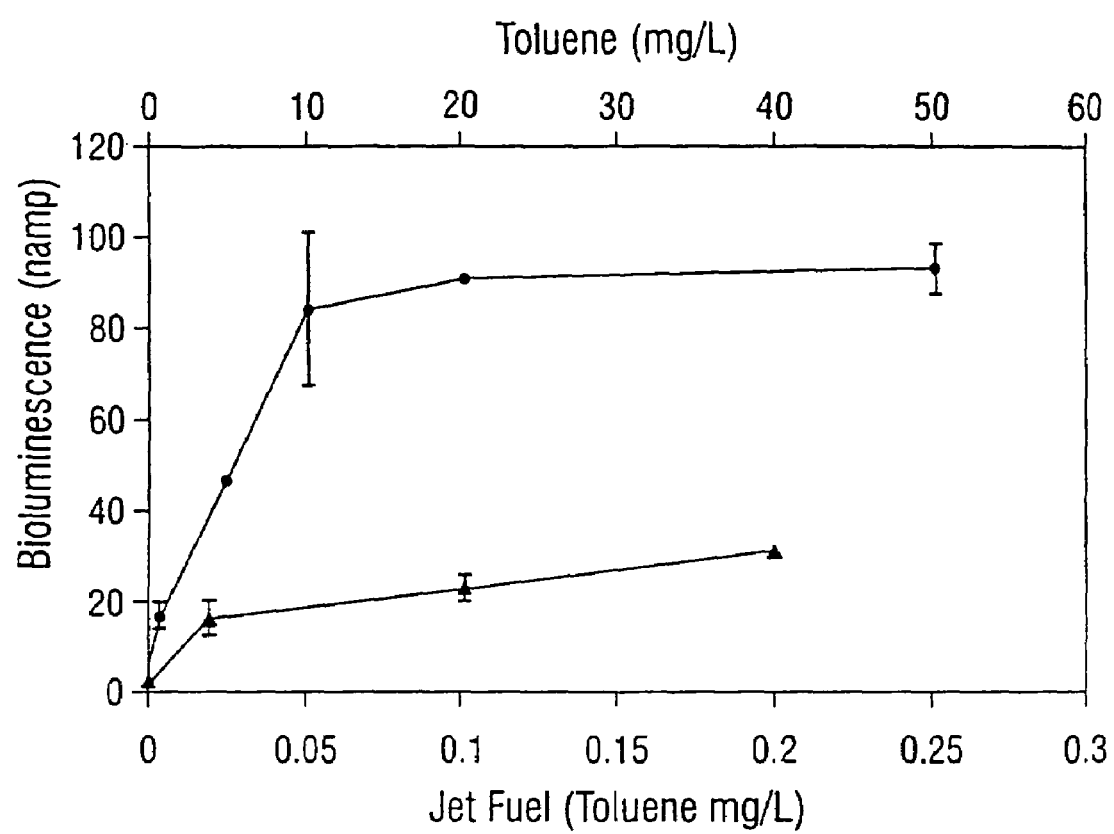
FIG. 18 shows bioluminescent response to varying concentrations of toluene (λ) and JP4 jet fuel, expressed as mg $L^{-1}$ toluene (σ) in growing cell assays after a 1.5-h exposure.

Assays of growing cells showed an increasing bioluminescent response with increasing concentrations of toluene, up to 10 mg L$^{-1}$ toluene, after 90 minutes exposure (FIG. 18). The relationship was linear over this range. The bioluminescent response varied from 2.4 namp at 0.1 mg/l toluene to approximately 90 namp for 10, 20 and 50 mg/l toluene. There was not a significant bioluminescent response for 0 and 0.01 mg/l toluene. Similarly, the light response increased with increasing concentration of water-soluble jet fuel components (FIG. 18). At 10 μl jet fuel-saturated MSM added (approximately 0.02 mg/l toluene), the light response was 16 namp, while at 100 μl added (approximately 0.2 mg/l toluene). The response increased to 31 namp. The bioluminescence response for the 0.1 mg/l toluene equivalent of jet fuel was about 10 times that for 0.1 mg/l toluene, so other components beside toluene appear to have affected bioluminescence.

Figure 19:
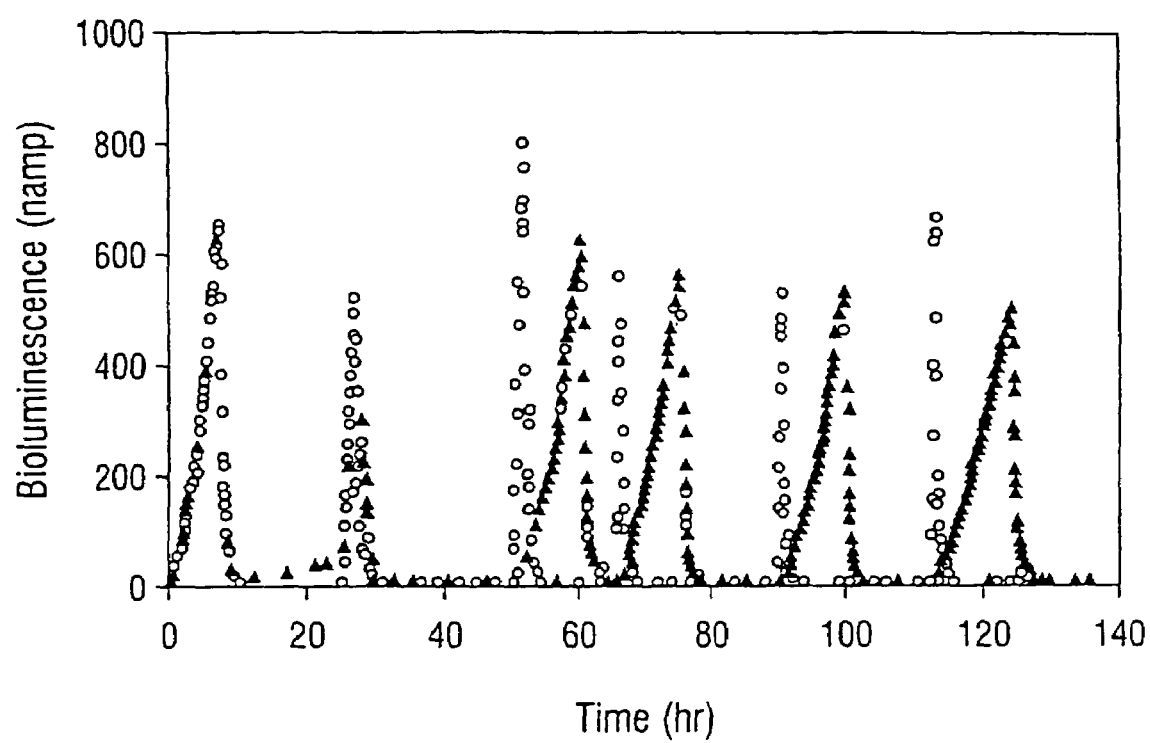
FIG. 19 shows bioluminescent response to multiple and single exposures of 10 mg $L^{-1}$ toluene by resting cells of *P. putida* B2 in batch studies. Symbols: μ multiple exposure; Δ single exposure.

In resting cell assays, the bioluminescent response to single exposures of toluene was rapid and reproducible (FIG. 19). The initial injection to the multiple exposure vial showed the same characteristic light response as each single exposure vial. However, there was a slower response (the rate of increase in bioluminescence, $H^{-1}$) upon initial exposure to toluene compared with the response of cells previously exposed to toluene. In addition, the response rate increased with each exposure to toluene (Table 7). However, the maximum bioluminescent response for both the single and multiple exposures was the same at 573±127 namp.

TABLE 7

BIOLUMINESCENT RESPONSE RATE (NAMP/HR) FOR MULTIPLE AND SINGLE EXPOSURES OF 10 MG/L TOLUENE[A]

| Time Point | Multiple Exposure Vial[b] | Single Exposure Vials[c] |
|---|---|---|
| 1 | 95 | ND |
| 2 | 321 | 137 |
| 3 | 642 | 67 |
| 4 | 768 | 60 |
| 5 | 737 | 60 |
| 6 | 973 | 49 |

[a]Response rate is defined as rate of bioluminescence increase with time.
[b]A single vial, with multiple additions of toluene.
[c]A new vial, previously unexposed to toluene, injected with toluene at each time point.
ND, not done.

Immobilized Cell Reactor System

Figure 20:
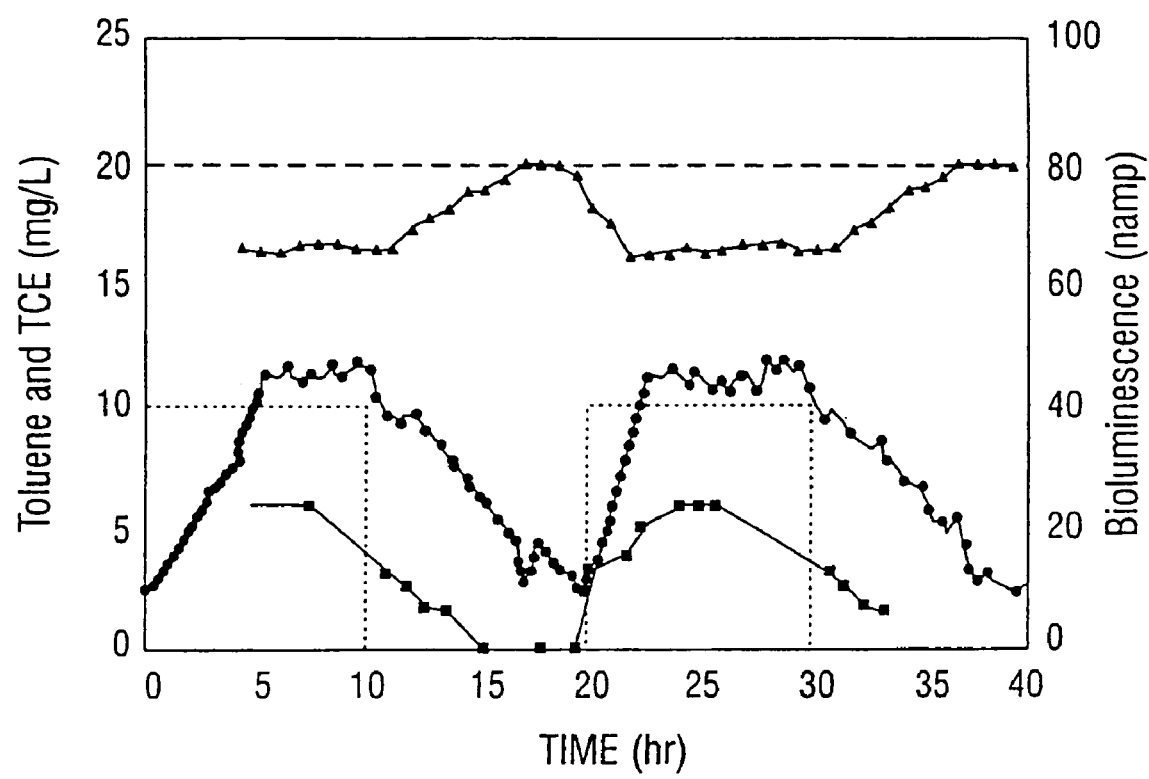
FIG. 20 shows bioluminescence and co-metabolism of TCE by *P. putida* B2 in response to square wave perturbations of 10 mg $L^{-1}$ toluene in 20-h cycles. Symbols: λ bioluminescence; σ, TCE in effluent; ν, toluene in effluent; ----, TCE in feed; ---, toluene in feed.

The DVR system loaded with alginate-encapsulated *P. putida* B2 was used to determine the light response and TCE co-metabolism of *P. putida* B2 when exposed to toluene in immobilized systems. Experimental results showed a rapid bioluminescent response under the introduction of toluene. FIG. 20 shows light response of the reporter strain in the reactor to the change in inlet toluene concentration and removal of TCE. The data show a direct response of bioluminescence with respect to toluene concentration. During the cycle, light emission increased by 16.3±1.2 namp/hr. The toluene effluent concentration approached zero after the toluene feed was stopped, and the light response in the reactor decreased at a rate of 3.4±0.8 namp/hr. A direct correlation between bioluminescence and TCE degradation was observed. The maximum light response was 43.4±6.8 namp. The steady-state TCE effluent concentration when toluene was being introduced into the system was 16.5±0.2 mg/l (20% removal), while the effluent toluene concentration was 5.8±0.1 mg/l (50% removal). This represents a ratio of 1.7 μmol toluene degraded/μmol TCE degraded. While results from the different assay types showed similar response to toluene, the magnitude of bioluminescence cannot be compared due to several differences between experimental conditions (i.e., sample agitation, cell physiology, light monitoring).

Discussion

Assays of growing cells demonstrated not only a qualitative bioluminescent response to toluene, but a quantitative response as well. There was a linear relationship between bioluminescence and toluene concentration between 0 and 10 mg/l in assays of growing cells. In addition, the bioluminescent response was proportional to dilutions of a complex environmentally relevant contaminant, jet fuel. However, the magnitude of the bioluminescent response to jet fuel was higher than would be expected if the response was due solely to the toluene in the jet fuel. Work with another bioluminescent strain has recently shown there is a significant bioluminescent response to solvents (Heitzer et al., 1996). It was demonstrated that cells were limited for the aldehyde substrate of the luciferase reaction. It was hypothesized that solvents perturb the cellular membrane, causing intracellular concentrations of fatty acids to increase. Since fatty acids are reduced to the corresponding aldehydes by the lux enzymes, increased amounts would negate the aldehyde limitation, causing higher bioluminescence. This solvent effect might explain the observed difference in magnitude of bioluminescence between pure toluene and toluene in a solvent matrix in assays of growing cells.

Typically, in the environment, cells would not be in midlog phase of growth. Therefore, the inventors examined the bioluminescent properties under resting cell conditions as well. Even in cells with toluene as an intermittent sole carbon source, the bioluminescent response was reproducible for at least 5 days. A more rapid bioluminescent response was observed for cells previously exposed to toluene, but the maximum bioluminescence remained constant.

Immobilized *P. putida* B2 allowed on-line monitoring of degradative activity towards toluene and TCE in a DVR. The system showed a direct correlation between toluene degradation and bioluminescence. Because the lux and tod operons are under the same promoter control, bioluminescence indicated that the tod operon was expressed, and TCE was co-metabolized. Therefore, there was a direct mechanistic correlation between bioluminescence and TCE co-metabolism. In this study, TCE did not appear to induce the tod operon in *P. putida* B2 as was reported for another *P. putida* strain (Heald and Jenkins, 1994). FIG. 20 shows that in the absence of toluene, TCE influent and effluent concentrations were equivalent and there was no bioluminescence increase.

Exposure to TCE and/or its metabolites may be toxic and may affect degradative enzyme activity. However, the intensity of bioluminescence was reproducible in successive perturbations of toluene even in the presence of TCE (FIG. 20). These data showed the tod-lux reporter provided an on-line measurement of tod gene expression, and also provided an indication of potential toxic effects due to continuous TCE exposure. At 20 mg/l TCE, there did not appear to be any toxic effects. This example demonstrated that there is a distinct and reproducible response to toluene under a variety of physiological conditions (growing and resting free cells and immobilized cells).

Example 3

Kinetics and Response of a *P. fluorescens* Biosensor

Polycyclic aromatic hydrocarbons (PAH) are persistent environmental contaminants that are toxic and carcinogenic. Hundreds of sites exist nationwide that are highly contaminated at concentrations greater than grams PAH per kilogram of soil. These sites range from 1 to over 100 acres. Indigenous soil organisms have demonstrated their ability to degrade these compounds.

King et al. (1990) reported the construction of pUTK21 by the transcriptional fusion of the luxCDAB cassette and the nahG gene within the archetypal NAH plasmid pKA1. The catabolic plasmid pKA1 from which pUTK21 was engineered is organized in two operons, the naphthalene and salicylate operons, and mediates the degradation of naphthalene, salicylate, and many other pollutants. The pUTK21 contains two pathways, an upper pathway, which codes for the degradation of naphthalene to salicylate (the naphthalene operon), and a lower engineered pathway, which codes for the lux pathway. The lower pathway no longer codes for salicylate degradation as the nahG gene was disrupted by insertion of the luxCDABE cassette. Both pathways of pUTK21 are controlled by promoters induced by salicylate. The reporter bacterium, *Pseudomonas fluorescens* HK44 (HK44), harbors the pUTK21. The HK44 supplements the disabled salicylate operon by naturally degrading salicylate by a pathway independent of nah. A positive-quantitative relationship between bioluminescence and inducer concentration (naphthalene and salicylate) as well as degradation of these compounds was demonstrated (DiGrazia, 1991). Bioluminescence activity requires oxygen, NADPH, ATP, $FMNH_2$, and aldehyde substrate. The luxCDABE genes code heterodimeric luciferase, reductase, transferase, and synthetase. The light reaction requires a long-chain aldehyde substrate, which is converted to a fatty acid during the light reaction. The fatty acid reductase complex (reductase, transferase, and synthetase) is essential as it regenerates the long-chain aldehyde substrate from the fatty-acid product.

Previous studies employing free HK44 indicate a linear light response with salicylate and naphthalene concentration (Heitzer et al., 1994). This example describes the form and parameters of salicylate by immobilized HK44. Potential differences exist in bacterial physiology between free and immobilized states. Because they are "noninvasive, nondestructive, rapid, and population specific", bioluminescent reporter strains have the potential to rapidly indicate bioavailability, degradative activity, and optimal degradation conditions in situ. The HK44 biosensor described herein may be produced by immobilizing HK44 on a light-culminating device (e.g., fiber optic). The HK44 sensor could then be employed to continuously monitor conditions and degradation in soils. Uses of such a sensor could include (1) detection of plumes (e.g., salicylate is a mobile daughter compound produced by the biological degradation of naphthalene and several other PAH) or (2) monitoring remediation during later stages of remediation as PAH concentrations are reduced. Provided are mathematical descriptions of salicylate degradation by immobilized HK44. An exemplary system is shown which has a packed-bed reactor (PBR) with alginate-immobilized HK44.

Mathematical Models

This example describes a plug-flow reactor with a bed of immobilized HK44. Assuming that significant flow occurs only in the axial direction, an unsteady-state shell mass balance on the bulk liquid phase from time t to t+$\Delta$t and from position z to z+$\Delta$z results in:

$$\int_t^{t+\Delta t}\left[\in S[C_i\overline{V}]_{z,t} - \in S[C_i\overline{V}]_{z+\Delta z,t} + \in \right. \quad (24)$$
$$S\left[-D_i\frac{\partial C_i}{\partial z}\right]_{z,t} - \in S\left[-D_i\frac{\partial C_i}{\partial z}\right]_{z+\Delta z,t}\right]dt -$$
$$\int_z^{z+\Delta z}N_{P_i}(1-\in)S\,dz = \int_z^{z+\Delta z}\left[S\in C_i|_{t+\Delta t,z} - S\in C_i|_{t,z}\right]dz$$

Equation (24) reduces to Equation (25) by applying the mean value theorem of integral calculus, dividing through by $\Delta z$ and $\Delta t$, taking limits as $\Delta t$ and $\Delta z$ go to 0, and substituting for the rate of mass transfer, the surface area of a spherical bead, and the superficial velocity:

$$-\overline{V}\frac{\partial C_i}{\partial z} + D_i\frac{\partial^2 C_i}{\partial z^2} = \frac{\partial C_i}{\partial t} + \frac{(1-\in)}{\in}K_i\frac{3}{r_0}(C_i - C_{p_i}|_{r=r_0}) \quad (25)$$

Equation (18) can be made dimensionless by the following substitutions:

$C_{i_0}C_{D_{P_i}}=C_{p_i}$, $C_{i_0}C_{D_i}=C_i$, $C_{i_0}\theta_{s_i}C_{D_{s_i}}=C_{s_i}$, $L\Phi=z$, $t_r\tau=t$, and $r_0\phi=r$ (26)

Equation (20) results upon substitution:

$$\frac{t_r D_{P_i}}{L^2}\frac{\partial^2 C_{D_i}}{\partial\Phi^2} - \frac{\partial C_{D_i}}{\partial\Phi} - \frac{\partial C_{D_i}}{\partial\tau} + \frac{(1-\in)}{\in}\frac{3t_r}{r_0}K_i(C_{D_i} - C_{P_i}|_{r=r_0}) = 0 \quad (27)$$

The initial condition assumes a clean bed. The boundary conditions in dimensionless form are $$\frac{\partial C_{D_i}}{\partial\Phi}\bigg|_{\Phi=1.0} = 0 \text{ and } C_{D_i}\bigg|_{\Phi=0} - C_{D_i} + \frac{D_i}{VL}\frac{\partial C_{D_i}}{\partial\Phi}\bigg|_{\Phi=0} = 0 \quad (28)$$

An unsteady-state mass balance on the solid phase yields:

$$\int_t^{t+\Delta t}[4\pi r^2(\in_p N_{P_i})|_{r,t} \quad (29)$$
$$-4\pi(r^2+\Delta r)(\in_p N_{P_i})|_{r+\Delta r,t} + 4\pi r^2\Delta r R_i]dt =$$
$$\int_r^{r+\Delta r}[(\in_p C_{P_i}+C_{s_i})|_{r,t} - (\in_p C_{P_i}+C_{s_i})|_{r,t+\Delta t}]dr$$

where liquid diffusion rate is assumed to be dominant and equilibrium is assumed in the pores. A term can be developed for the absorbed solid-phase flux by adding terms to the above development. Equation (30) results after applying the mean value theorem of integral calculus, dividing by $\Delta z$ and $\Delta t$, taking limits as $\Delta t$ and $\Delta z$ go to zero, making the substitutions in Equation (26), and assuming linear adsorption:

$$\frac{\in_p D_{P_i}t_r}{r_0^2}\frac{\partial^2 C_{D_{P_i}}}{\partial\varphi^2} + \frac{2\in_p D_{P_i}t_r}{r_0^2\varphi}\frac{\partial C_{D_{P_i}}}{\partial\varphi} + \frac{t_r}{C_{i_0}}R_i = \quad (30)$$
$$\frac{\partial D_{D_{P_i}}}{\partial\tau}\left(\in_p + \theta_{s_i}\frac{dC_{D_{s_i}}}{dC_{D_{P_i}}}\right)$$

The exact form of Ri is unknown for this system. The Michaelis-Menten reaction model (MMRM) is general and reflects a nonlinear relationship between degradation rate and substrate concentration rate and substrate concentration. This nonlinear relationship arises from the finite degradative capacity of biological systems. At low concentrations, the MMRM approaches a reaction rate which is first order in substrate concentration. As the degradative capacity of the system is approached or exceeded, the MMRM becomes zero order in concentration. Thus a large number of conditions distributed over the reaction regime are required to properly measure the two MMRM rate constants. The reaction rate form and constants were elucidated by first comparing the steady-state behavior of the HK44 to the limiting cases of the MMRM. These limiting cases were represented mathematically as first order in salicylate and first order in biomass as:

$$-R_{salicylate} = K_2 C_{Biomass} C_{Salicylate} \qquad (31)$$

and as zero order in concentration and first order in biomass as:

$$-R_{salicylate} = K_1 C_{Biomass} \qquad (32)$$

Equations (31) and (32) each require a single rate constant instead of two as required by the Michaelis-Menten model. Practically, the linear rate models, Equations (31) and (32), provide a more stringent description of behavior than the two-parameter, nonlinear MMRM.

Initial and boundary conditions assume a clean bed, symmetry within the bead, and no accumulation at the solid interface:

$$C_{D_{P_i}}(0, \varphi) = 0, \quad \frac{\partial C_{D_{P_i}}}{\partial \varphi} = 0, \qquad (33)$$

$$\text{and} \frac{\epsilon_p D_{P_i}}{r_0 K_i} \frac{\partial C_{D_{P_i}}}{\partial \varphi}\bigg|_{\supset=1} = (C_{D_i} - C_{D_{P_i}}|_{\varphi=1})$$

Equations (27) and (30) indicate that the processes which affect the distribution and conversion of the substrate include: (1) dispersion and convective transport in the bulk phase; (2) bulk and internal solid-phase mass transfer resistance; (3) adsorption onto the alginate inside the bead pores; and (4) chemical conversion by bacteria only within the bead. A constant distribution of biomass is assumed with no growth. If growth occurs, then biomass distribution may become a function of bead radius (Kuhn et al., 1991). The model was simplified for analyzing bed steady-state behavior by assuming negligible mass transfer resistance. This simplified model, when combined with the reaction rate Equation (31), has the solution (Danckwerts, 1953):

$$\frac{C_{Salicylate}}{C_{Salicylate|\Phi=0}} = \frac{4\eta \exp(Pe/2)}{(1+\eta)^2 \exp(Pe\eta/2) - (1-\eta)^2 \exp(-Pe\eta/2)} \qquad (34a)$$

where:

$$\eta = \left(1 + \frac{4 K_x C_{Biomass}}{\bar{V} Pe}\right)^{1/2} \qquad (34b)$$

This simplified model, when combined with the reaction rate Equation (33) has the solution:

$$C_{Salicylate} = \frac{\vartheta \exp[Pe(\Phi-1)]}{Pe} - \vartheta\Phi - \frac{\vartheta}{Pe} + 1 \qquad (35a)$$

where:

$$\vartheta = \frac{L k_1}{\bar{V}} \frac{C_{Biomass}}{C_{Salicylate}|_{\Phi=0}} \qquad (35b)$$

The unsteady-state behavior and the full model predictions could then be compared for evaluation of critical assumptions. Mathematical problems for which analytical solutions were unavailable were solved using the PDECOL software package (Madsen and Sincovec, 1979). Available analytical solutions and numerical results were compared for diffusion, transport, and reaction processes (Crank, 1975). Other investigators have also used PDECOL for simulation of PBR processes (Costa and Rodrigues, 1985).

Materials and Methods

A previously developed PBR system with on-line instrumentation (Webb, 1992; Webb et al., 1991) was used to measure bacterial degradative and bioluminescent activity under conditions mimicking those of the subsurface. The reactor design is detailed in FIG. 21. The PBR was temperature controlled and fitted with metal frits welded to the inlet and outlet to retain and distribute feed to immobilized cultures. An additional inter-cavity insert allowed the installation of filters (e.g., 0.2-mm inorganic and polymeric) between the packed bed and outlet frit that filtered the effluent for automatic injection into the on-line high-performance liquid chromatography (HPLC) and that produced a uniform resistance to flow that improved the overall distribution to the reactor (Webb, 1992). The reactor had an internal diameter of 1.34 cm, whereas the bed length could be varied from 0.8 to 11.0 cm. HPLC pumps supplied media to each reactor from pressurized feed reservoirs. All nutrients, including oxygen, entered the reactor dissolved in the liquid phase. Naphthalene and salicylate were detected with an on-line HPLC using a Vydac TP20154 column (Sep/A/Ra/Tions Group, Hesperia, Calif.) with a FL-4 dual-monochromator fluorescent detector (Perkin-Elmer, Norwalk, Conn.). Respective excitation and emission wavelengths for salicylate detection were 290 and 360 nm. The reactor was fitted with an on-line light detector for monitoring bioluminescent activity (Dunbar, 1992) consisting of a glued fiber bundle (Ensign Bickford Optics, Simsbury, Conn.) placed approximately 2.5 cm from the entrance of the reactor. An Oriel Inc. (Stratford, Conn.) 7070 photomultiplier detection system using a Model 77348 photomultiplier tube (radiant sensitivity of 80 MA/W near 500 nm) were employed.

A second apparatus simulated flow passed through an alginate biosensor. The apparatus was composed of a flow cell and a Hamamatsu photodiode (Bridgewater, N.J.) with an attached layer of HK44 immobilized in alginate. The flow cell volume was 5 ml, whereas the flow rate was maintained at 1.5 ml/min. The concentration of salicylate was varied while the light was monitored with the photodiode. Mineral salts media was used for these experiments with varying concentration of inducer.

Mineral salts media (pH 7.2) consisting of $MgSO_4 \cdot 7H_2O$ (0.1 g/l), $NH_4NO_3$ (0.2 g/l), trizma™ base (3.03 g/l), MgO ($1.0 \times 10^{-3}$ g/l), $CaCl_2$ ($2.9 \times 10^{-4}$ g/l), $FeCl_3 \cdot 6H_2O$ ($5.4 \times 10^{-4}$ g/l), $ZnSO_4 \cdot 7H_2O$ ($1.4 \times 10^{-4}$ g/l), $CuSO_4$ ($2.5 \times 10^{-5}$ g/l), $H_3BO_4$ ($6.2 \times 10^{-6}$ g/l), and $Na_2MoO_4 \cdot H_2O$ ($4.9 \times 10^{-5}$ g/l) were supplied to the reactor with an appropriate carbon source for degradation and bioluminescence studies. Kinetic bacterial studies were phosphate limited and maintained aerobic by con-trolled pressurization of feeds and the reactor.

The HK44 was prepared for immobilization by adding freshly thawed inoculum (frozen at −70° C. until use) to 100 mL of YEPG media which contained glucose (1.0 g/l), polypeptone (2.0 g/l), yeast extract (0.2 g/l), $NH_4NO_3$ (0.2 g/l), and tetracycline (14 mg/l). The culture was shaken for 15 hours at 25° C. and then centrifuged at 8000 rpm for 10 minutes. The pellet was then washed with 0.9% NaCl solution three times before immobilization. The concentration of HK44 was enumerated by measuring optical density at 546 nm. The HK44 was immobilized by suspending bacteria in 0.9% NaCl solution and mixing with a low-viscosity alginate (28 g/L) and NaCl (9 g/L) solution in a ratio of 1:2 by volume. Beads were formed by controlled dropwise addition to 0.1 M $CaCl_2$ solution by a syringe needle installed in an air jet controlled by a precision regulator (Porter Instrument Co., Hatfield, Pa.) and a piece of 0.003-in. (i.d.) tubing. Beads diameters were measured using gentle wet sieving. Alginate beads were dissolved in 50 mM sodium hexametaphosphate.

Naphthalene and sodium salicylate adsorption isotherms on calcium alginate were measured using batch equilibrium and breakthrough curve methods (Ruthyen, 1984). Residence time distributions for dispersion and liquid-phase mass transfer measurements were evaluated using salicylate (0.1 M), potassium, and/or bromide (1.0 M) introduced through a six-port HPLC valve up-stream of the reactor. Tracer concentrations were measured using a Waters ion-chromatography system with a series 510 HPLC pump, IC-PAK anion exchange column, and 431 conductance detector (Waters, Cam-bridge, Mass.) or monitored continuously using fluorescence.

Abiotic Properties

Figure 22:
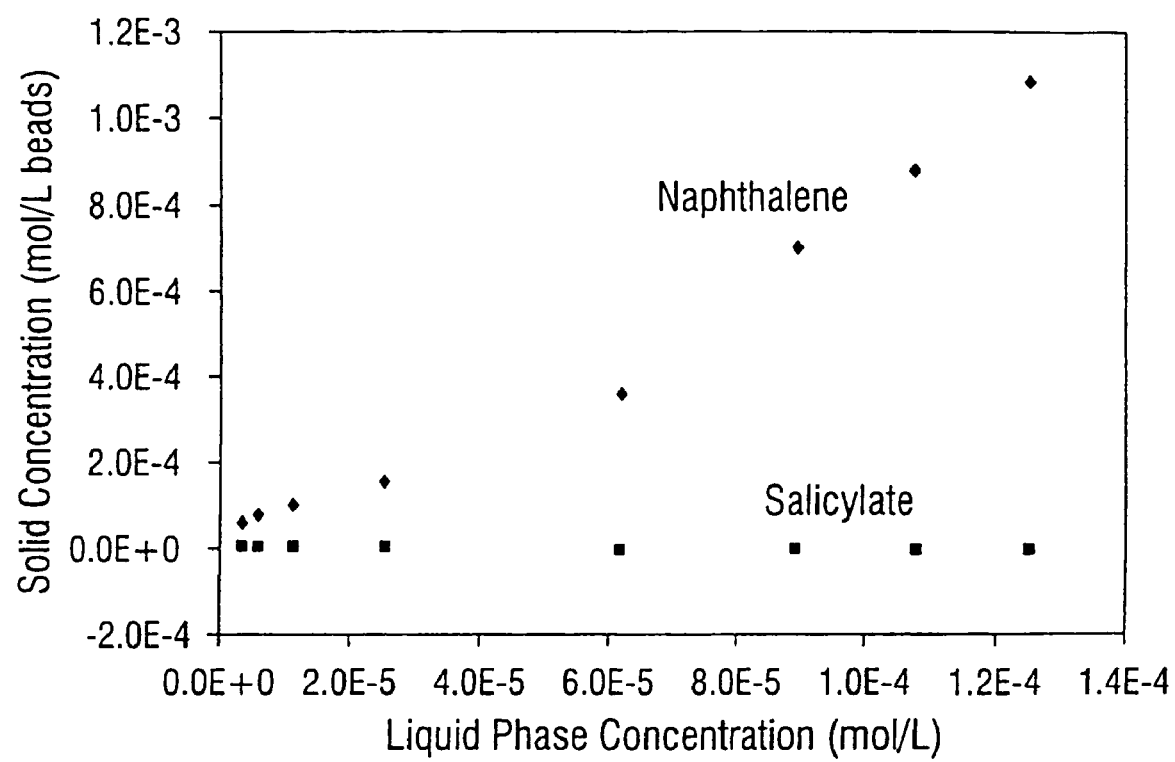
FIG. 22 shows absorption isotherms of naphthalene and sodium salicylate on calcium alginate. Naphthalene adsorbed linearly at experimental conditions, whereas salicylate did not appreciably partition.

Typically, almost all of the bead diameters ranged between $3.9 \times 10^{-2}$ and $7.5 \times 10^{-2}$ cm. For example, 4, 65, and 31 wt % were retained on $7.5 \times 10^{-2}$, $4.5 \times 10^{-2}$, and $3.9 \times 10^{-2}$ cm screens, respectively. Salicylate did not measurably absorb onto the alginate, whereas the naphthalene isotherm was linear with a dimensionless ratio of 8.4 (FIG. 22). Final equilibrium liquid-phase concentration ranged from 0.0 to $1.5 \times 10^{-4}$ M, whereas solid concentrations ranged to $1.1 \times 10^{-3}$ moles of naphthalene per liter of alginate. Dispersion was measured by linearizing the analytical relationships derived by Haynes and Sarma (1973). Slopes ranged between $1 \times 10^{-2}$ and $2 \times 10^{-2}$ m$^2$/min, indicating that dispersion was on the order of $10^{-2}$ cm$^2$/min. Comparison of reactor volumes and average residence times demonstrated that channeling was not significant. Hydrophobic filters effected a uniform resistance to flow over the reactor outlet and greatly improved flow characteristics. Blot numbers ranged around 100 and indicate that mass transfer was not significant.

Alginate appears to be a good immobilization media for naphthalene and salicylate reporter bacteria due to its favorable transport and adsorption properties. Also, alginate may be formed into shapes useful for sensor applications (e.g., as a thin sheet attached directly to a light probe). Salicylate and naphthalene are good test compounds because naphthalene is an abundant environmental pollutant and generally found with other PAH contaminants, whereas salicylate is a metabolite of naphthalene and several other PAH. Care should be taken in choosing an immobilization matrix for detecting other PAH, because larger PAH may significantly deviate from these model compounds in their solubility and absorption characteristics.

Kinetic Evaluation of *P. fluorescens* HK44

Different combinations of feed concentrations, biomass, and flow rates, listed in columns 2 to 4 of Table 8, were varied in 18 studies to determine the form of the degradation rate equation and associated constants. Five charges of immobilized cells used for these studies are indicated by a number designation in column 1. Liquid-phase mass transfer was estimated using the correlation of Kataoka et al. (1973).

Steady-state behavior was achieved within several bed volumes after a perturbation, consistent with predictions by Equations (20) and (23) using measured parameters. Bacterial degradative activity was then constant, although a small amount of drift was noticed in some studies (indicated by higher standard deviations). Ranges for biomass, salicylate concentration, and residence time were $1.9 \times 10^9$ to $3.5 \times 10^9$ cells/ml, 2.25 to 4.5 mg/l, and 14 to 150 min, respectively. Salicylate was supplied to the reactor at or below 4.5 mg/l. Stoichiometric levels of dissolved oxygen might prove toxic to HK44 at high salicylate concentration. Concentrations above this range would probably not be realistic as very few PAH are soluble at greater than 1-mg/l concentrations (Lee et al., 1979). Salicylate conversion, listed in column 5, ranged from 9% to 92%, with standard deviations ranging from 1.08% to 2.96% normalized to the effluent concentrations. Standard deviations and average conversions in column 5 were calculated using an average of 100 data points for each case.

Five independent studies were repeated and demonstrated reproducible relationships between substrate conversion, biomass, feed concentration, and re-actor residence time: (1) studies 4b and 3d had conversions of 0.62; (2) studies 4f and 4c had con-versions of 0.50; (3) studies 3e and 4d had respective conversions of 0.41 and 0.39; (4) studies 1a and 1c had respective conversions of 0.64 and 0.73; and (5) studies 3c and 3f had respective conversions of 0.77 and 0.70.

Figure 23:
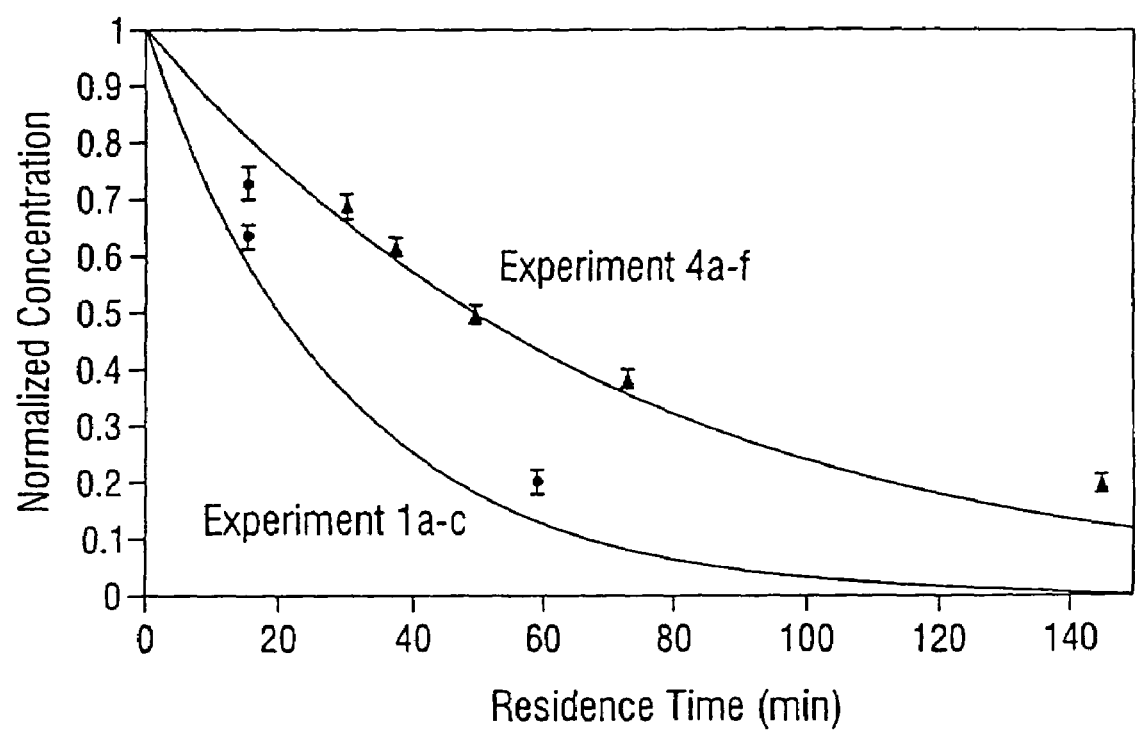
FIG. 23 shows actual and predicted concentrations of studies 1*a-c* and 4*a-f*. Error bars are shown with average values. The solid line represents the model predictions using the least-squares reaction rate constant for the complete data set. The model is overall second order, first order in biomass and first order in salicylate, with a rate constant of $2.23 \times 10^{-2}$ $dm^3/g$ mol. The empirical data depicted are from Table 8.
Figure 24:
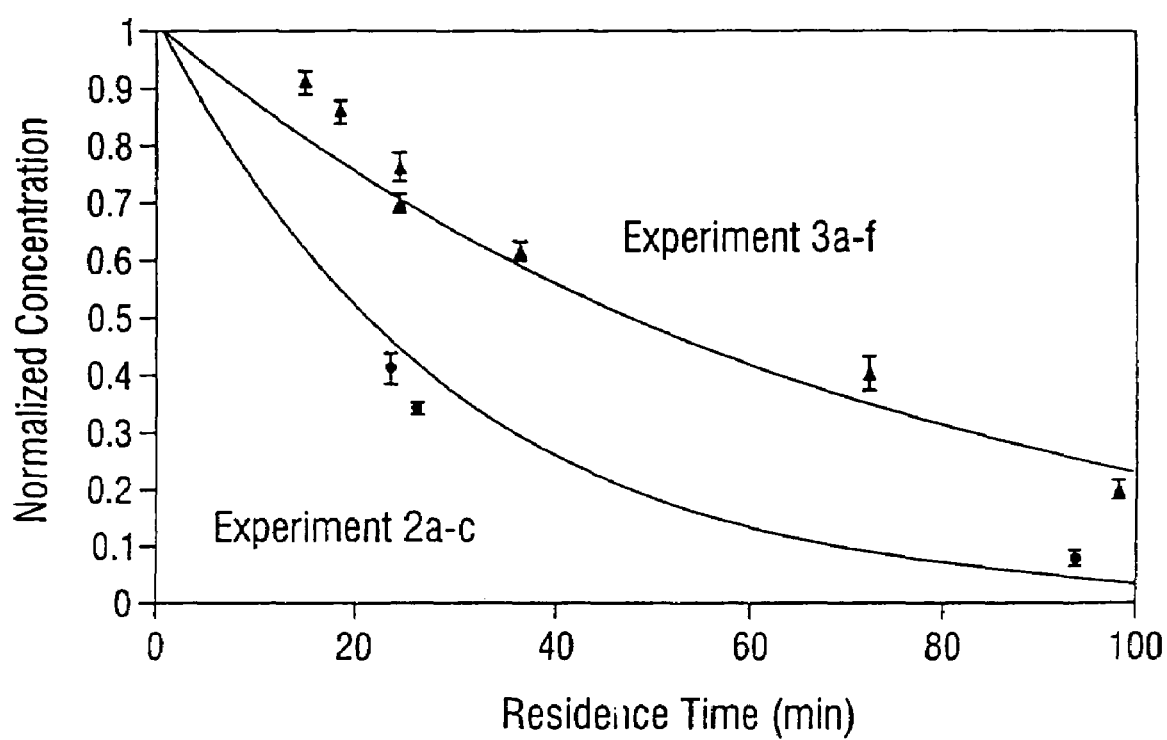
FIG. 24 shows actual and predicted concentrations of studies 2*a-c* and 3*a-f*. Error bars are shown with data points. The solid line represents the model predictions using the least-squares reaction rate constant for the complete data set. The model is overall second order, first order in biomass and first order in salicylate, with a rate constant of $2.23 \times 10^{-2}$ $dm^3/g$ mol. The empirical data depicted are from Table 8.

Equation (27), using the degradative rate constant as the sole adjustable parameter, provided a good description of the experimental data. As depicted in FIG. 23 and FIG. 24, the reaction rate decreased with decreasing substrate concentration. The regressed degradation rate constants from experimental sets 1a-c, 3a-f, and 4a-f were tightly grouped. The rate constants obtained using the full data set and subsets were: (1) $2.23 \times 10^{-2}$ dm$^3$ g$^{-1}$ min$^{-1}$ fitted to the complete set; (2) $1.88 \times 10^{-2}$ fitted to subset 1a-c; (3) $2.85 \times 10^{-2}$ fitted to subset 2a-c; (4) $2.06 \times 10^{-2}$ fitted to subset 3a-f; and (5) $2.28 \times 10^{-2}$ fitted to subset 4a-f. FIG. 23 and FIG. 24 demonstrate good agreement between the full data set and Equation (27) using $2.23 \times 10^{-2}$. Study 2a-c contributed the most to the total residual for all 18 studies. DiGrazia (1991) found that naphthalene degradation by HK44 could be described by a rate term which was first order in naphthalene and first order in biomass.

Equation (28) was less appropriate for describing the kinetics of HK44 than Eq. (X). Residuals were generally an order of magnitude larger than those using Equation (27). Also, the fundamental relationships suggested by Eq. (X) were not born out by the data. The rate constants obtained using Eq. (28) ranged over almost half an order of magnitude, $4.33 \times 10^{-5}$ to $1.35 \times 10^{-4}$ min$^{-1}$.

TABLE 8

STEADY-STATE DEGRADATION AND LIGHT PRODUCTION BY *P. FLUORESCENS* HK44 AS A FUNCTION OF BIOMASS, FEED CONCENTRATION, AND RESIDENCE TIME

| Experiment | Biomass (cells/mL) | Sodium salicylate (mg/L) | τ (min) | Salicylate effluent ± σ (mg/L) | Bioluminescence ± σ-(nA) |
|---|---|---|---|---|---|
| 1a | $3.3 \times 10^9$ | 2.25 | 14 | $1.43 \pm 2.85 \times 10^{-2}$ | Unavailable |
| 1b | $3.3 \times 10^9$ | 2.25 | 58 | $0.46 \pm 0.84 \times 10^{-2}$ | Unavailable |
| 1c | $3.3 \times 10^9$ | 2.25 | 14 | $1.65 \pm 4.77 \times 10^{-2}$ | Unavailable |
| 2a | $3.5 \times 10^9$ | 2.47 | 24 | $1.03 \pm 2.83 \times 10^{-2}$ | $2.71 \pm 4.0 \times 10^{-2}$ |
| 2b | $3.5 \times 10^9$ | 2.47 | 26 | $0.86 \pm 0.93 \times 10^{-2}$ | $1.81 \pm 2.0 \times 10^{-2}$ |
| 2c | $3.5 \times 10^9$ | 2.47 | 94 | $0.20 + 0.28 \times 10^{-2}$ | $0.16 + 2.0 \times 10^{-2}$ |
| 3a | $1.9 \times 10^9$ | 4.45 | 15 | $4.06 \pm 8.85 \times 10^{-2}$ | Unavailable |
| 3b | $1.9 \times 10^9$ | 4.45 | 18 | $3.84 \pm 6.99 \times 10^{-2}$ | Unavailable |

TABLE 8-continued

STEADY-STATE DEGRADATION AND LIGHT PRODUCTION
BY *P. FLUORESCENS* HK44 AS A FUNCTION OF BIOMASS,
FEED CONCENTRATION, AND RESIDENCE TIME

| Experiment | Biomass (cells/mL) | Sodium salicylate (mg/L) | $\tau$ (min) | Salicylate effluent $\pm \sigma$ (mg/L) | Bioluminescence $\pm \sigma$-(nA) |
|---|---|---|---|---|---|
| 3c | $1.9 \times 10^9$ | 4.45 | 24 | $3.42 \pm 8.55 \times 0^{-2}$ | $3.07 \pm 1.0 \times 10^{-1}$ |
| 3d | $1.9 \times 10^9$ | 4.45 | 36 | $2.77 + 4.24 \times 10^{-2}$ | $2.26 + 1.0 \times 10^{-2}$ |
| 3e | $1.9 \times 10^9$ | 4.45 | 72 | $1.81 \pm 5.36 \times 10^{-2}$ | $0.95 + 5.0 \times 10^{-2}$ |
| 3f | $1.9 \times 10^9$ | 4.45 | 24 | $3.12 \pm 4.09 \times 10^{-2}$ | Unavailable |
| 4a | $1.9 \times 10^9$ | 4.45 | 29 | $3.07 \pm 6.45 \times 10^{-2}$ | Unavailable |
| 4b | $1.9 \times 10^9$ | 4.45 | 36 | $2.76 \pm 3.95 \times 10^{-2}$ | Unavailable |
| 4c | $1.9 \times 10^9$ | 4.45 | 48 | $2.25 \pm 3.47 \times 10^{-2}$ | $2.17 + 8.0 \times 10^{-2}$ |
| 4d | $1.9 \times 10^9$ | 4.45 | 72 | $1.75 \pm 2.03 \times 10^{-2}$ | $1.61 \pm 6.0 \times 10^{-2}$ |
| 4e | $1.9 \times 10^9$ | 4.45 | 150 | $0.89 \pm 1.54 \times 10^{-2}$ | $0.83 \pm 6.0 \times 10^{-2}$ |
| 4f | $1.9 \times 10^9$ | 4.45 | 48 | $2.24 + 3.49 \times 10^{-2}$ | $2.53 \pm 4.7 \times 10^{-1}$ |
| 5a | $1.9 \times 10^9$ | 2.5 | 15 | Unavailable | $1.60 \pm 1.90 \times 10^{-1}$ |
| 5b | $1.9 \times 10^9$ | 2.5 (naphthalene 8.0) | 15 | Unavailable | $4.79 \pm 3.18 \times 10^{-1}$ |

Model predictions and data both demonstrate that salicylate conversion was limited by reaction rate and not mass transfer effects. Flow rates, effectiveness factors, Thiele modulus, Reynolds numbers, and Biot numbers are listed in Table 9. Biot numbers were on the order of 100. Effectiveness factor calculations using the best-fit first-order reaction rate constant indicate that the beads were limited by the reaction rate and not by internal mass transfer resistance. The good fit obtained using the analytical solution, wherein external and internal mass transfer was assumed negligible, also support the conclusion that mass transfer effects were minimal. The model predicts that the salicylate distribution reaches a steady state within an alginate bead (99% of final) in about 7 minutes. Even assuming that the diffusion coefficient was reduced by an order of magnitude in the alginate matrix, a steady state was reached within 15 min. Oyass et al. (1995) found that diffusion coefficients in calcium alginate were approximately 85% that in water for nine solutes (mono- and disaccharides and organic acids). Cell volume estimated at less than 1% probably had little effect on diffusion. The model also predicted that liquid mass transfer resistance would have little effect on reaching steady state. In the case of an adsorbing substrate such as naphthalene, the model demonstrates that adsorption must be taken into account. A positive 50% error in the measured adsorption coefficient would result in doubling the time required to reach steady state. The model predicted that steady state for naphthalene was achieved in approximately 1 hour starting from a clean alginate bed. Model parameters have been measured (liquid mass transfer coefficient, pellet void volume, and adsorption coefficients), reported, and estimated. Respective coefficients for naphthalene were $9.0 \times 10^{-6}$ cm$^2$ s$^{-1}$, $9.0 \times 10^{-8}$ cm$^2$ s$^{-1}$ and 8.4 cm$^2$ s mol$^{-1}$ for liquid diffusion, solid diffusion, and Langmuir equilibrium constants. Companion free cell studies are needed to further aid evaluation of free and immobilized kinetics and response.

TABLE 9

FLOW RATES, REYNOLDS NUMBERS, THIELE MODULI,
EFFECTIVENESS FACTORS, AND BIOT NUMBERS[1]

| Study | Flow Rate (cm/s) | Reynolds Number | Biot Number | Thiele Modulus | Effectiveness Factor |
|---|---|---|---|---|---|
| 1A | $1.17 \times 10^{-2}$ | $2.65 \times 10^{-1}$ | $1.53 \times 10^2$ | $9.25 \times 10^{-1}$ | $9.47 \times 10^{-1}$ |
| 1B | $2.92 \times 10^{-3}$ | $6.62 \times 10^{-2}$ | $9.66 \times 10^1$ | $9.25 \times 10^{-1}$ | $9.47 \times 10^{-1}$ |
| 1C | $1.17 \times 10^{-2}$ | $2.65 \times 10^{-1}$ | $1.53 \times 10^2$ | $9.25 \times 10^{-1}$ | $9.47 \times 10^{-1}$ |
| 2A | $1.17 \times 10^{-2}$ | $2.65 \times 10^{-1}$ | $1.53 \times 10^2$ | $9.07 \times 10^{-1}$ | $9.49 \times 10^{-1}$ |
| 2B | $1.05 \times 10^{-2}$ | $2.38 \times 10^{-1}$ | $1.48 \times 10^2$ | $9.07 \times 10^{-1}$ | $9.49 \times 10^{-1}$ |
| 2C | $2.92 \times 10^{-3}$ | $6.62 \times 10^{-2}$ | $9.66 \times 10^1$ | $9.07 \times 10^{-1}$ | $9.49 \times 10^{-1}$ |
| 3A | $1.17 \times 10^{-2}$ | $2.65 \times 10^{-1}$ | $1.53 \times 10^2$ | $6.77 \times 10^{-1}$ | $9.71 \times 10^{-1}$ |
| 3B | $9.36 \times 10^{-3}$ | $2.12 \times 10^{-1}$ | $1.42 \times 10^2$ | $6.77 \times 10^{-1}$ | $9.71 \times 10^{-1}$ |
| 3C | $7.02 \times 10^{-3}$ | $1.59 \times 10^{-1}$ | $1.29 \times 10^2$ | $6.77 \times 10^{-1}$ | $9.71 \times 10^{-1}$ |
| 3D | $7.02 \times 10^{-3}$ | $1.59 \times 10^{-1}$ | $1.29 \times 10^2$ | $6.77 \times 10^{-1}$ | $9.71 \times 10^{-1}$ |
| 3E | $4.68 \times 10^{-3}$ | $1.06 \times 10^{-1}$ | $1.13 \times 10^2$ | $6.77 \times 10^{-1}$ | $8.71 \times 10^{-1}$ |
| 3F | $2.34 \times 10^{-3}$ | $5.30 \times 10^{-2}$ | $8.97 \times 10^1$ | $6.77 \times 10^{-1}$ | $9.71 \times 10^{-1}$ |
| 4A | $1.17 \times 10^{-2}$ | $2.65 \times 10^{-1}$ | $1.53 \times 10^2$ | $6.77 \times 10^{-1}$ | $8.71 \times 10^{-1}$ |
| 4B | $9.36 \times 10^{-3}$ | $2.12 \times 10^{-1}$ | $1.42 \times 10^2$ | $6.77 \times 10^{-1}$ | $9.71 \times 10^{-1}$ |
| 4C | $7.02 \times 10^{-3}$ | $1.59 \times 10^{-1}$ | $1.29 \times 10^2$ | $6.77 \times 10^{-1}$ | $9.71 \times 10^{-1}$ |
| 4D | $7.02 \times 10^{-3}$ | $1.59 \times 10^{-1}$ | $1.29 \times 10^2$ | $6.77 \times 10^{-1}$ | $9.71 \times 10^{-1}$ |
| 4E | $4.68 \times 10^{-3}$ | $1.06 \times 10^{-1}$ | $1.13 \times 10^2$ | $6.77 \times 10^{-1}$ | $9.71 \times 10^{-1}$ |
| 4F | $2.34 \times 10^{-3}$ | $5.30 \times 10^{-2}$ | $8.97 \times 10^1$ | $6.77 \times 10^{-1}$ | $9.71 \times 10^{-1}$ |

[1]Flow rates approached creeping flow. Blot numbers ranged around 100, indicating that fluid-phase mass transfer was not significant. Effectiveness factors approached 1.0, indicating that the reaction rate mostly limited the overall reaction rate Bioluminescence Control studies were conducted to determine the effect of glucose, and mineral salts media (no carbon) on the light emission of HK44. Measured effluent oxygen levels were always in large excess (>10 ppm). Significant growth of HK44 was improbable as phosphate was not supplied to the reactor. Glucose is not an inducer for the lux pathway. Bioluminescent activity was constant and minimal using only mineral salts media. In further studies, glucose in mineral salts media was supplied to HK44 at 5 mg/L at a flow rate of 1.0 mL/min. When exposed to glucose, light emission was orders of magnitude less than the salicylate response but rose slowly for 26 hours above baseline noise. Emission was then steady for 12 hours until glucose was removed from the feed. Glucose is an excellent carbon and energy source and could possibly increase pools of one or more of the light substrates. Schell (1990) found that low levels of nah mRNA were present in uninduced cells. The trizma™ base buffer in the mineral salts feed maintained the pH at 7.2, even for studies with long residence times. Thus, pH does not appear to be a factor in the light response. These data suggest that the slight increase in light emission resulted from increased pools of reaction substrates and the presence of low, constitutive levels of lux enzymes.

Figure 25:
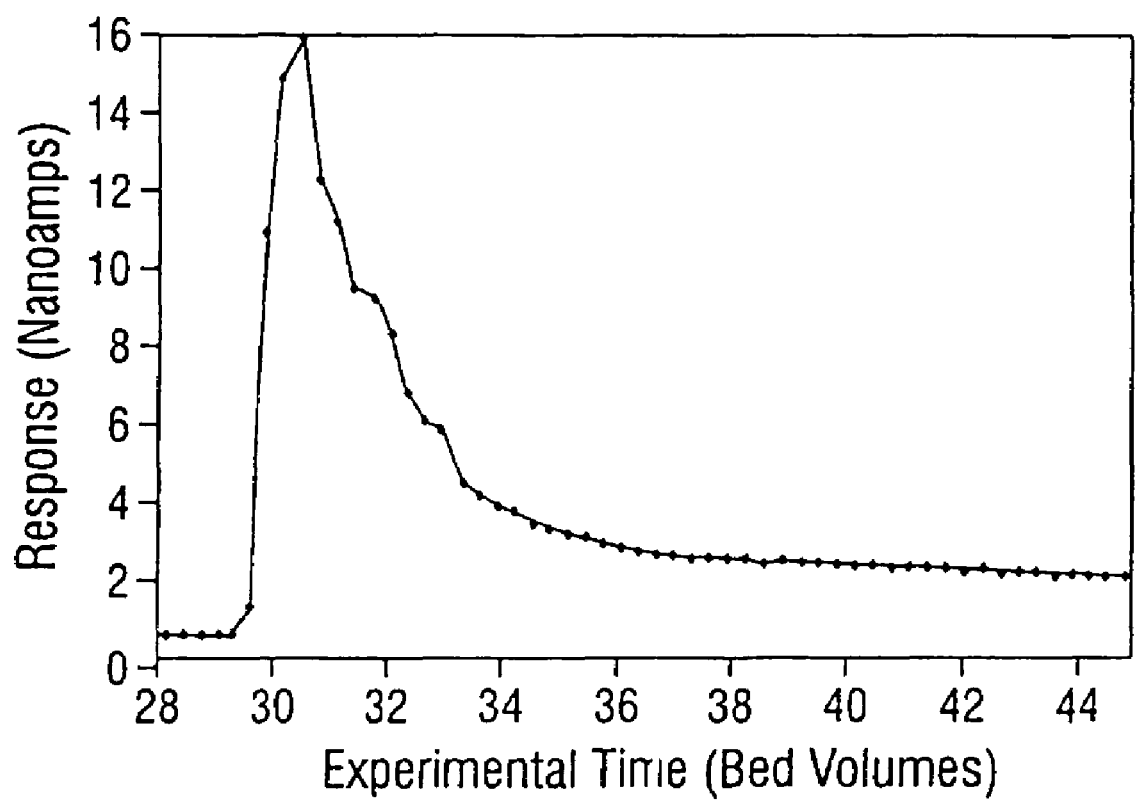
FIG. 25 show an unusual transient response was observed when a clean bed of HK44 was "shocked" by the step addition of salicylate. The transient response may be caused by an initial imbalance resulting from the rapid transport of the inducer into the cell and an initial slow rate of degradation. After this initial transient behavior, light intensity mimicked the concentration of inducer. This transient behavior was only observed at the beginning of the study. Light intensity tracked subsequent changes in inducer concentration.

During degradation studies, glucose solution was added to the reactor at a constant concentration throughout the study. Inducer was added 15 hours after starting the study. In almost all cases, light intensity mimicked the change in salicylate concentrations. As inducer increased, light intensity increased. Conversely, when inducer concentrations were decreased, light intensity decreased. The one exception to this behavior was observed only at the beginning of a study when a clean bed of HK44 was initially shocked by a step change in inducer concentration. Under this shock condition, light production initially increased orders of magnitude and reached a maximum approximately one residence time later (FIG. 25). Within four to six residence times, light intensity approached a steady state. In contrast, effluent concentrations became constant within two residence times. Thus, the unsteady-state light emission might result from an initial buildup of salicylate within the cell due to the rapid change in the salicylate bulk phase concentration and an imbalance between transport through the cell membrane and degradation. Also, addition of the glucose for 15 hours prior to addition of the inducer may have increased the light substrate pools, resulting in an oversupply of lux cofactors. Thus, further research would be appropriate for investigating this transient phenomena. For example, cofactor concentrations might be directly measured as a function of supplied substrates.

Figure 26:
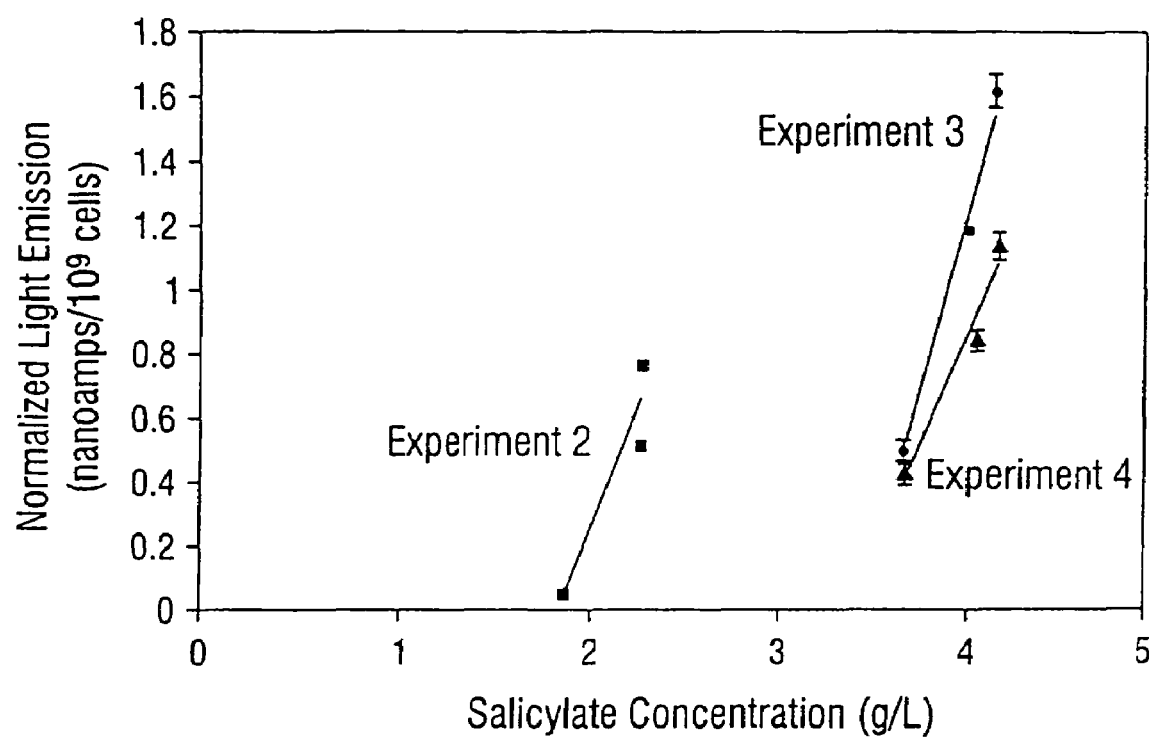
FIG. 26 shows specific steady-state light emission by alginate-immobilized *P. fluorescens* HK44 as a function of estimated concentration inside the PBR at the light probe. Standard deviations are shown with the average values. The lines represent the average linear response for each data set.

FIG. 26 depicts the average specific light response (light per unit biomass) as a function of predicted salicylate concentration at the light probe. The data in FIG. 26, obtained during degradation studies, are depicted as averages and standard deviations. During all studies, oxygen was maintained at a level that exceeded the stoichiometric demand. Oxygen effluent concentrations were always greater than several milligrams per liter. The light intensity depicted in FIG. 26 is reported as a function of the local inducer concentration at the light probe rather than the effluent concentration. The local salicylate concentrations were calculated using the model and parameters previously discussed. The purpose of FIG. 26 is to qualitatively compare the relationship between emission and inducer concentration. There was a positive relationship between light emission and inducer concentration. Best-fit lines had slopes of 1.4, 2.3, and 1.5 for studies 2a-c, 3c-e, and 4c-f, respectively. The present analysis must be treated qualitatively because light values were relative within a study as there was no reference light source for calibration between studies (e.g., variable alginate opacity). Thus, the true intercepts for the curves are unknown; however, the slopes were similar and indicate that light emission was a positive function of inducer concentration.

Studies were conducted to investigate the response to naphthalene (a parent compound of salicylate). Salicylate was added to the PBR as a control at 16 hours (study 5a). The response to salicylate was the same as in previous studies. Light emission was allowed to become steady prior to naphthalene addition.

The light response of alginate-immobilized HK44 was intense upon the addition of naphthalene at 45 hours. The steady-state response of HK44 to naphthalene was approximately two orders of magnitudes greater than the response to salicylate under identical conditions. These results were verified when studies were repeated.

Figure 27:
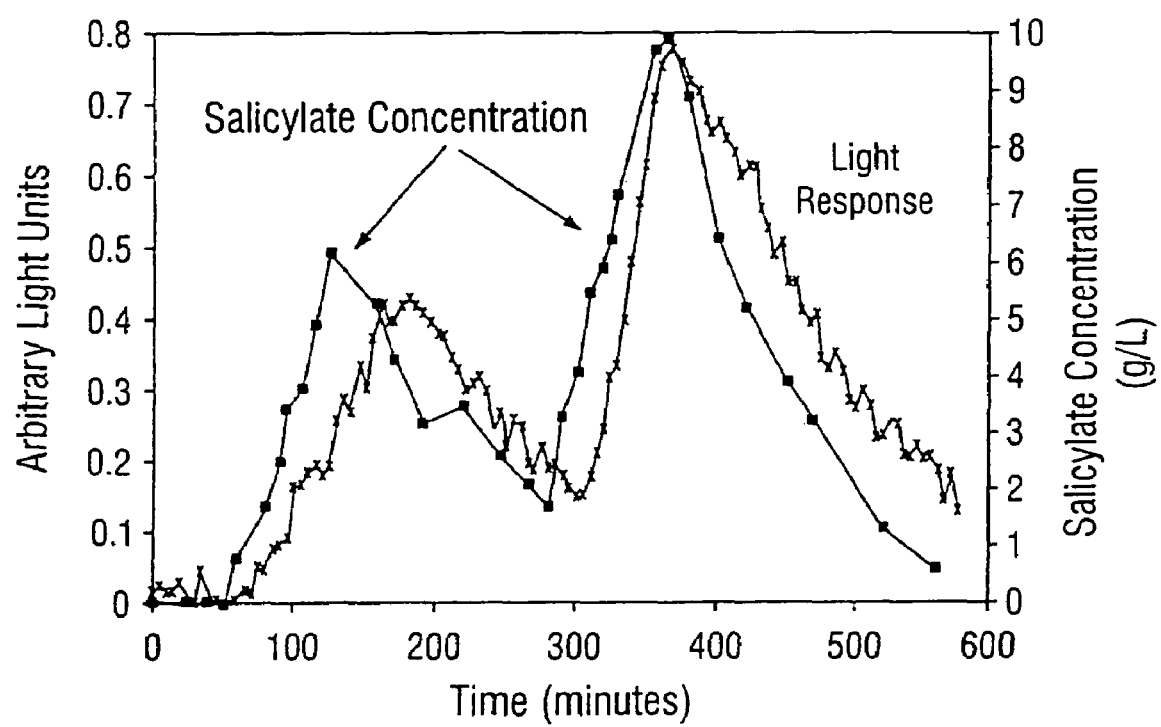
FIG. 27 shows the response of HK44 to salicylate in a flow cell. Light intensity mimicked the rise and fall of salicylate concentration in the flow cell. HK44 was immobilized in alginate on a photodiode.
Figure 28:
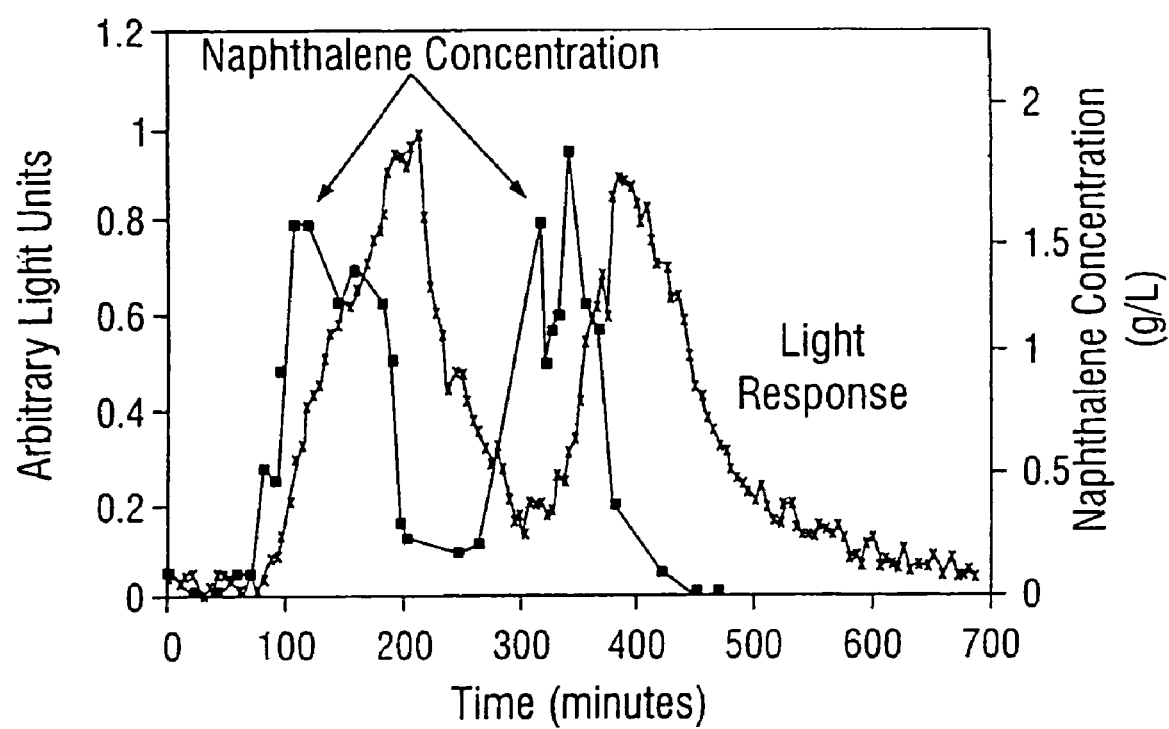
FIG. 28 shows the response of HK44 to naphthalene in a flow cell. Light intensity mimicked the rise and fall of naphthalene concentration in the flow cell. HK44 was immobilized in alginate on a photodiode. A larger lag in response was observed than in FIG. 27. The lag times may result from the way that naphthalene and salicylate are transported into the cell and consumed. Physical processes such as adsorption also have an effect on lag time.

In a second set of studies conducted independently of the degradation studies, light intensity was measured as a function of inducer concentration. The degradation studies were not well suited for measuring light response. In these studies, HK44 was immobilized in a thin layer of alginate affixed to a photodiode. A very short residence time (3 minutes.) was maintained within the flow cells. Further, these studies differed from those of the degradation studies in that the cells were not shocked by a step change in inducer concentration. Rather, the salicylate concentration was gradually increased. FIGS. 27 and 28 depict the light response and inducer concentration. Light intensity mimicked the inducer concentration, although there was a lag. In the naphthalene study, a much longer lag was observed than in the salicylate study. The lag was probably caused, at least in part, by mass transport from the bulk solution to the immobilized cells and, in the case of naphthalene, by adsorption onto the alginate. The differences in lag times may also be the result of the different ways that naphthalene and salicylate are transported in to the cell and consumed. In this set of studies, unsteady-state behavior mimicked the inducer concentration.

The HK44 demonstrated a strong response at part-per-million concentrations for both naphthalene and salicylate. PAH concentrations in soils are typically observed in parts per thousand. Optimal use of HK44 would be the detection of plume fronts where PAH and degradation product concentrations are much reduced. The HK44 was much more sensitive to naphthalene than to salicylate. Uptake mechanisms, energy levels of inducers, and effects of inducer on cell membrane liquidity possibly contribute to differences in the response to HK44 to these compounds. Naphthalene preferentially absorbs to lipids, which potentially affects membrane liquidity and may result in increased aldehyde substrates from lipid synthesis. Furthermore, naphthalene uptake is probably passive. Because salicylate is a charged ion, uptake may occur by active transport. Because naphthalene is a greater carbon and energy source than salicylate, naphthalene might increase lux substrates resulting in elevated light intensity.

NOMENCLATURE

| | |
|---|---|
| $C_{biomass}$ | biomass concentration (g cells/dm³) |
| $C_{D_i}$ | dimensionless concentration of component i in bulk phase |

-continued

NOMENCLATURE

| | |
|---|---|
| $c_i$ | dimensionless concentration of component i in the liquid phase inside the pores of the particle |
| $v$ | dimensionless adsorbed solid-phase concentration of component i |
| $C_i$ | bulk-feed concentration of component i (mol/dm$^3$) |
| $C_{i_0}$ | feed concentration of component i (mol/dm$^3$) |
| $C_{P_i}$ | pore concentration of component i (mol/dm$^3$) |
| $C_{S_i}$ | absorbed solid-phase concentration of component i (mol/dm$^3$) |
| $C_{salicylate}$ | concentration (mol/dm$^3$) |
| $D_1$ | dispersion coefficient of component i (dm$^2$/s) |
| $D_{P_i}$ | pore diffusivity of component i (dm$^2$/s) |
| $K_1$ | rate constant (mol/s g cells) |
| $K_2$ | rate constant (dm$^3$/s g cells) |
| $K_I$ | liquid-phase mass transfer coefficient (dm/s) |
| L | bed length (dm) |
| $N_{P_i}$ | rate of mass transfer (mol/s dm$^3$) |
| Pe | Peclet number with bed length as the characteristic length |
| r | position in the particle (dm) |
| $r_0$ | particle radius (dm) |
| $R_1$ | reaction rate (mol/dm$^3$ s) |
| $R_{Salicylate}$ | salicylate reaction rate (mol/dm$^3$ s) |
| S | surface area (dm$^2$) |
| t | time (s) |
| tr | mean residence time in the bed (s) |
| V | interstitial velocity (dm/s) |
| z | position in the column (dm) |
| Φ | dimensionless position in column |
| φ | dimensionless position in the particle |
| ε | bed void volume |
| $ε_p$ | particle void volume |
| ι | dimensionless time |
| $θ_{S_i}$ | dimensionless ratio of absorbed concentration in equilibrium with the maximum feed concentration of component i |

Example 4

Deployment of Encapsulated Bioluminescent Bacteria in Nutrient-Depleted Environments

*P. fluorescens* HK44 generate blue-green light when exposed to naphthalene or salicylate. The genes for bioluminescence are located in a plasmid that carries a transcriptional fusion between the promoter of a salicylate hydroxylase gene, nahG, of a naphthalene-degradation pathway and a promoterless luxCDABE gene cassette of *Vibrio fisheri* (King et al., 1990). The promoterless lux operon and activity are described elsewhere (Shaw et al., 1988).

The quantity of induced light produced by HK44 cells has been shown to be proportional to the amount of exposed naphthalene or salicylate (Heitzer et al., 1994). In liquid assays, the cells have been shown to display a linear luminescence response with 0.72 µg/l to 3.25 mg/l naphthalene and 0.4 mg/l to 20 mg/l salicylate (Heitzer et al., 1992). The cells have also been shown useful in bioassays for the detection of naphthalene in environmental contaminants. In the demonstration of an optical on-line biosensor with HK44, immobilized cells also proved applicable as they emitted a specific luminescence response when exposed to naphthalene in soil slurries, JP-4 jet fuel and leachate of manufactured gas plant soil. The information from these studies has suggested that bioluminescence technology might be used in the assessment of bioavailability and biodegradation of environmental pollutants that are significant when endpoints and regulatory standards are determined.

Bioluminescence is an expensive metabolic function as it consumes molecular $O_2$, and requires reduced flavin mononucleotide, and the synthesis of an aldehyde substrate (Hastings et al., 1985). The aldehyde must be regenerated through an ATP- and NADPH-mediated cyclic reaction during extended emission of light. The physiological burdens raise basic questions regarding the intrinsic capacity of HK44 and similar genetically engineered strains such as *Pseudomonas putida* B2 to produce stable and specific bioluminescence, upon induction in nutritionally challenged environments.

Materials and Methods

Bacterial Strains

The bioluminescent bioreporter, *Pseudomonas fluorescens* HK44 (German collection of microorganism) was used in this study (King et al., 1990). HK44 carries the catabolic plasmid pUTK21 (nah$^+$, sal$^-$, tet$^+$), which contains a nah-lux transcriptional fusion that allows monitoring of naphthalene and salicylate availability and degradation. The lux genes cassette, luxCDABE, is transfused to the nahG gene of the sal operon and inhibits the catabolism of salicylate via the plasmid-encoded pathway. The salicylate is, however, degraded by enzymes coded by chromosomal genes.

Culture Conditions

Strain HK44 was grown in 500-ml conical flasks containing 100 ml yeast extract/peptone/glucose (YEPG) growth medium with 14 mg/l tetracycline. The composition of YEPG is described by Heitzer et al., (1992). The culture was grown at 27° C. on a shaker.

The organism was grown to exponential phase in YEPG medium ($A_{546}$ 0.8), immobilized in an alginate/SrCl$_2$ matrix and incubated in groundwater. Simulated groundwater was prepared in the laboratory, from a recipe provided by the in situ groundwater team at Oak Ridge National Laboratory, Oak Ridge, Tenn. This recipe was based on the composition of various groundwater samples analyzed by this team when studying groundwater contamination. Simulated groundwater contained (mg/liter distilled water) the following ingredients: CaCl$_2$166, MgCl$_2$.6H$_2$O 85, BaCl$_2$.2H$_2$O 1.8, SrCl$_2$.6H$_2$O 0.6, FeSO$_4$.7H$_2$O 25, and KNO$_3$ 17. Double-strength groundwater was prepared and diluted with the respective buffer solutions to yield single-strength groundwater with pH levels 3, 4, 5, 6 and 7. The following stocks of buffer solutions were used in adjusting the groundwater to the desired pH. A solution of 0.2 M potassium hydrogen phthalate/0.2 M HCl was used to adjust the groundwater to pH levels 3 and 4, a solution of 0.2 M potassium hydrogen phthalate/0.2 M HCl for pH 7. The groundwater was thoroughly mixed, passed through Whatman filter-paper and sterilized by autoclaving.

Incubation and Induction

Encapsulated HK44 was incubated in groundwater and in 0.1×YEPG medium. The encapsulation was done as described elsewhere (Heitzer et al., 1994). A 500-mg sample of alginate beads, encapsulating HK44, were dispensed into sterile 25-ml vials (Pierce, Ill.) containing 3 ml incubation medium, i.e., groundwater (for nutrient deficiency) and 0.1×YEPG (for nutrient surplus). For every type of incubation medium, enough vials were prepared such that a set of triplicate vials could be sacrificed for induction and analysis. There were 6 induction days: 1, 7, 14, 21, 28 and 35. All vials were incubated at 27° C.

Induction of cells was initiated by adding 1 ml induction solution to the vials. Light output was measured every 30 minutes from time zero up to 5 hours. For the control, representing the uninduced light response, 1 ml distilled water and YEP solution were added to triplicate vials from each type of incubation medium. The light values, if any, were adjusted as the background light from the light obtained from the respective treatment.

Inducer Solutions

Simple (SS) and complex (CS) inducer solutions were used in this experiment. The former consisted of sodium salicylate dissolved in distilled water, the latter consisted of sodium salicylate in YEP solution. Both solutions provided a final concentration of approximately 100 mg/l sodium salicylate. YEP in CS denotes yeast extract and polypeptone at 0.2 g/l and 2 g/l distilled water respectively.

Light Measurements

Bioluminescence was detected using a photomultiplier tube and measured in amperes. The light output is presented as nA/cfu.

Population Counts

The numbers of viable-cell-colony-forming units (cfu) of HK44 were determined for the encapsulated beads. Encapsulated HK44 were freed by dissolving the alginate matrix with 0.5 M sodium hexametaphosphate, serially diluted in phosphate-buffered saline and spread on YEPG/agar plates containing 14 mg/l tetracycline. The plates were incubated at 27° C. for 36-60 hours and the bacterial colonies were counted.

HPLC Analysis

The concentration of salicylate was determined by high-performance liquid chromatography (HPLC) before and after the induction response. A 2-ml sample of supernatant was withdrawn from each vial of a set for each treatment type and filtered through 0.2-μm-pore-size Teflon membrane filters to remove cells and debris of alginate beads prior to HPLC analysis. The HPLC unit consisted of a LC 250 binary pump (Perkin-Elmer, Groton, Conn.) and a Supelcosil LC-18 column (Supelco, Bellefonte, Pa.) and a LS-235 photodiode array detector (Perkin-Elmer). Chromatographic conditions were a continuous gradient from 0 to 60% aqueous acetonitrile between 0.5 minutes and 8 minutes and a second continuous gradient from 60% to 100% acetonitrile between 9 minutes and 14 minutes. The program ended with column equilibration for 2.0 minutes with 100% water. HPLC-grade acetonitrile and water were used in the analysis. The UV absorbance for salicylate was determined by running a 20-μl volume of the sample and detecting the peaks at wavelengths of 255 nm. The concentrations were calculated from a standard curve prepared with known quantities of the sodium salicylate dissolved in high-quality water.

Results

Data represent results from one of the three separate repetitions of this example. Encapsulated *P. fluorescens* HK44 responded to induction with both SS and CS after incubation in groundwater and 0.1×YEPG. The response time, bioluminescence magnitude and survivability varied depending on the pH and composition of the inducer solution. The observations were made the 5 hours of induction for the 6 different days. Throughout the experiment, the pH of the incubation medium fluctuated within ±0.25 unit.

Induction with SS and CS

Figure 29A:
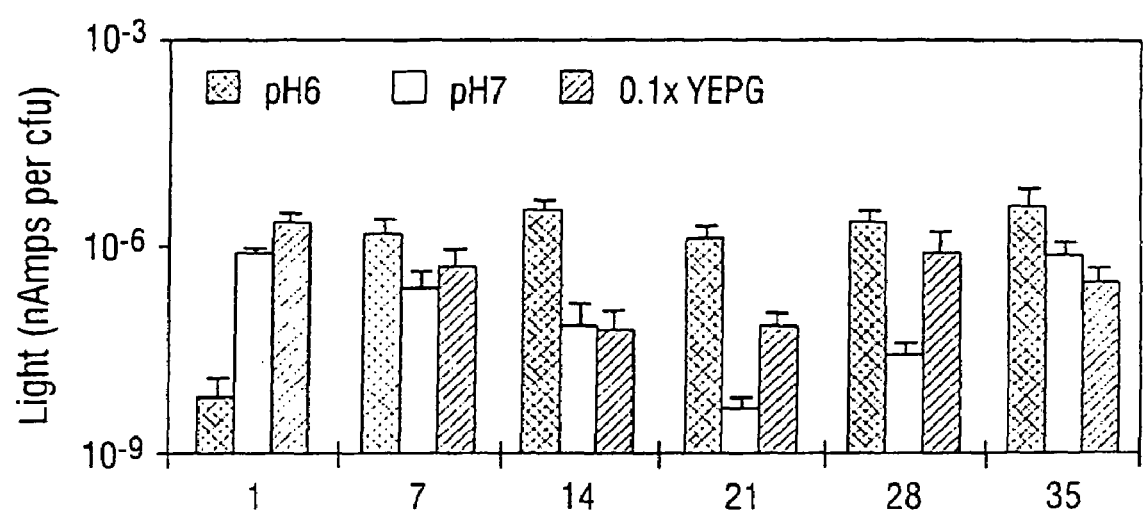
FIG. 29A and FIG. 29B show normalized logarithmic light levels within 5 h of induction. Light levels are expressed in nA $cfu^{-1}$. No data are shown for the groundwater at pH 3-5, as no light was produced. YPEG represents yeast extract/peptone/glucose medium.
Figure 29B:
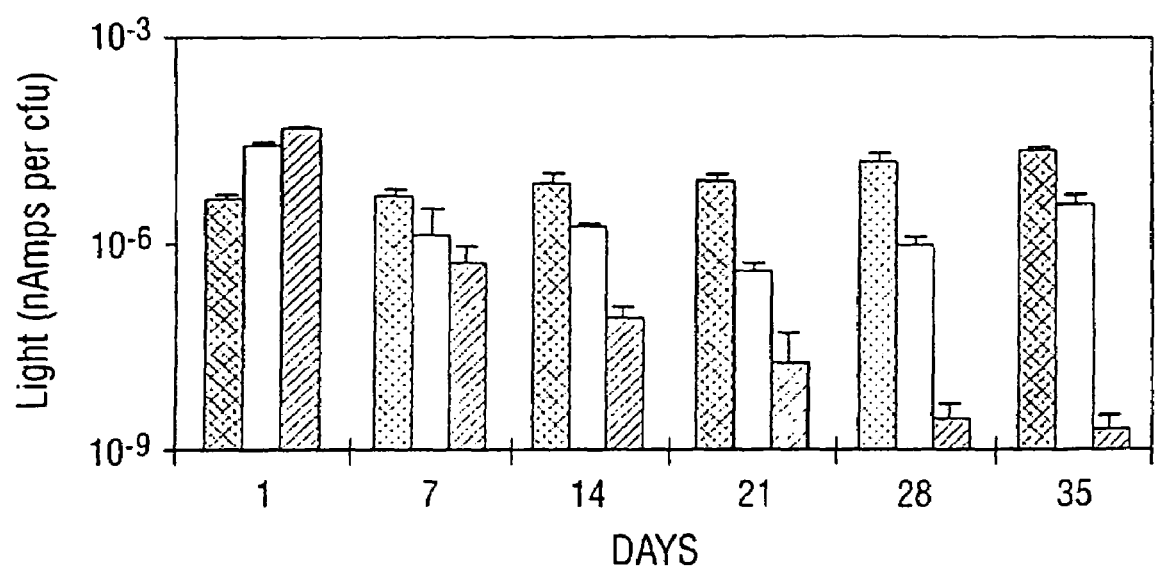

The sodium salicylate in the inducer solution induced the lux genes and increased light emission over time (FIG. 29A and FIG. 29B). No bioluminescence was observed from cells in groundwater with pH less than 6 for either of the inducers. In the other incubation conditions shown in FIG. 29A and FIG. 29B, the logarithmic light levels indicate the specific and maximum response within the 5-hours post-induction period. The light levels were normalized on the basis of the number of viable cells (cfu) in the alginate/$SrCl_2$ beads. The light levels were one order of magnitude higher with CS and than with SS.

As shown for induction by SS in FIG. 29A, log luminescence remained consistent in pH 6 groundwater on all days except day 1, the light magnitude ranging between $2e^{-6}$ and $9e^{-6}$ nA $cfu^{-1}$. In pH 7 groundwater and 0.1×YEPG, a cyclic pattern in the magnitude of the maximum light was observed. For instance, the response declined gradually during the first half of the experiment and progressively increased on later inductions (days 28 and 35).

When induced with CS, distinct responses were observed in groundwater and in 0.1×YEPG. As shown in FIG. 29B, the light levels from cells in pH 6 groundwater and at pH 7 were roughly stable on all the induction days. The responses observed in groundwater at pH 6 and 7 were almost similar in pattern when compared to the response in 0.1×YEPG, which steadily declined over the days. Nonetheless, with SS or CS, encapsulated HK44 indicated a capability for periodic induction for at least 35 days.

The lag time for response may be considered a vital indicator of the physiological status of the encapsulated cells. This was measured as the time interval in which the light level increased above the time-zero level. In groundwater at pH 6 and 7, the lag time remained the same for the first 3 induction days and was then extended at pH 7 by about 1 hour with SS. In 0.1×YEPG, however, it remained the same on all the induction days. Interestingly, the lag time was same on all days regardless of the incubation medium with CS.

Salicylate Uptake by Immobilized HK44

Figure 30A:
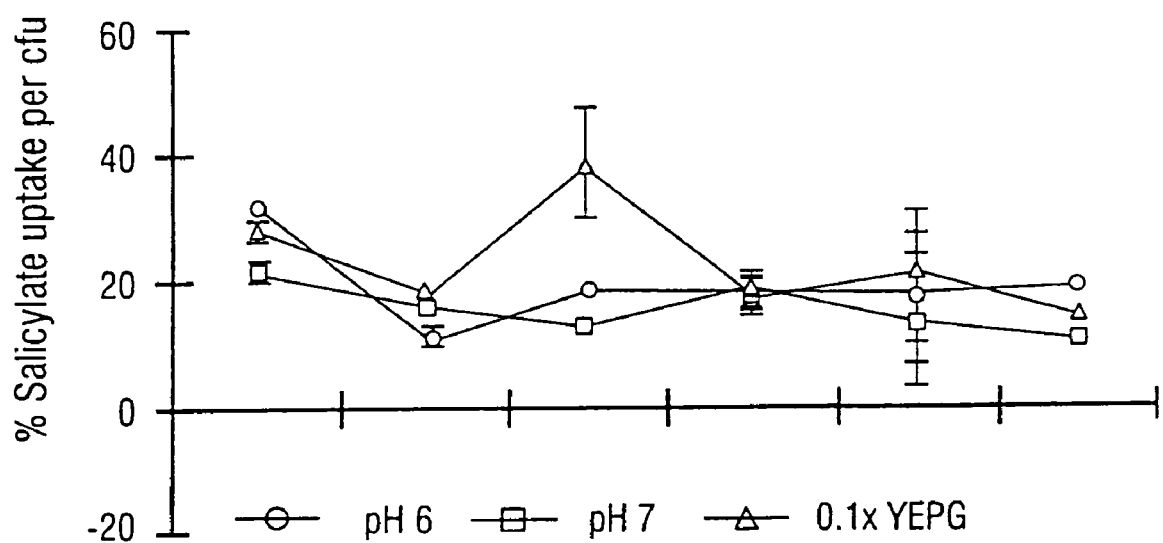
FIG. 30A and FIG. 30B show percentage salicylate uptake by immobilized HK44.
Figure 30B:
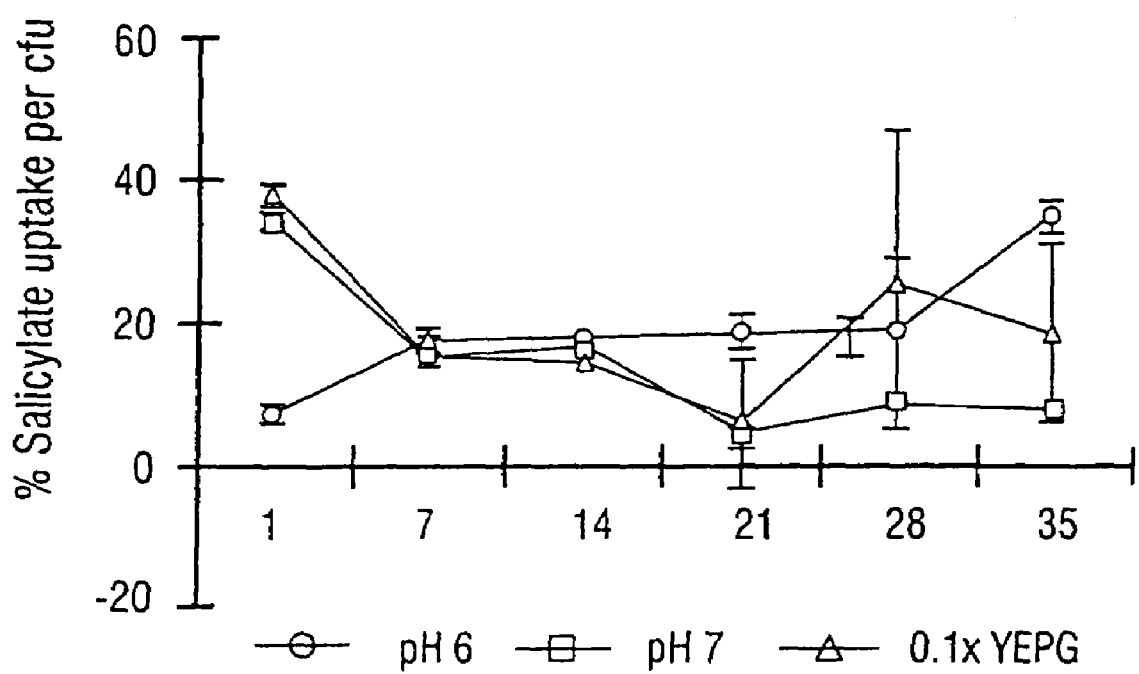

The concentration of salicylate before and after induction was used to calculate the percentage of salicylate uptake. The percentage specific uptake was determined from the number of viable cells (cfu). The data indicate that salicylate was well in excess during the 5-hour period, as only 50%-60% of the initial concentration was utilized (FIG. 30A and FIG. 30B). In the presence of SS, the percentage uptake in pH 7 groundwater was highly consistent compared to in pH 6 groundwater and 0.1×YEPG, indicating the combined effect of pH and starvation on encapsulated cells. With CS, on the other hand, uptake remained almost constant (approx. 20%), at pH 6 for all inductions except on days 1 and 35, displaying a stable response by encapsulated cells. In pH 7 groundwater and 0.1×YEPG, a cyclic pattern was observed with a gradual decline until day 21 and a steady increase on days 28 and 35.

Survivability of Immobilized HK44

Figure 31:
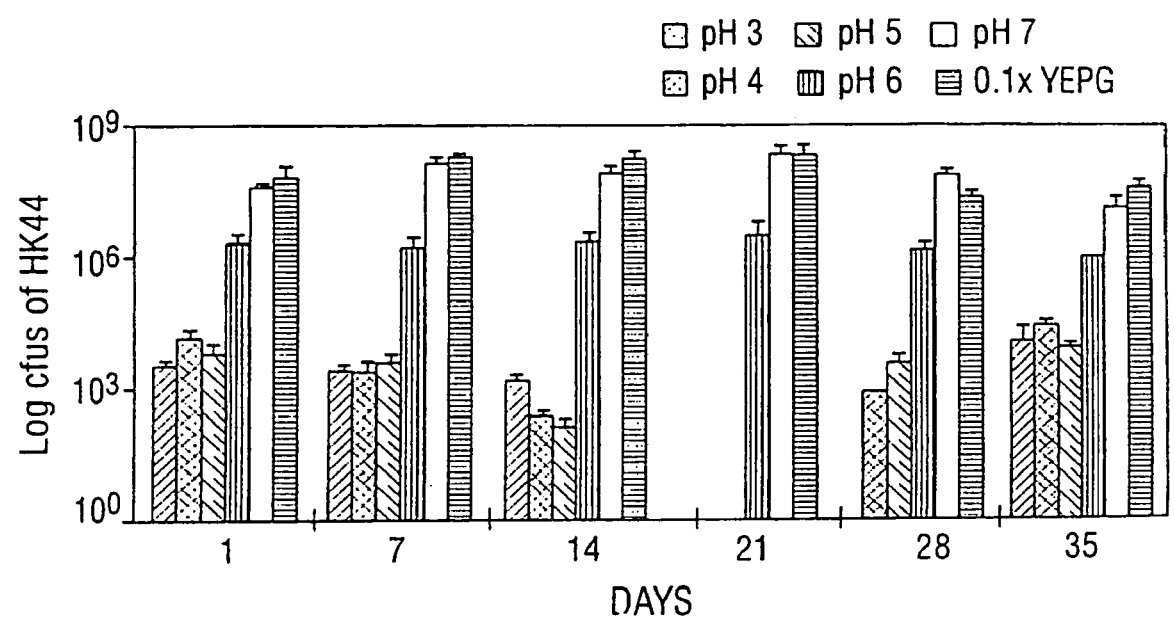
FIG. 31 shows operation of HK44 in alginate beads. The logarithm of the number of colony-forming units/alginate beads is shown.
Figure 32A:
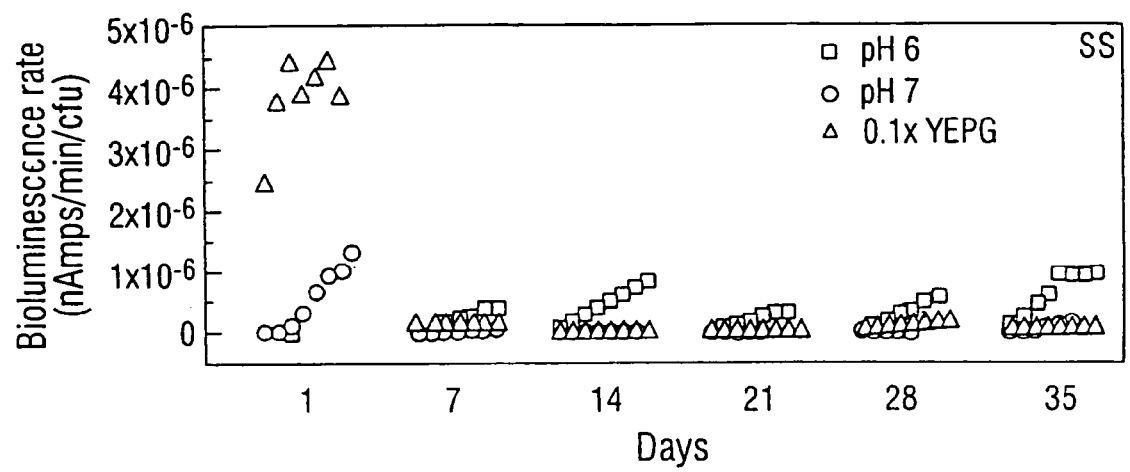
FIG. 32 shows rates of the bioluminescence reaction with SS and CS. The normalized rates were calculated from the set of light data collected within the 5 h post-induction period. This set of data was used in the calculation of the regression covariance.
Figure 32B:
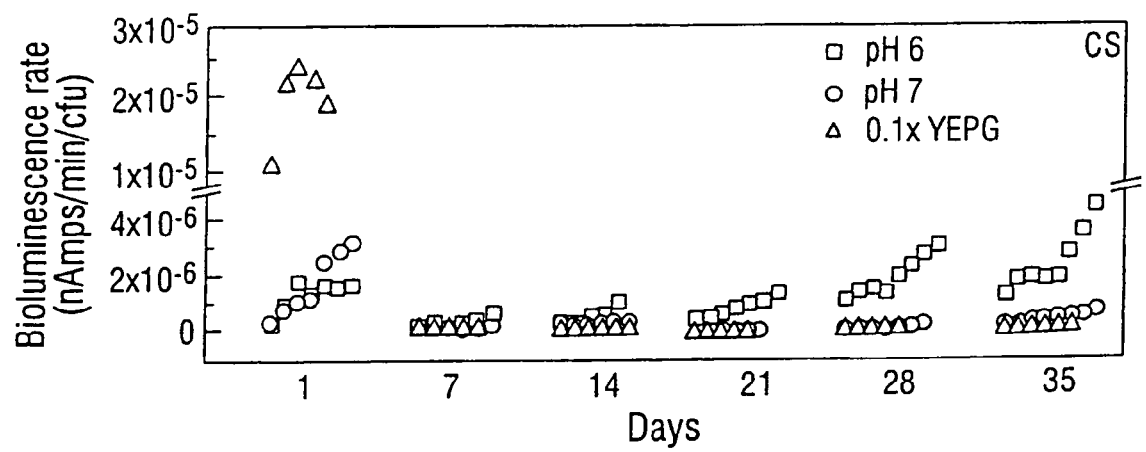

The cell viability was determined by plating an aliquot of the dissolved bead suspension on tetracycline (14 mg/l) containing YEPG/agar medium. The numbers of colony-forming units are shown in FIG. 31. These values were stable in 0.1×YEPG, and groundwater at pH 6 and pH 7 during the 35-day period. They were highly affected in groundwater with pH below 6 and declined below the detection level on day 21. They became detectable on days 28 and 35 for unknown reasons.

Bioluminescence Reaction Rate

Light production was monitored every 30 minutes and the reaction rate was calculated as nA $min^{-1}$ $cfu^{-1}$ for all assay times within the 5-hours post-induction period. A set of normalized light levels are plotted in FIG. 32 for pH 6, pH 7 groundwaters and 0.1×YEPG. The light levels indicate a linear increase in luminescence over time in the presence of saturating concentrations of salicylate. However, the trend and magnitude of the rate increase differed, depending on the induction day and solution. For the two inducer solutions, the rate increase in pH 6 groundwater, on all the induction days, was lower with SS than with CS. On day 1, the delayed response may be attributed to non-acclimatization of cells. In the case pH 7 groundwater and 0.1×YEPG, the response trend and magnitude were comparably similar.

The slopes from the regression fit for the light response are shown in Table 10 for each of the induction events. With SS, except on day 1, the slope in pH 6 groundwater was stable within the same order of magnitude. However, with CS the absolute value of the slope increased in increasing days of incubation. With SS, the slope values in pH 7 groundwater and 0.1×YEPG fluctuated in magnitude. Regardless of the inducers, increased slope values were observed in groundwater at pH 6 and 7 during the later stages of the experiment.

TABLE 10

RATE OF CHANGE OF BIOLUMINESCENCE RESPONSE$^A$

| Inducer | Time (Days) | Incubation Medium | | |
|---|---|---|---|---|
| | | pH 6 GW | pH 7 GW | 0.1 × YEPG |
| SS | 1 | $1.48e^{-9}$ (>0.99) | $1.31e^{-6}$ (0.96) | $5.78e^{-8}$ (0.88) |
| | 7 | $3.94e^{-7}$ (0.98) | $5.84e^{-8}$ (0.93) | $1.24e^{-7}$ (0.95) |
| | 14 | $8.78e^{-7}$ (0.98) | $1.64e^{-8}$ (0.90) | $4.58e^{-9}$ (0.84) |
| | 21 | $3.2e^{-7}$ (0.97) | $9e^{-10}$ (0.93) | $1.56e^{-8}$ (0.1) |
| | 28 | $5.56e^{-7}$ (0.97) | $5.68e^{-9}$ (0.90) | $1.91e^{-7}$ (0.96) |
| | 35 | $1.01e^{-6}$ (0.98) | $1.87e^{-7}$ (0.86) | $8.84e^{-8}$ (0.70) |
| CS | 1 | $1.49e^{-6}$ (0.96) | $5.38e^{-6}$ (0.93) | $8.82e^{-6}$ (0.01) |
| | 7 | $9.9e^{-7}$ (0.96) | $2.48e^{-7}$ (0.98) | $1.75e^{-7}$ (0.80) |
| | 14 | $1.55e^{-6}$ (0.95) | $3.44e^{-7}$ (0.96) | $6.51e^{-8}$ (0.88) |
| | 21 | $1.56e^{-6}$ (0.91) | $7.74e^{-8}$ (0.98) | $1.7e^{-8}$ (0.37) |
| | 28 | $3.04e^{-6}$ (0.95) | $1.87e^{-7}$ (0.94) | $1.45e^{-7}$ (0.05) |
| | 35 | $4.52e^{-6}$ (0.92) | $6.98e^{-7}$ (0.95) | $9.33e^{-8}$ (0.09) |

$^A$The values refer to the slope of a linear curve fit for the light response observed within the 5-hour post-induction period. The r2 of the linear fit is given in parenthesis.
GW groundwater;
YEPG yeast extract/peptone/glucose medium; inducer solutions;
SS simple solution,
CS complex solution.

Discussion

Observations made in this example supported evidence for a frequent response upon induction, measurable light emission and survival of the encapsulated *P. fluorescens* HK44 under nutrient-limiting conditions. In addition, the encapsulation process by itself proved sustainable for long-term biological activities. These features are critical in the design and application of a field biosensor using *P. fluorescens* HK44.

Among the simulated environmental conditions tested in this study, the cells distinctly preferred pH 6 and 7 groundwater for efficient induction and survivability. This reflected the potential limitation in the direct application of HK44 since they failed to respond in groundwater with pH below 6, either because of inhibition of the bioluminescence reaction or of cell viability or both. Interestingly, in many naturally bioluminescent bacteria the optimal pH for luciferase activity is reportedly slightly acidic (Danilov and Ismailov, 1989).

Concerns regarding the continuous effectiveness of the bacteria in a long-term biosensor application were cautiously addressed in this study. As observed, the bioluminescence reaction rate differed in magnitude and trend, in groundwater at pH 6 and pH 7 over the 35-day period. If a "cut-off" performance period can be derived for each of the groundwater samples; the performance efficacy of the bacteria can be set for a definitive time frame, allowing replacement of the old encapsulated cells with new at the end of the time frame and rendering the biosensor capable of continuous operation. For instance, in the present study, a conservative cut-off period of 28 and 14 days might be set for pH 6 and 7 GW respectively on the basis of the response (Table 10, FIG. 29A and FIG. 29B).

Encapsulation proved supportive for this type of long-term application. However, there was no indication that it influenced substrate intake or the bioluminescence reaction on the basis of studies conducted with free cells. Similar comparisons in *Pseudomonas* sp. also have revealed that immobilization has no generalized effect on the physiological activity (Shreve and Vogel, 1993).

Example 5

Immobilization and Encapsulation of Microbial Cells on Integrated Circuits

The deposition of microbial organisms on integrated circuits may be accomplished through the various protocols described below. The ultimate goal of these encapsulation methods is to provide the cells with a stable microenvironment limited from the stresses of their outer environment. Encapsulated cells can be formed into sheets or beads, almost of any thickness or diameter desired, depending on the method chosen. The small area available for cell deposition on an integrated circuit requires thin sheets (0.1-2 mm) or small diameter beads (<50 μm) to be produced. However, the high sensitivity of the integrated circuit allows for a smaller cell mass to be used. For the procedures below a cell culture containing about $1 \times 10^6$ to about $1 \times 10^8$ cfu/ml is typically grown and an about 1 to about 5 g wet weight of these cells may be utilized in the encapsulation protocol.

Numerous matrices are available for encapsulation. Polydimethylsiloxane (PDMS) is a silicone elastomer that molds and adheres to an integrated circuit surface. Polyvinyl alcohol/polyvinyl pyridine (PVA/PVP) copolymer is a biocompatible material suitable that has been used for enzyme immobilization and adheres well to graphite electrode surfaces. Latex copolymers may be utilized in various ways; for example, immobilization of cells in a porous vinyl acetate lower layer sealed with an upper layer. Cells may in some instances be adhered to a surface by electrophoretic deposition using low current densities.

Agar/Agarose

Cells may be added to molten agar or agarose (from about 1% to about 5%). Gelation occurs as the agar or agarose cools to room temperature (Kanasawud et al., 1989).

Carrageenan

A 2% solution of carrageenan may be warmed to about 70° C. to about 80° C. to initiate dissolution and then maintained at a temperature of from about 25° C. to about 50° C. The cell culture also is warmed and added to the carrageenan solution. Gel formation occurs through the addition of cold 0.1 M potassium chloride.

Polyacrylamide

Cells are mixed in a solution of acrylamide (35 g) and BIS (2.4 g). Ammonium persulfate (40 μl of a 0.40 g/ml solution) and TEMED (100 μl) are then added to initiate polymerization. Within 20 minutes sheets of encapsulated cells of any desired thickness can be sliced. Cell droplets may also be added through a syringe to the acrylamide solution to produce beads of encapsulated cells (of from about 1 mm to about 3 mm in diameter). Small diameter microbeads (from about 2 µm to about 50 µm) may be produced by spraying the cell mixture through a nebulizer or vaporizer.

Alginate

Cells are added to an about 1% to about 8% solution of alginate. Addition of 0.5 M calcium chloride or 0.1 M strontium chloride initiates polymerization. Sheets, beads, or microbeads may be produced.

Alginate encapsulated cells may be encased in 0.1 μm low adsorption filter membranes and hollow fiber membranes to allow inflow of analytes. This will inhibit alginate degradation and cellular release into the surrounding medium.

Polyurethane/Polycarbomyl Sulfonate (PCS)

Polyurethane or PCS at a polymer content of 30-50% is mixed with a 1% calcium chloride solution. The pH is adjusted to approximately 6.5 and the cell mass is added. This mixture is sprayed into 0.75% calcium alginate and beads are formed. After one hour the beads are removed, washed, and introduced into a 2% sodium tripolyphosphate buffer which dissolves the alginate layer leaving only a layer of polyurethane/PCS surrounding the cells.

Polyvinyl Alcohol (PVA)

The cell suspension is mixed with a 13% PVA, 0.02% sodium alginate mixture. Upon contact with a solution of saturated boric acid and 2% calcium chloride, gelation occurs.

Sol-Gel

The sol-gel process allows for the formation of silicon glass under room temperature conditions. Cells are combined with 0.1 M Tris-Cl and tetramethylorthosilicate (TMOS), tetraethylorthosilicate (TEOS), methyltrimethoxysilane (MTMS), ethyltrimethoxysilane (ETMS), propyltrimethoxysilane (PTMS), or polydimethylsiloxane (PDMS). Solidification times vary depending on the concentrations used (of from about 0.02% to about 0.5%). Sheets, beads, or microbeads can be produced (Armon et al., 1996).

Combination of Procedures

Many of the above methods can be combined. For example, cells can first be encapsulated in alginate, carrageenan, agar, or agarose and then encapsulated again in a stronger layer of PCS, PVA, or sol-gel. Layers of encapsulation can also be produced; alginate microbeads can be 'sandwiched' between layers of sol-gel. This provides the cell with a greater degree of protection than a single layer alone and allows the outer layer to be more compatible with the integrated circuit while maintaining an inner layer more compatible with the cells.

Amendments

Various amendments can be added during the encapsulation process to aid in cell survival. These include oxygen carriers such as polydimethylsiloxane; nutrient sources such as powdered skim milk; moisture reservoirs such as clay particles; and compounds to improve strength and flexibility, such as bean gum.

Example 6

Toxicity Applications of Bioluminescence

A number of assays have been developed that allow the measurement of toxicity of a given compound or compounds based on the effect of the compound or compounds on bioluminescent bacteria. Basically, toxicity is indicated by a decrease in the bioluminescent signal of the test bacteria. Commercially available assays include the Microtox and the Lumitox systems. These assay systems utilize bacteria that are naturally bioluminescent. Examples of applications of toxicity assays using bioluminescent bacteria are given in Table 11, including the type of organism used and the name of the assay, if commercially available.

Example 7

Bioluminescent Genotoxicity Assays

Recently, a number of assays utilizing bioluminescent bacteria have been developed to determine whether a compound is a mutagen or whether a mutagenic compound has contacted the bacteria. The assays are based on the ability of a suspected mutagen to cause distinct changes in the bacterial DNA allowing bioluminescence or the response of cells to damaged DNA caused by the mutagen. Examples of applications of bioluminescent genotoxicity assays are given in Table 12, including the type of organism and bioluminescence genes used.

Example 8

Methods of Screening Antimicrobial Agents

Organisms that are naturally bioluminescent or that have been engineered to be bioluminescent may be used to screen compounds for their ability to affect the viability of the organism. Basically, in these assays, bioluminescence will be inversely proportional to biocidal activity. Examples of applications of bioluminescent antimicrobial screening assays are given in Table 13, including the type of organism used and bioluminescence genes (if applicable).

TABLE 11

| TOXICITY APPLICATIONS OF BIOLUMINESCENCE | | | |
|---|---|---|---|
| TEST ORGANISM | LUX GENES | ASSAY | APPLICATION |
| *P. phosphoreum* | N.A.[1] | Microtox | System may be used to screen whether or not tributenyltin compounds were less toxic than tributyltin compounds as an antifouling agent. |
| *P. phosphoreum* | | Microtox | System may be used to determine whether or not pesticides in the soil were more or less toxic than the products of their degradation. |
| *P. phosphoreum* | | Microtox | Assay may be used to determine the distribution of pollution in the sediment interstitial waters of the Detroit River. |

TABLE 11-continued

TOXICITY APPLICATIONS OF BIOLUMINESCENCE

| TEST ORGANISM | LUX GENES | ASSAY | APPLICATION |
|---|---|---|---|
| *P. phosphoreum* | | Microtox | Assay may be used to determine the toxicity of breakdown products from phenolic compounds as they apply to waste water treatment. |
| *P. phosphoreum* | | Microtox | Assay may be used to determine the toxicity of Trinitrotoluene, Diaminotoluene, and Dinitromethylaniline mixtures. |
| *P. phosphoreum* | | Lumitox | Assay may be used to examine the discharges into the River Tormes in Salmanca Spain and correlate the decrease in bioluminescence to the impact on the river. |
| *P. phosphoreum* | | Microtox | Assay may be used to examine the usefulness of bioluminescence to detect cyanobacterial blooms and the associated hepatotoxins (microcystins). |
| *V. harveyi* | | NA | Assay may be used to detect biohazardous chemicals in soil and water extractions with and without acid.. |
| *V. harveyi* | | NA[1] | Assay may be used to evaluate combined or mixture toxicity of two organic compounds, nitrobenzene and trinitrobenzene. |
| *V. fischeri* | | Microtox | Assay may be used to determine the impact of point and nonpoint pollution on pore waters of two Chesapeake Bay tributaries. |
| *V. fischeri* | | Microtox | Assay may be used to determine the effect of river and wetland sediments on the toxicity of metolachlor. |
| *P. phosphoreum* | | Microtox | Assay may be used to determine petroleum hydrocarbon toxicity. |
| *P. phosphoreum* | | Microtox | Assay may be used to determine the efficacy of ultrafiltration for removal of organics from groundwater. |
| *P. phosphoreum* | | Microtox | Assay may be used to test the toxicity of marine surfactants. |
| *P. phosphoreum* | | Microtox | Assay may be used to determine the acute toxicity of *Euphorbia splendens* latex. |
| *P. phosphoreum* | | Microtox | System may be used to test for the presence of paralytic shellfish poison-like neurotoxins in a "red tide" bloom of *Gonyaulax polyedra*. |
| *P. phosphoreum* | | Microtox | Assay may be used to determine the toxicity of thio- and alkylphenols causing flavor tainting of fish from the upper Wisconsin River. |
| *P. phosphoreum* | | Microtox | Assay may be used to test the toxicity of ozonolysis by-products in drinking water |
| *P. phosphoreum* | | Microtox | Assay may be used to determine biological effects of certain metals and organic compounds found in wood preservatives. |
| *P. phosphoreum* | | Microtox | Assay may be used to determine the toxicity of 4-chloro-2-methylphenoxyacetic acid |
| *P. phosphoreum* | | Microtox | Assay may be used to determine the toxicity of water samples and extracts from the Sora river area. |
| *P. phosphoreum* | | Microtox | Assay may be used to determine the toxicity of Lake Orta (Northern Italy) sediments. |
| *P. phosphoreum* | | Microtox | Assay may be used to determine the lethal effects of azulene and longifolene. |
| *P. phosphoreum* | | Microtox | Assay may be used to determine the toxicity of granular activated carbon treated coal gasification water. |
| *P. phosphoreum* | | Microtox | Assay may be used to assess copper complexation with organic compounds. |

[1]NA, not applicable.

TABLE 12

GENOTOXICITY ASSAYS

| TEST ORGANISM | LUX GENES | APPLICATION |
|---|---|---|
| *Photobacterium phosphoreum* (dark variant) | NA[1] | A dark variant of *P. phosphoreum* is marketed from Micrabic Corporation under the name Mutatox. This system monitors genotoxicity by exposing the bacteria to the suspected mutagen and if reversion to bioluminescence occurs it suggests the compound is a possible mutagen. |

TABLE 12-continued

GENOTOXICITY ASSAYS

| TEST ORGANISM | LUX GENES | APPLICATION |
| --- | --- | --- |
| E. coli | Firefly luciferase inserted into phage λ to express the luciferase in the prophage form | Phage λ is integrated into the chromosome of E. coli forming a lysogenic strain. Since mutagens have the ability to induce prophage λ bioluminescence would indicate the presence of a suspected mutagen. Since this assay uses the luciferase only luciferin has to be added exogenously. |
| E. coli | luxAB of V. fischerii inserted into phage λ to express the luciferase in the prophase form | Assay is the same as above except the substrate for the luciferase is n-decanal. |

[1]NA, not applicable.

TABLE 13

SCREENING ANTIMICROBIAL AGENTS

| TEST ORGANISM | LUX GENES | APPLICATION |
| --- | --- | --- |
| Mycobacterium tuberculosis | Firefly luciferase cloned in front of heat shock promoter on the shuttle vector pMV261 | Strain used to ascertain the effectiveness of various antimicrobial agents. Assay is performed in vitro as the cells were lysed and the luciferin substrate added. However, luciferin can be added to whole cells. |
| Mycobacterium smegmatis | luxAB from V. harveyi cloned in front of heat shock promoter in the shuttle vector pMV261 | Strain used as a rapid way to screen for effectiveness of. antimicrobial agents. Assay uses whole cells, but requires the addition of the aldehyde substrate. |
| Listeria monocytogenes | luxAB from V. fischerii cloned in an expression plasmid | Assay used to evaluate the effectiveness of peroxygen disinfectant as a biocide for the intracellular pathogen L. monocytogenes. |
| Listeria monocytogenes | luxAB from V. fischerii cloned in an expression plasmid | Assay used to examine the biocidal effect of phenol and chlorohexidine on the intracellular pathogen L. monocytogenes. |
| Photobacterium phosphoreum | NA[1] | Assay used to ascertain the effectiveness of using acoustic energy and cavitation on bacteria by examining bioluminescent levels while varying acoustic pressures and duration. One application is the inhibition of colonization of the oral cavity. |
| E. coli and B. subtilis | luciferase gene from pyrophorus plagiophthalamus | Assay may be used to determine the membranolytic activity of serum complement. |

[1]NA, not applicable.

Example 9

Pollution Detection Using Bioluminescence Assays

Common features of microbial metabolism include the ability to recognize a compound in the environment, turn on the expression of genes required to utilize the metabolite, and, subsequently, turn off these genes when the metabolite is no longer present, the classic example is the lac operon. The lac operon promoter is repressed in the presence of simple sugars or the absence of lactose. However, when simple sugars are not available and lactose is present, the lac operon is highly expressed. When the level of simple sugars is sufficient or the lactose is depleted, the lac operon again is repressed.

Microorganisms have the ability to metabolize a wide variety of compounds. Some bacteria are able to metabolize compounds that are toxic to humans and are considered pollutants. Expression of the genes that enable pollutant metabolism is similar to that of the lac operon. Certain bacteria can recognize the presence of the pollutant in the environment, turn on the genes required for metabolism of the pollutant, and repress the genes when the pollutant is no longer present. By operatively linking a gene or genes that provide bioluminescence to a promoter of a pollutant metabolism gene or operon, one may detect the microorganism's response to the presence of the pollutant. Several examples of such a utility are given in Table 14, including the organism, lux genes, and the promoter to which the lux genes are operatively linked.

Example 10

Bioluminescent Oxygen Sensor

The ability of *Photobacterium* to emit light in response to molecular oxygen has been used to monitor low dissolved oxygen concentrations (Lloyd et al., 1981). Other examples are given in Table 15.

TABLE 14

POLLUTANT DETECTION: AROMATIC COMPOUNDS AND STRESS INDICATORS

| TEST ORGANISM | LUX GENES | APPLICATION |
|---|---|---|
| P. fluorescens HK44 | nah-luxCDABE (V. fischerii) | Strain able to semiquantitatively determine naphthalene concentrations. Also used in an on-line optical biosensor to determine the presence of naphthalene in water flowing past the sensor. |
| P. putida B2 | tod promoter cloned in front of promoterless lux genes of pUCD615 | Strain detects toluene in water samples as well as the water-soluble components of JP4 jet fuel. Strain used in the on-line monitoring of TCE degradation in a differential volume bioreactor. |
| E. coli | two heat shock promoters dnaK and grpE were fused to V. fischerii luxCDABE pUCD615 | Strains treated with a variety of environmental insults including ethanol and pentachlorophenol; showed an increase in bioluminescence correlating with the induction of the heat shock response. |
| E. coli | heat shock promoter grpE fused to the V. fischerii luxCDABE pUCD615. | E. coli strain harboring grpE-lux fusion assayed for its use in a miniature bioreactor to act as an Early Warning System for the detection of toxic levels of pollutants in the influent of a waste water biotreatment plant. |
| E. coli | mercury resistance operon fused to promoterless V. fischerii luxCDABE | Biosensor for the semiquantitiative detection of bioavailable inorganic mercury in contaminated waters. |
| E. coli | lux operon from Photorhabdus luminescens fused to the nitrate reductase (narG) promoter | Assay may be used to detect the presence of nitrate. |

[1]N.A. = Not applicable

Example 11

Bioluminescence in Eukaryotic Reporters

The luciferase and green fluorescent proteins have been used extensively as reporter genes in Eukaryotic systems. Examples of the use of luciferase genes in mammalian cell lines are given in Table 16, including the name of the cell line used, promoter and bioluminescence gene used, and a brief description of the application.

Example 12

Measurement of a Bioluminescent Signal by an OASIC

Pseudomonas fluorescens HK44 generate blue-green light when exposed to naphthalene or salicylate. The genes for bioluminescence are located in a plasmid that carries a transcriptional fusion between the promoter of a salicylate hydroxylase gene, nahG, of a naphthalene-degradation pathway and a promoterless luxCDABE gene cassette of Vibrio fisheri (King et al., 1990). The promoterless lux operon and activity are described elsewhere (Shaw et al., 1988).

A microscope slide with a culture of Pseudomonas fluorescens HK44 was placed over an OASIC. The resulting device was exposed to naphthalene and the output voltage was measured over time (FIG. 2).

Example 13

Ammonia Biosensor

Figure 49:
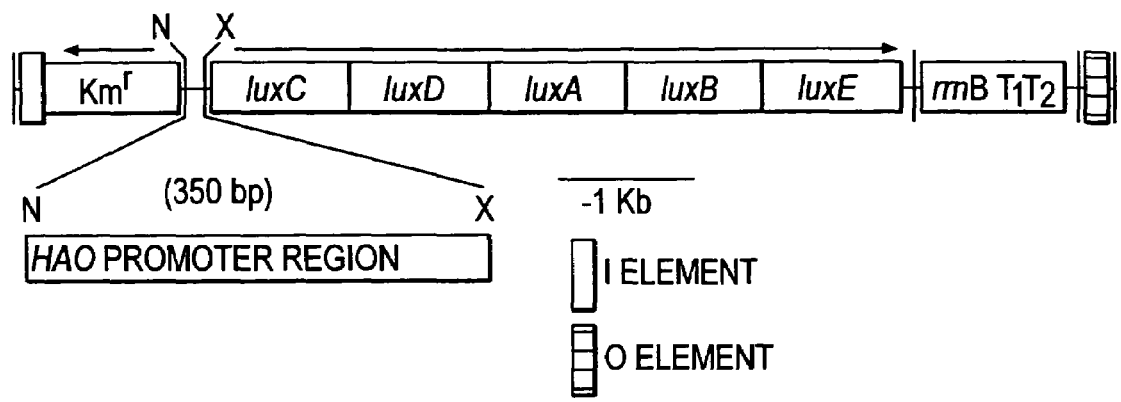
FIG. 49 shows a Mini-Tn5 containing the hao-lux fusion.
Figure 50:
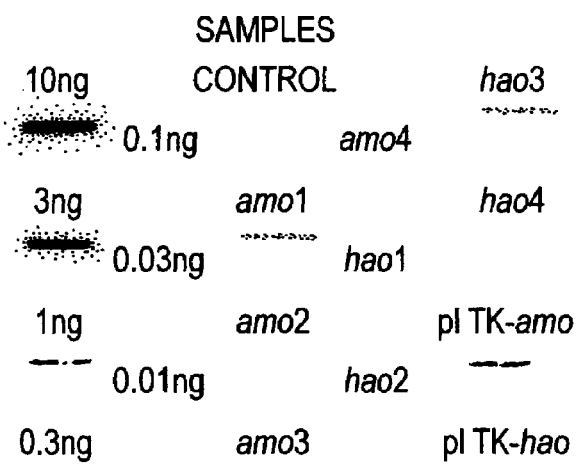
FIG. 50 shows a slot blot analysis of eight selected Kn$^r$N. europaea clones using the lux gene as a probe.

A DNA fragment containing the promoter region of the sequenced hydroxylamine oxidoreductase gene (hao) (Sayavedra-Soto, et al., 1994) was obtained by PCR amplification using Nitrosomonas europaea ATCC19178 chromosomal DNA as template. The amplified fragment was cloned, and the nucleotide sequence of the promoter was confirmed by sequencing. The hao promoter was cloned in front of the promoterless luxCDABE genes from Vibrio fischeri in a mini-Tn5 artificial transposon, which contains a kanamycin resistance gene for positive selection of transposition (FIG. 49). The transposon delivery vector was introduced into N. europaea by mating between E. coli SV17/pUTK220 and N. europaea ATCC19178 cells, and kanamycin resistance was used to select those clones with the hao-lux fusion in the chromosome of N. europaea (N. europaeaKm$^r$ hao-lux). Slot blot analysis of eight Km$^r$ clones using lux as a probe indicated that the clones amo1 and hao3 contained the transposon in the genomic DNA (FIG. 50).

Figure 51A:
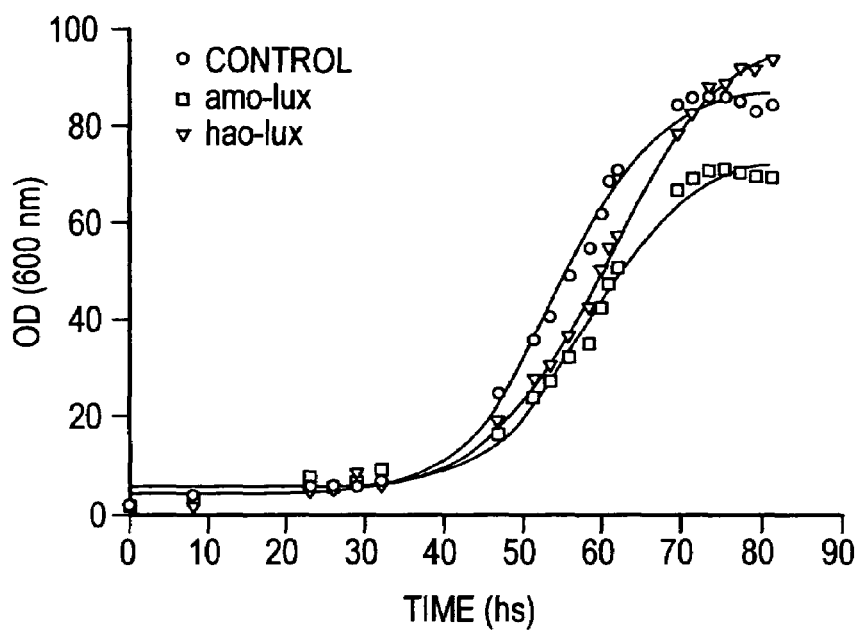
FIG. 51 shows a growth curve of N. europaea ATCC19178 (control, amo-lux and hao-lux fusions). A: optical density measurements at 600 nm; and B: nitrite production.
Figure 51B:
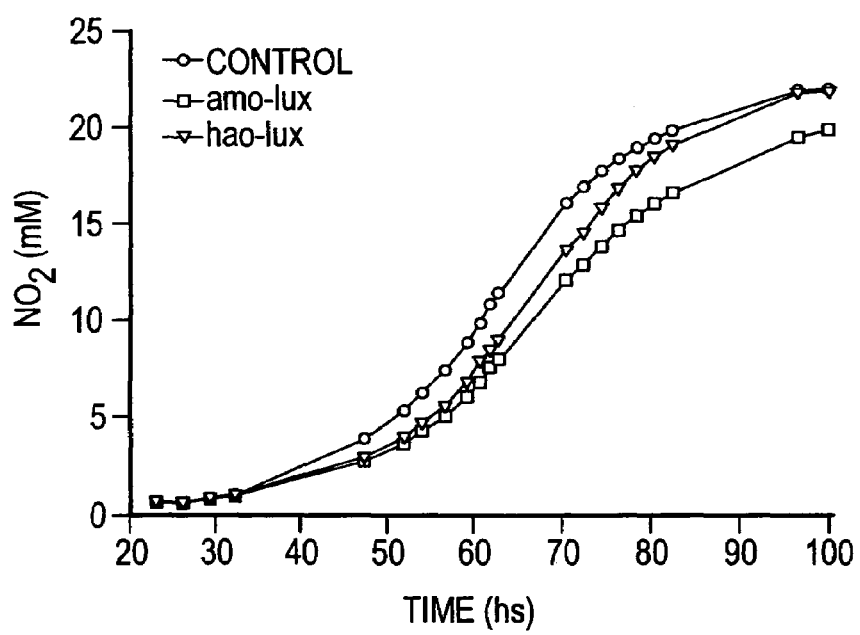
Figure 52A:
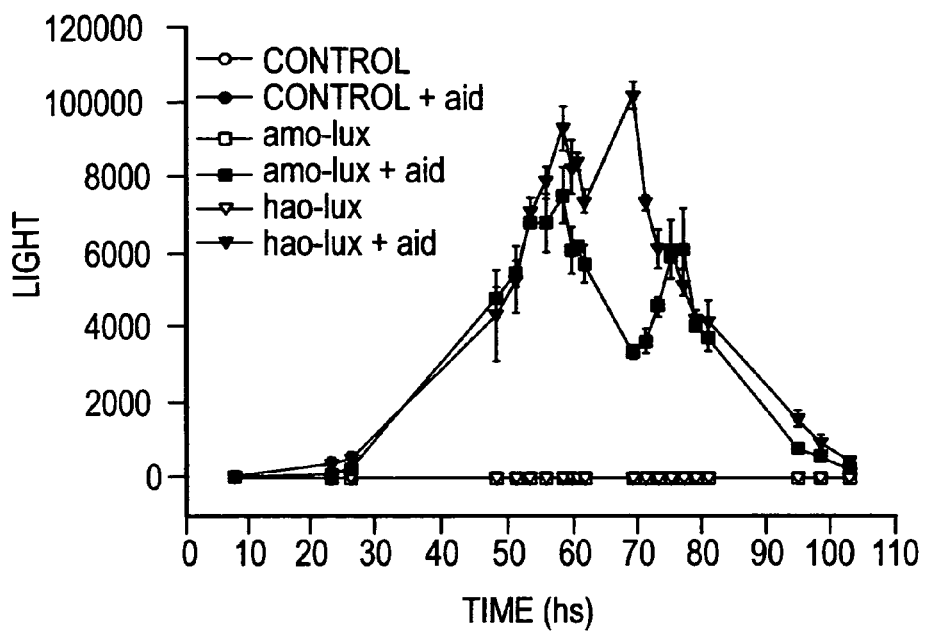
FIG. 52 shows light emission (photons/s) (A) and light/OD (B) of N. europaea ATCC19178 (control), amo-lux and hao-lux fusions.
Figure 52B:
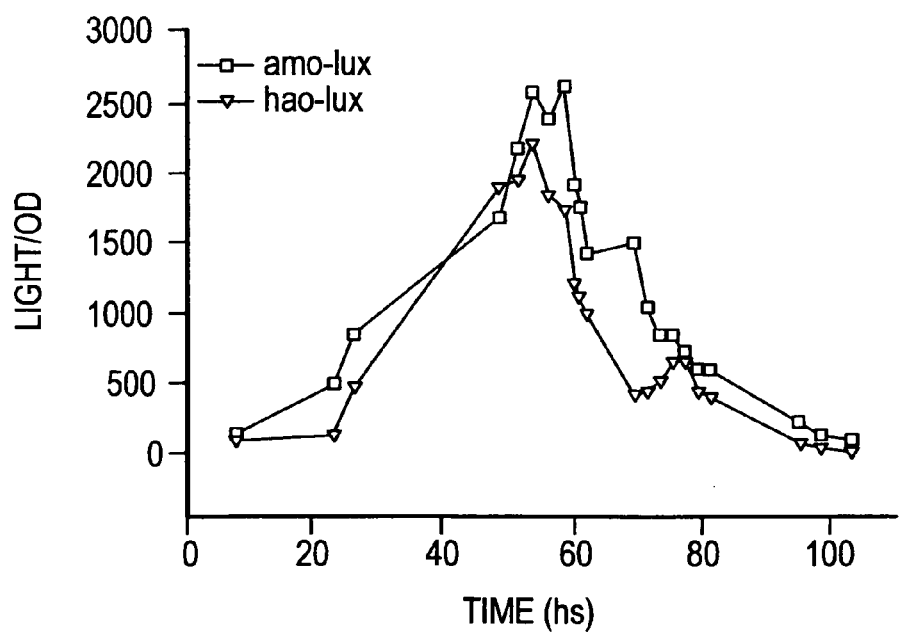

Specific bioluminescence of the hao-lux fusion was measured during the growth of N. europaeaKm$^r$ hao-lux in minimal media in the presence of 50 mM $(NH_4)_2SO_4$ (Ensign, et al., 1993). The culture was shaken at 100 rpm at 30° C. in the dark, and sampled for approximately 80 h. Specific bioluminescence (photons/sec/OD) of N. europaeaKm$^r$ hao-lux cells showed an increase with time during the first half of the exponential growth, suggesting that luciferase is accumulating in this time frame (FIG. 51A and FIG. 51B). The specific bioluminescence values steadily decreased at the end of the exponential phase, and presented background levels after 150 h of growth (FIG. 52A and FIG. 52B).

Figure 53:
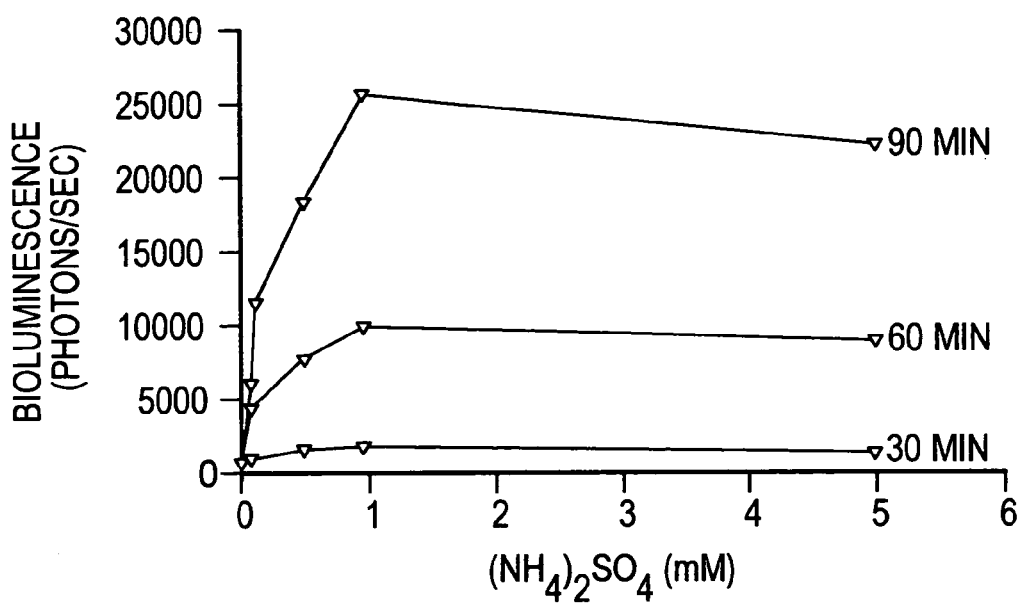
FIG. 53 shows bioluminescent response of N. Europaea Km$^r$ hao-lux to increasing concentration of $(NH)_2SO_4$ after 30, 60 and 90 min exposure.

To determine the bioluminescence response of the N. europaea hao-lux fusion to increasing concentrations of $NH_4^+$, N. europaeaKm$^r$ hao-lux cells were grown for 150 h in minimal media with 50 mM $(NH_4)2SO4$, washed in the same media in the absence of $NH_4^+$, and exposed to 0 to 5 mM $(NH_4)_2SO_4$ for 30, 60 and 90 min. An increase in bioluminescence was observed with increasing $NH_4^+$ concentrations at all tested times, being the response saturated at the higher concentrations (FIG. 53). The $NH_4^+$ detection limits were determined to be 20 μM at 30 min of exposure and 10 μM at 60 min or 90 min of exposure (threefold increase over background bioluminescence).

Example 14

Estrogen Biosensor

A reagentless yeast bioluminescent reporter system for estrogens and xenoestrogens was constructed by fusing the luxAB genes and the luxCDE genes from *Xenorhabdus luminescens*. These fusions allow the expression of these bacterial genes in eukaryotic cell lines. The modified gene cassettes can be expressed in *Saccharomyces cerevisiae* cells using the yeast expression vector pYES2.

Initially, the luxAB genes were fused by constructing oligonucleotides that amplified (using pfu polymerase) both the luxA and the luxB with the necessary genetic modifications. The resultant fragments were then be blunt end ligated and reamplified with the luxA forward primer and the luxB reverse primer. This approach was unsuccessful, as there were numerous errant PCR products.

An alternate strategy was to fuse the two genes using an oligonucleotide which was complimentary to the 3'-end of the luxA and spanning the intergenic region between the luxA and luxB including the start codon of luxB. The oligo and its complement were synthesized with the following modifications: the luxA stop codon TAG was replaced with the codon for tyrosine by substituting a C for the G; since the stop codon was eliminated a G was also inserted to put the luxA and luxB genes in the same reading frame; an AvrII restriction site was also placed into the oligonucleotide for fusing the resultant amplified luxA and luxB fragments. The luxA and luxB genes were successfully amplified and cloned into pCRII (Invitrogen, Carlsbad, Calif.). The luxB gene was then cloned into the unique AvrII site in pCRII containing the modified luxA using the added restriction site. The resultant ligation was subjected to the polymerase chain reaction using a luxA forward primer and a luxB reverse primer. The resultant PCR fragments were TA cloned and screened for light production with the addition of n-decanal. Bioluminescent colonies were isolated. Restriction analysis was performed on the resultant plasmid constructs to verify the luxAB fusion using the introduced AvrII site. The fusion showed a similar bioluminescence level to an unfused luxAB gene cassette.

These results show that the fusion of the two genes to form a monomeric protein did not significantly affect bioluminescence. To facilitate high levels of expression in the mammalian cell lines it was necessary to modify the bacterial ribosomal binding site by replacing certain bases to generate a eukaryotic ribosomal binding site. This was accomplished by mutating the sequence surrounding the luxA initiation codon to a good Kozak context using site directed mutagenesis as previously described by inserting an A at the −3 position and a G at the +4 position. Since constructs were to be screened initially in *E. coli* for light production, the unfused luxAB cassette with the Kozak modification was examined to ascertain whether or not effective translation was occurring.

Despite the Kozak modifications, the luxAB in *E. coli* was poorly expressed. These data indicated that the resultant clones of the Kozak modified luxAB fusion would have to be screened by restriction analysis as well as the absence of light. The Kozak modified luxAB fusion has been successfully amplified and inserted into the galactose inducible yeast expression vector pYES2 and inserted into *S. cerevi-siae*. Five successful transformants harboring the galactose inducible luxAB fusion were evaluated for upregulation of bioluminescence. All five were comparable. The appropriate fusions have been constructed and will be integrated with the estrogen response element to provide a bioluminescent estrogen bioreporter.

Example 15

Bioreporter Encapsulation

Figure 54:
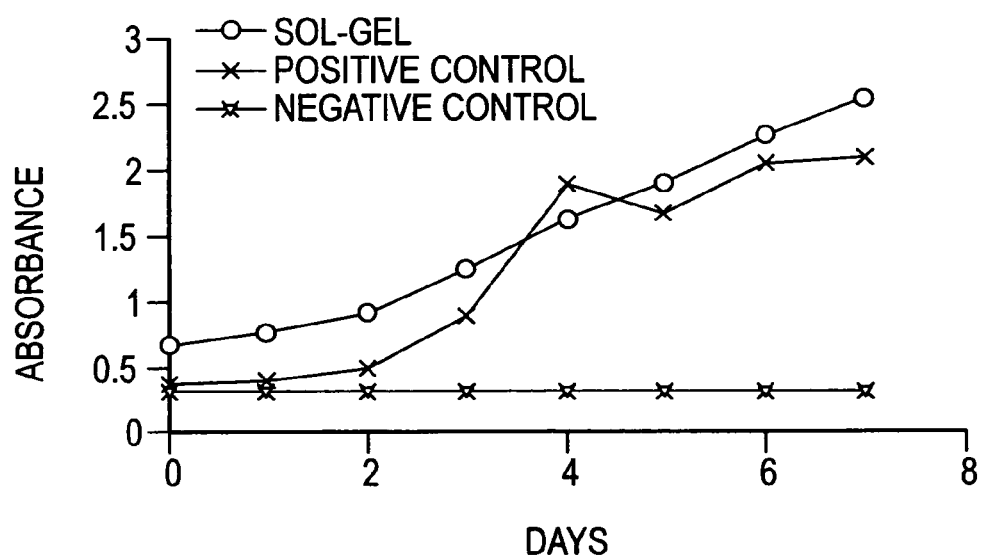
FIG. 54 shows the response of sol-gel encapsulated Saccharomyces cerevisiae HER to β-estradiol.
Figure 55:
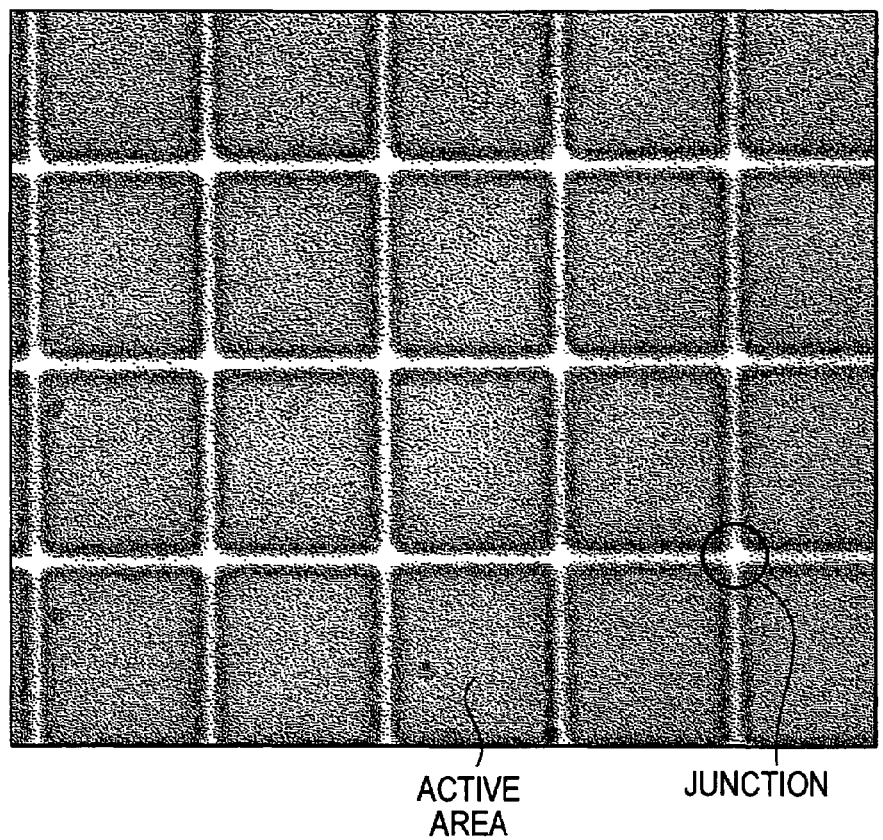
FIG. 55 shows BBIC photodetector design.
Figure 56:
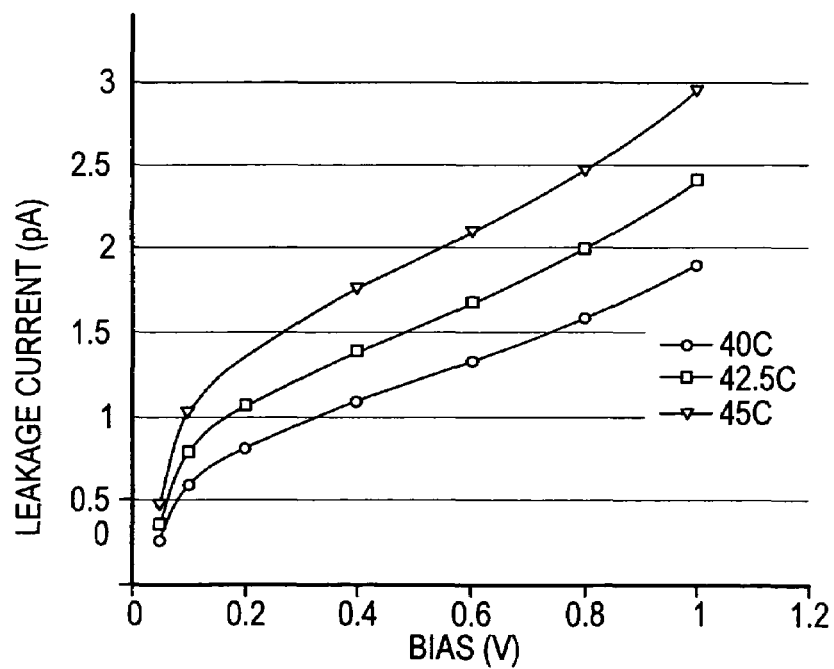
FIG. 56 shows a photodetector leakage current vs. reverse bias and temperature.
Figure 57:
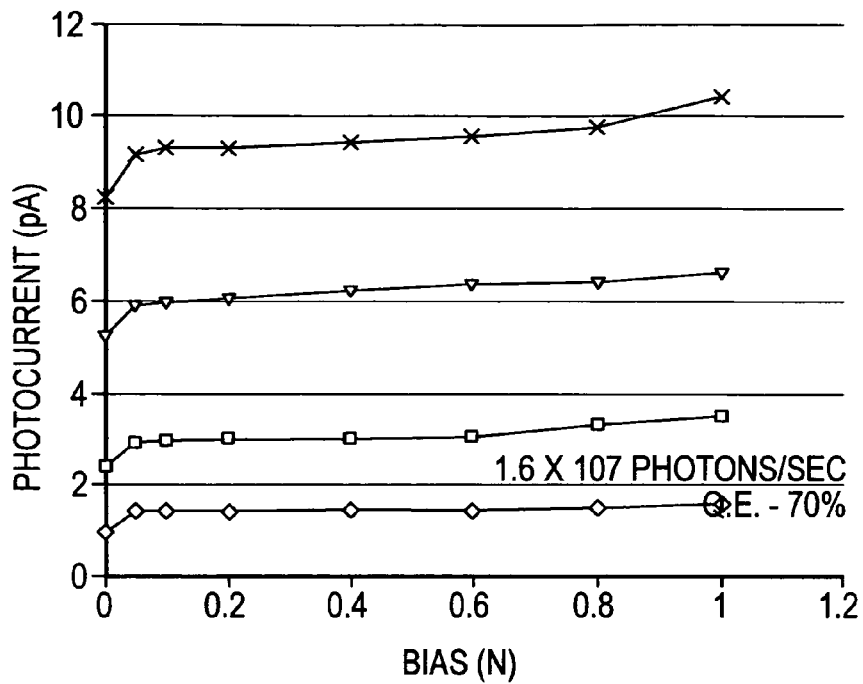
FIG. 57 shows a photodetector leakage current vs. reverse bias and temperature.
Figure 58:
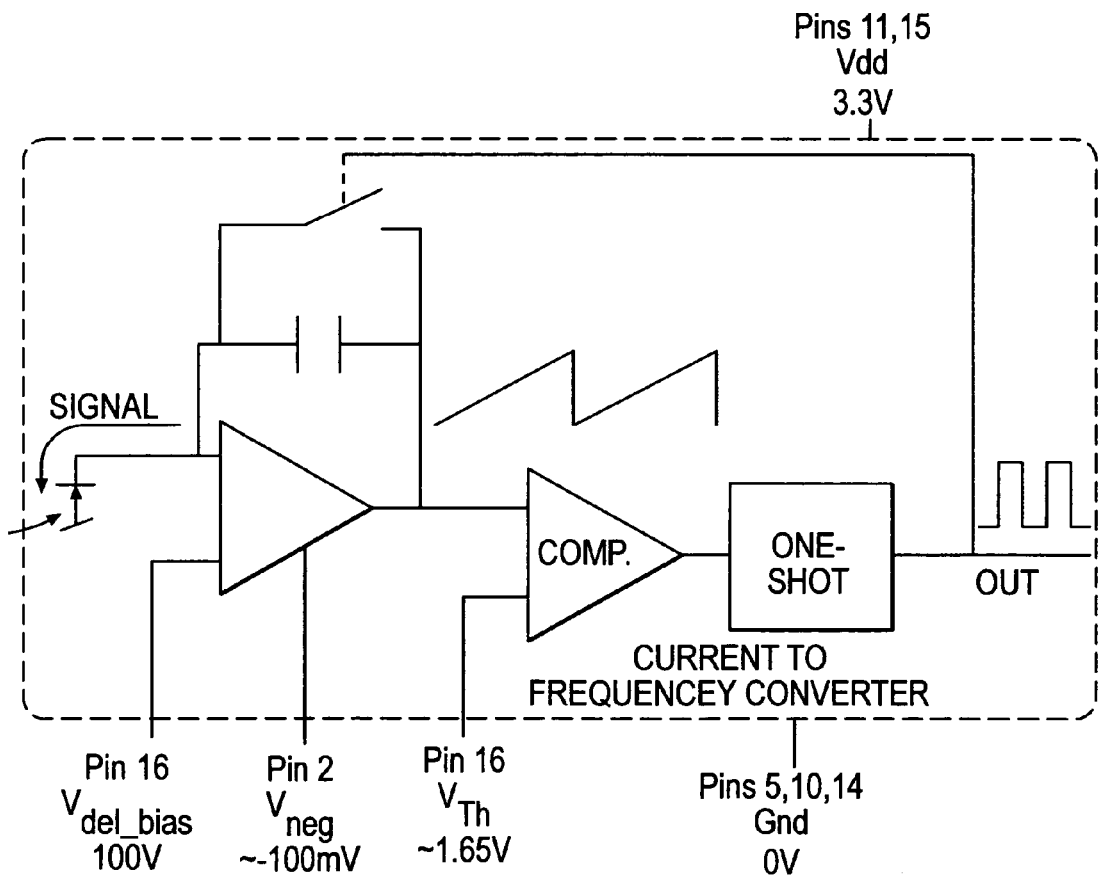
FIG. 58 shows a photosignal vs. reverse bias at four input flux levels.

Sol-gel encapsulation studies substituting another yeast strain, *S. cerevisiae* HER, a β-galactosidase bioreporter for estrogenic activity were conducted. Strain HER was successfully incorporated into the sol-gel matrix while retaining responsiveness to the estrogen inducer β-estradiol. As shown in FIG. 54, an estrogenic response was initiated in encapsulated yeast cells over a seven day period. This response remained comparable to that of the positive control non-encapsulated yeast cells.

Polydimethylsiloxane (PDMS) is also useful for encapsulation. PDMS is a silicone elastomer that molds and adheres to the integrated circuit surface. The lux bioreporter *Pseudomonas fluorescens* HK44 was encapsulated in PDMS to generate a bioluminescent response when exposed to the chemical inducer naphthalene.

TABLE 15

OXYGEN SENSORS

| TEST ORGANISM | LUX GENES | APPLICATION |
|---|---|---|
| *P. phosphoreum* | N.A.[1] | *P. phosphoreum* is used in this assay as sensor for bacterial oxygen demand (BOD). BOD is determined by the increase in bioluminescence. As the organic molecules in the test water are metabolized reduced products are shunted to the bioluminescence reactions causing an increase in bioluminescence. |
| *P. phosphoreum* | N.A.[1] | *P. phosphoreum* is used in this assay as an online controller of oxygen concentration. The bacterial oxygen sensor was used to control the optimal dissolved oxygen concentration to produce maximum $C_2H_2$ reducing activity in *Klebsiella pneumoniae*. |

[1]N.A. = Not applicable

TABLE 16

EUKARYOTIC REPORTERS

| TEST CELLS | LUX GENES | APPLICATION |
|---|---|---|
| human liver cancer cell line | CYP1A1-luc (firefly) gene fusion | A construct engineered such that when a toxic compound which would elicit a P450 response it expresses the firefly luciferase instead. The present method involves the lysis of the cells as well as the addition of exogenous luciferin to measure activity however a whole cell assay may be developed. |

TABLE 16-continued

EUKARYOTIC REPORTERS

| TEST CELLS | LUX GENES | APPLICATION |
|---|---|---|
| human hepatoma cell line Hep3B | epo promoter sequence fused to luc | bioluminescence used to monitor the induction of the erythropoiten gene. Hypoxia found to cause a 4-fold induction of gene expression in Hep3B. |
| HeLa cells | luciferase was fused to a thymidine kinase promoter | HeLa cells cotransfected with the expression vector HEG0 and the luciferase reporter plasmid harboring a Vit. A2 ERE. Antiestrogens designed and tested and found to inhibit transcriptional activity. |
| mouse fibroblast 3T3 cells | ribonucleotide reductase promoters for both subunits R1 and R2 fused with luciferase | Reporter constructs utilizing the R1 and R2 promoter-luciferase constructs transformed into mouse fibroblast cells. R1 luc shows a 3-fold induction and R2 luc a 10-fold increase upon exposure to UV light in a dose dependent manner. |
| estrogen receptor-positive breast cancer cell line | reporter plasmid contains a thymidine kinase promoter fused to a firefly luciferase | luciferase reporter used to screen for both estrogenicity and antiestrogenicity |
| Hela cells | firefly luciferase controlled by the Gal-4 promoter | Chimeric proteins comprising the DNA binding domain of Gal4 yeast proteins and hormone binding domains of various steroid receptors are placed into the cell lines containing the Gal-4-luciferase construct to test the biological activities of steroid hormones. |

Example 16

Bioluminescence Detection

Bioluminescence was determined for cultures containing different concentrations of *P. fluorescens* 5RL cells growing in LB supplemented with 10 ppm of the inducer molecule salicylate and 14.7 mg/L tetracycline (FIG. 46). Bioluminescence was determined using the integrated circuit microluminometer and a light-tight enclosure mounted above the chip. Linear regression analysis showed that the data fit a linear model indicating that bioluminescence per cell remains constant for cell concentration ranging from $4 \times 10^5$ to $2 \times 10^8$ CFU/mL and for detector responses ranging from 0.05 to 20 pA. Using a linear model, the limit of detection (2 sigma) for this experimental geometry was estimated to be $4 \times 10^5$ cells per mL. At cell concentration greater than $4 \times 10^8$ CFU/mL, the bioluminescence decreased possibly due to oxygen limitation caused by the quiescent conditions of the vial (FIG. 47).

The results obtained with the BBIC microluminometer were compared with results collected with the Azur luminometer at each cell concentration (FIG. 48). The data showed that the measured bioluminescence responses were proportional for cell concentrations ranging $4 \times 10^5$ to $2 \times 10^8$ CFU/mL, indicating that the BBIC microluminometer gave consistent results compared to standard PMT-based detection systems.

The attractive attributes of the sensor developments described here are the potentials for creating wholly self contained biosensors that require no exogenous reagents beyond what can be provided on the IC and that the IC can function independently of any other instrumental components.

Example 17

Modifications to CFC Circuit for Low Reverse Bias Operation

FIG. 43 shows the portion of the CFC circuit involved in the biasing of the photodiode. The switch across capacitor Cf is realized with a transistor. As shown in this figure, a single transistor is usually employed. However, if the leakage current through this transistor exceeds the leakage current of the photodiode, then the circuit does not operate correctly. In practice this places a lower limit to the reverse bias on the photodiode.

FIG. 44 illustrates a solution to this problem. A two-transistor switch with a path to ground at the central point was employed. Although the path is shown as a current source, in practice it can be a resistor or another transistor with a fixed gate voltage. In this circuit, the leakage current passes through the first transistor, but is shunted to ground by the current source. Therefore, no leakage current finds its way to the photodiode node.

Integrated Microluminometer

Microluminometer Chip

FIG. 45 shows a photograph of the complete microluminometer chip. The chip measures 1.9 mm×1.9 mm with the photodetector occupying ~33% (1.2 mm$^2$) of the total chip area. For testing purposes the chip was mounted in a 40-pin ceramic dual inline package The level of light that is detectable on the chip is an important performance parameter of a BBIC. Modifications to the design of the photodetector and the front-end analog processing circuitry improved the minimum detectable signal by at least 20-30%. In particular, the modifications include:

(1) Selection of an n-well/p-substrate junction for photodetection. This junction has significantly lower noise and higher quantum efficiency.
(2) Selection of an electrode configuration that minimizes photodiode leakage current and capacitance (both of which increase noise) without significantly impacting quantum efficiency.

Additionally, changes have been made to the front-end processing circuitry which allow the photodiode to work at a reverse bias of 0V.

The many potential applications for BBICs include environmental monitoring, food and water quality testing, in vivo sensors for disease detection and management, and other remote applications where size, power consumption, and cable plant concerns are the dominant issues. Therefore, the integrated circuit (IC) portion of the BBIC should reside on a single chip, be compatible with battery operation, and be compatible with RF circuits for wireless telemetry in addition to allowing the integration of high-quality photodiodes and low-noise analog signal processing. We chose a standard 0.5-µm bulk CMOS process that meets optical and signal processing requirements, while allowing the integration of RF circuits operating in the 916-MHz band. The design and performance of the two major components of the microluminometer: the CMOS photodiodes and the front-end signal processing are discussed.

CMOS Photodiodes

CMOS technology allows the realization of phototransistors, photodiodes, and photogates without any modification or additions to the standard processing steps. As normally used, these devices have broad spectral responses that peak in the red/near infrared region. Peak external quantum efficiency of 50%-80% has been reported for CMOS photodiodes (Kramer, et al., 1992).

FIG. 38 shows two junctions available for the realization of CMOS photodiodes. The shallower junction (p-diffusion/n-well) is desirable for this application since its response peaks near the 490-nm wavelength of the bioluminescence, yet drops off quickly at longer wavelengths (Simpson, et al., 1998). However, the quantum efficiency of p-diffusion/n-well photodiodes in small geometry CMOS processes is low (typically less than 10%). One possible explanation is that the shorter drive-in diffusion step for small geometry processes is insufficient to anneal the lattice damage created by the ion implantation step, thereby leaving a high density of charge traps in these diffusions. In this case, the large number of charge carrier traps will severely degrade the quantum efficiency in the blue and green optical regimes. Regardless of the mechanism, the p-diffusion/n-well junction is not suitable for low-level luminescence detection, leading to selection of the n-well/substrate photodiode for the microluminometer transducer.

The physical layout of the electrodes affects both the quantum efficiency and the reverse leakage current of the photodiode. Two possible electrode configurations are shown in FIG. 39. In the first configuration the n-well electrode covers the entire active region of the photodiode. The advantage of this approach is that all the photo-generated charge is produced in the n-well and must only diffuse a short distance to the n-well/substrate junction without being trapped to produce a photocurrent.

The second approach in FIG. 39 uses an array of small n-well/substrate junctions spread across the active region of the detector. This approach minimizes the degradation of noise performance caused by detector capacitance and leakage current. However, charge created in the substrate regions must diffuse a relatively long distance without being trapped to produce a photocurrent. In principle one could calculate the optimum spacing between electrodes given a detailed knowledge of material parameters such as the diffusion length and the surface recombination velocity. As these parameters are likely to vary from run to run, empirical determination of optimum spacing may be the best strategy. For this design, 5.6 µm×5.6 µm electrodes spaced 12.6 µm apart as shown in FIG. 40 were selected.

For use with bioluminescent bioreporters, it is desirable to minimize the photodiode reverse leakage current for two reasons. First, the power spectral density of the detector white noise depends directly on the magnitude of the dc leakage current. Possibly more important is the inability to distinguish a low-level dc luminescent signal from a dc leakage current. Variations in the leakage current as a function of temperature cannot be distinguished from a change in the bioluminescence. Conventional solutions, such as chopping the optical signal, are not practical for this integrated, single-chip, analytical instrument.

The ideal diode equation, $$I_f = I_s \left( e^{\frac{V_f}{V_T}} - 1 \right) \quad (36)$$

where
$I_f$=forward current
$I_s$=reverse saturation current
$V_f$=forward bias
$V_T$=thermal voltage ($\approx$26 mV@room temperature)

describes two competing current components: 1) electrons/holes on the n/p side overcoming the potential barrier; and 2) holes/electrons on the n/p side diffusing to the edge of the space charge region and being swept across $$I_r = -I_s. \quad (37)$$

At zero bias these two components are in dc equilibrium, so the dc leakage current is zero. However, these currents are uncorrelated, so their noise power spectral densities (PSD) add. This simple analysis predicts that the noise PSD at zero bias is higher than it is at any reverse bias.

Unfortunately, the situation is not that simple. Equation (36) describes moderate to strong forward bias current well. However, at weak forward bias or in reverse bias, equation (36) under predicts the magnitude of the current because of surface and generation/recombination effects. $I_r$ as well as $I_f$ will depend on bias, and it is not certain at what bias level the minimum noise is found. However, zero bias is certainly where the minimum dc leakage current, and therefore the greatest immunity from thermally generated false signals, is found.

FIG. 41 shows the reverse leakage current versus reverse bias for the photodiode of FIG. 40 at three different temperatures. This figure clearly shows that operating at reduced bias greatly reduces the magnitude of the temperature drift of the leakage current. FIG. 42 shows the measured photodiode signal versus reverse bias for the photodetector shown in FIG. 40 at four different light levels. This figure demonstrates that the quantum efficiency has a weak dependence on bias for reverse biases above 50 mV. In addition, this figure shows the quantum efficiency of this detector to be ~68% at 490 nm (1.75 pA photocurrent for an input flux of 1.6×10$^7$ photons/sec.), which indicates that the spacing between n-well electrodes can be increased, thereby further decreasing leakage current and detector capacitance.

Signal Processing

The simplest noise approximation for the microluminometer assumes the detection of a dc signal in wide band white noise. The input signal, x(t), may be approximated as a step function u(t), where the impulse response of the matched filter is:

$$h_{opt}(t) = ku(t_0 - t), \quad (38)$$

and where k is a constant and $t_0$ is the time of the measurement [28]. The optimal impulse response has an output at negative infinity for an impulse input at t=0, and is therefore non-causal and non-realizable. However, the causal portion of the filter can be realized as a gated integrator with the gate open for 0<t<$t_0$ (FIG. 43).

The noise at the output a gated integrator due to white detector current noise at the input is:

$$\overline{v_{no}^2} = \frac{\overline{i_n^2} t_0}{2 C_f^2}, \quad (39)$$

where
$\overline{v_{no}^2}$ = mean square output voltage noise
$\overline{i_n^2}$ = mean square photodiode current noise
$C_f$ = integrator feedback capacitor,
while $$v_0^2(t_0) = \frac{i_p^2 t_0^2}{C_f^2}, \quad (40)$$

where
$v_o^2(t_o)$ = output signal power at $t_o$
$i_p$ = photocurrent.
From equations (6) and (7) the signal-to-noise ratio (SNR) is $$SNR = \frac{2 i_p^2 t_0}{\overline{i_n^2}}, \quad (41)$$

and continues to improve as $t_0$ increases.

Practical concerns will limit $t_0$ to several minutes. A remaining problem is capacitor values that are too large for on-chip implementation. This was solved by using the hybrid analog/digital integration scheme as shown in FIG. 44. In this circuit, an analog integrator and a discriminator convert the photodiode current into a train of digital pulses (current-to-frequency converter (CFC)). These pulses are counted for a fixed time ($t_0$), and the result is a digital word that is proportional to the photocurrent. This scheme has several advantages compared to other processing options, including fast recovery from overload and ease of analog-to-digital conversion. It has been reported as useful in optical detection systems (deGraff and Wolffenbuttel, 1997).

Microluminometer Chip

FIG. 45 shows a photograph of a complete microluminometer chip. In this example, the chip measures 2.2 mm×2.2 mm with the photodetector occupying~25% (1.2 mm$^2$) of the total chip area. For testing purposes the chip was mounted in a 40-pin ceramic dual inline package.

All of the apparatus, compositions and methods disclosed and claimed herein can be made and executed without undue experimentation in light of the present disclosure. While the apparatus, compositions and methods of this invention have been described in terms of preferred embodiments, it will be apparent to those of skill in the art that variations may be applied to the apparatus, devices, methods and in the steps or in the sequence of steps of the methods described herein without departing from the concept, spirit and scope of the invention. More specifically, it will be apparent that certain agents which are functionally related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An integrated microluminometer, comprising:
an integrated circuit chip that includes at least one n-well/p-substrate junction photodetector for converting light received into a photocurrent, and a detector on said chip for processing said photocurrent.

2. The integrated microluminometer of claim 1, wherein said photodetector includes a distributed electrode configuration comprising a plurality of spaced apart electrodes disposed on an active region of said photodetector.

3. The integrated microluminometer of claim 1, wherein said detector comprises a current-to-frequency converter.

4. The integrated microluminometer of claim 1, wherein said detector comprises an analog gated integrator.

5. The integrated microluminometer of claim 4, further comprising a discriminator connected to an output of said gated integrator, wherein said discriminator converts said photocurrent into a train of digital pulses, said pulses being are counted for a fixed time, wherein a digital word is generated which is proportional to said photocurrent.

6. The integrated microluminometer of claim 5, wherein said discriminator comprises a comparator coupled to a one-shot, said one-shot coupled to a gated counter, wherein an output of said gated counter is said digital word.

7. An integrated microluminometer, comprising:
a light detection system including at least one p-n junction based photodetector for converting light into electrical current and circuitry for reducing or canceling recombination and generation current produced by said photodetector.

8. The integrated microluminometer of claim 7, wherein said circuitry for reducing or canceling recombination and generation current comprises at least one diode in a feedback loop having an area smaller than an area of said photodetector, said diode supplying forward bias current that cancels out photocurrent associated with said recombination and said generation current.

9. The integrated microluminometer of claim 7, wherein said circuitry for reducing or canceling recombination and generation current maintains said photodiode at essentially zero bias.

10. A method of measuring bioluminescence, comprising the steps of:
providing the microluminometer of claim 3 having a modified bioluminescent microorganism that emits light in the presence of a selected analyte held on a surface of said chip;
contacting said modified bioluminescent microorganism with a sample suspected of containing said analyte, and
operating said microluminometer of claim 3 and counting light pulses produced for a fixed time to determine said photocurrent, wherein said photocurrent is proportional to number of pulses that measure bioluminescence when said analyte causes said bioluminescent microorganism to emit said light.

11. The method of claim 10, wherein said modified bioluminescent microorganism is encapsulated in a sol-gel matrix held on said surface.

* * * * *